(12) United States Patent
Jiao et al.

(10) Patent No.: US 9,617,212 B2
(45) Date of Patent: Apr. 11, 2017

(54) ISOINDOLIN-1-ONES AS MACROPHAGE MIGRATION INHIBITORY FACTOR (MIF) INHIBITORS

(71) Applicant: Controlled Chemicals, Inc., Colmar, PA (US)

(72) Inventors: Jingliang Jiao, Lansdale, PA (US); Jules A. Shafer, Gwynedd Valley, PA (US)

(73) Assignee: Controlled Chemicals, Inc., Colmar, PA (US)

( * ) Notice: Subject to any disclaimer, the term of this patent is extended or adjusted under 35 U.S.C. 154(b) by 0 days.

(21) Appl. No.: 14/570,619

(22) Filed: Dec. 15, 2014

(65) Prior Publication Data
US 2015/0175540 A1    Jun. 25, 2015

Related U.S. Application Data

(60) Provisional application No. 61/916,988, filed on Dec. 17, 2013.

(51) Int. Cl.
*C07D 209/46* (2006.01)
*A61K 31/4035* (2006.01)
*A61K 31/5377* (2006.01)
*A61K 45/06* (2006.01)
*A61K 39/00* (2006.01)

(52) U.S. Cl.
CPC ........ *C07D 209/46* (2013.01); *A61K 31/4035* (2013.01); *A61K 31/5377* (2013.01); *A61K 45/06* (2013.01); *A61K 39/00* (2013.01); *A61K 2039/542* (2013.01); *A61K 2039/57* (2013.01); *A61K 2039/58* (2013.01)

(58) Field of Classification Search
CPC .................................................. C07D 209/46
See application file for complete search history.

(56) References Cited

U.S. PATENT DOCUMENTS

| 7,378,416 | B2 | 5/2008 | Billich et al. |
| 8,362,053 | B2 | 1/2013 | Al-Abed |
| 2010/0267712 | A1 | 10/2010 | Heemskerk et al. |
| 2010/0267714 | A1 | 10/2010 | Jorgensen et al. |
| 2011/0245247 | A1 | 10/2011 | Braje et al. |
| 2012/0040974 | A1 | 2/2012 | Jorgensen et al. |

FOREIGN PATENT DOCUMENTS

| WO | WO 99/58096 | A2 | 11/1999 |
| WO | WO 2005/021546 | A1 | 3/2005 |
| WO | WO 2006/045505 | A1 | 5/2006 |
| WO | WO 2007/070961 | A1 | 6/2007 |
| WO | WO 2010/021693 | A2 | 2/2010 |
| WO | WO 2012/009649 | A1 | 1/2012 |
| WO | WO 2012/058133 | A1 | 5/2012 |
| WO | WO 2012/142498 | A2 | 10/2012 |
| WO | WO 2013/028297 | A1 | 2/2013 |

OTHER PUBLICATIONS

Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Cancer [online], [retrieved on Jul. 6, 2007]. Retrieved from the internet, URL; http://en.wikipedia.org/wiki/Cancer.*
International Search Report and Written Opinion mailed Apr. 16, 2015 for International Application No. PCT/US2014/070351.
Abe et al., Regulation of the CTL response by macrophage migration inhibitory factor. J Immunol. Jan. 15, 2001;166(2):747-53.
Al-Abed et al., ISO-1 binding to the tautomerase active site of MIF inhibits its pro-inflammatory activity and increases survival in severe sepsis. J Biol Chem. Nov. 4, 2005;280(44):36541-4. Epub Aug. 22, 2005.
Almand et al., Increased production of immature myeloid cells in cancer patients: a mechanism of immunosuppression in cancer. J Immunol. Jan. 1, 2001;166(1):678-89.
Bacher et al., The role of macrophage migration inhibitory factor in Alzheimer's disease. Mol Med. Mar. 2010;16(3-4):116-21. doi: 10.2119/molmed.2009.00123. Epub Feb. 28, 2010.
Chen et al., ISO-1, a macrophage migration inhibitory factor antagonist, inhibits airway remodeling in a murine model of chronic asthma. Mol Med. Sep.-Oct. 2010;16(9-10):400-8. doi: 10.2119/molmed.2009.00128. Epub May 14, 2010.
Chesney et al., An essential role for macrophage migration inhibitory factor (MIF) in angiogenesis and the growth of a murine lymphoma. Mol Med. Mar. 1999;5(3):181-91.
Cho et al., Allosteric inhibition of macrophage migration inhibitory factor revealed by ibudilast. Proc Natl Acad Sci U S A. Jun. 22, 2010;107(25):11313-8. doi: 10.1073/pnas.1002716107. Epub Jun. 8, 2010.
Cornella et al., Synthesis of porritoxin. J Org Chem. Mar. 19, 2004;69(6):2191-3.

(Continued)

*Primary Examiner* — Shawquia Jackson
(74) *Attorney, Agent, or Firm* — Wolf, Greenfield & Sacks, P.C.

(57) ABSTRACT

Compounds having an isoindolin-1-one backbone of Formula (I) are disclosed which have utility in treating and/or preventing microbial infections, tumor growth, metastasis and other macrophage migration inhibitory factor (MIF)-modulated pathological conditions. Pharmaceutical compositions and methods and use of compounds of Formula (I) are also disclosed.

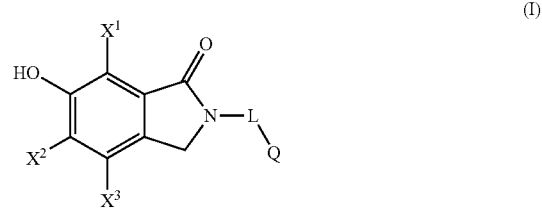

(I)

19 Claims, No Drawings

(56) References Cited

OTHER PUBLICATIONS

Cross et al., Nutrient isothiocyanates covalently modify and inhibit the inflammatory cytokine macrophage migration inhibitory factor (MIF). Biochem J. Oct. 12, 2009;423(3):315-21. doi: 10.1042/BJ20091170.

El Turk et al., An integrative in silico methodology for the identification of modulators of macrophage migration inhibitory factor (MIF) tautomerase activity. Bioorg Med Chem. Jul. 15, 2010;18(14):5425-40. doi: 10.1016/j.bmc.2010.05.010. Epub May 13, 2010.

Garai et al., Macrophage migration inhibitory factor (MIF) tautomerase inhibitors as potential novel anti-inflammatory agents: current developments. Curr Med Chem. 2009;16(9):1091-114.

Gore et al., Macrophage migration inhibitory factor induces B cell survival by activation of a CD74-CD44 receptor complex. J Biol Chem. Feb. 1, 2008;283(5):2784-92. Epub Dec. 4, 2007.

Grieb et al., Macrophage migration inhibitory factor (MIF): a promising biomarker. Drug News Perspect. May 2010;23(4):257-64. doi: 10.1358/dnp.2010.23.4.1453629. Author Manuscript.

Hardcastle et al., Isoindolinone inhibitors of the murine double minute 2 (MDM2)-p53 protein-protein interaction: structure-activity studies leading to improved potency. J Med Chem. Mar. 10, 2011;54(5):1233-43. doi: 10.1021/jm1011929. Epub Feb. 11, 2011.

Hare et al., Optimization of N-benzyl-benzoxazol-2-ones as receptor antagonists of macrophage migration inhibitory factor (MIF). Bioorg Med Chem Lett. Oct. 1, 2010;20(19):5811-4. doi: 10.1016/j.bmcl.2010.07.129. Epub Aug. 3, 2010.

He et al., Increased epithelial and serum expression of macrophage migration inhibitory factor (MIF) in gastric cancer: potential role of MIF in gastric carcinogenesis. Gut. Jun. 2006;55(6):797-802. Epub Feb. 17, 2006.

Jorgensen et al., Benzisothiazolones as modulators of macrophage migration inhibitory factor. Bioorg Med Chem Lett. Aug. 1, 2011;21(15):4545-9. doi: 10.1016/j.bmcl.2011.05.127. Epub Jun. 12, 2011.

Kim et al., A new antioxidant, clitocybin A, from the culture broth of Clitocybe aurantiaca. J Antibiot (Tokyo). Sep. 2008;61(9):573-6. doi: 10.1038/ja.2008.77.

Kithcart et al., A small-molecule inhibitor of macrophage migration inhibitory factor for the treatment of inflammatory disease. FASEB J. Nov. 2010;24(11):4459-66. doi: 10.1096/fj.10-162347. Epub Jul. 12, 2010.

Lee et al., Design, synthesis, and evaluation of isoindolinone-hydroxamic acid derivatives as histone deacetylase (HDAC) inhibitors. Bioorg Med Chem Lett. Sep. 1, 2007;17(17):4895-900. Epub Jun. 13, 2007.

Leng et al., A small-molecule macrophage migration inhibitory factor antagonist protects against glomerulonephritis in lupus-prone NZB/NZW F1 and MRL/lpr mice. J Immunol. Jan. 1, 2011;186(1):527-38. doi: 10.4049/jimmunol.1001767. Epub Nov. 24, 2010.

Leng et al., MIF signal transduction initiated by binding to CD74. J Exp Med. Jun. 2, 2003;197(11):1467-76.

Lubetsky et al., The tautomerase active site of macrophage migration inhibitory factor is a potential target for discovery of novel anti-inflammatory agents. J Biol Chem. Jul. 12, 2002;277(28):24976-82. Epub May 7, 2002.

Madeira et al., MIF induces osteoclast differentiation and contributes to progression of periodontal disease in mice. Microbes Infect. Feb. 2012;14(2):198-206. doi: 10.1016/j.micinf.2011.09.005. Epub Oct. 6, 2011.

Magalhães et al., Macrophage migration inhibitory factor is essential for allergic asthma but not for Th2 differentiation. Eur J Immunol. Apr. 2007;37(4):1097-106.

Martin et al., Macrophage migration inhibitory factor (MIF) plays a critical role in pathogenesis of ultraviolet-B (UVB)-induced nonmelanoma skin cancer (NMSC). FASEB J. Mar. 2009;23(3):720-30. doi: 10.1096/fj.08-119628. Epub Oct. 24, 2008.

McLean et al., Fragment screening of inhibitors for MIF tautomerase reveals a cryptic surface binding site. Bioorg Med Chem Lett. Mar. 15, 2010;20(6):1821-4. doi: 10.1016/j.bmcl.2010.02.009. Epub Feb. 6, 2010.

Meyer-Siegler et al., Inhibition of macrophage migration inhibitory factor or its receptor (CD74) attenuates growth and invasion of DU-145 prostate cancer cells. J Immunol. Dec. 15, 2006;177(12):8730-9.

Mizue et al., Role for macrophage migration inhibitory factor in asthma. Proc Natl Acad Sci U S A. Oct. 4, 2005;102(40):14410-5. Epub Sep. 26, 2005.

Moreau et al., A new synthesis of the phytotoxin porritoxin. Tetrahedron. 2006;62(24):5787-90.

Moreau et al., A new total synthesis of porritoxin. J Org Chem. Apr. 14, 2006;71(8):3303-5.

Ohyama et al., Nonlysine-analog plasminogen modulators promote autoproteolytic generation of plasmin(ogen) fragments with angiostatin-like activity. Eur J Biochem. Feb. 2004;271(4):809-20.

Ostrand-Rosenberg et al., Myeloid-derived suppressor cells: linking inflammation and cancer. J Immunol. Apr. 15, 2009;182(8):4499-506. doi: 10.4049/jimmunol.0802740.

Ren et al., Macrophage migration inhibitory factor: roles in regulating tumor cell migration and expression of angiogenic factors in hepatocellular carcinoma. Int J Cancer. Oct. 20, 2003;107(1):22-9.

Rossi et al., Human circulating eosinophils secrete macrophage migration inhibitory factor (MIF). Potential role in asthma. J Clin Invest. Jun. 15, 1998;101(12):2869-74.

Schulz et al., Inhibiting the HSP90 chaperone destabilizes macrophage migration inhibitory factor and thereby inhibits breast tumor progression. J Exp Med. Feb. 13, 2012;209(2):275-89. doi: 10.1084/jem.20111117. Epub Jan. 23, 2012.

Senter et al., Inhibition of macrophage migration inhibitory factor (MIF) tautomerase and biological activities by acetaminophen metabolites. Proc Natl Acad Sci U S A. Jan. 8, 2002;99(1):144-9. Epub Jan. 2, 2002.

Shah et al., Synthesis and enantiomeric separation of 2-phthalimidino-glutaric acid analogues: potent inhibitors of tumor metastasis. J Med Chem. Aug. 12, 1999;42(16):3014-7.

Shinozuka et al., First total synthesis of sterenins A, C and D. Tetrahedron Letters. 2008;49(10):1619-22.

Simpson et al., Macrophage migration inhibitory factor promotes tumor growth and metastasis by inducing myeloid-derived suppressor cells in the tumor microenvironment. J Immunol. Dec. 15, 2012;189(12):5533-40. doi: 10.4049/jimmunol.1201161. Epub Nov. 2, 2012.

Taylor et al., Null mutation for macrophage migration inhibitory factor (MIF) is associated with less aggressive bladder cancer in mice. BMC Cancer. Jul. 24, 2007;7:135. 8 pages.

Vazquez et al., Novel sesquiterpenoids as tyrosine kinase inhibitors produced by Stachybotrys chortarum. Tetrahedon Letters. 2004;60:2379-85.

Wang et al., New insights into the role and mechanism of macrophage migration inhibitory factor in steroid-resistant patients with systemic lupus erythematosus. Arthritis Res Ther. May 2, 2012;14(3):R103. doi: 10.1186/ar3828. 9 pages.

Weber et al., Structural determinants of MIF functions in CXCR2-mediated inflammatory and atherogenic leukocyte recruitment. Proc Natl Acad Sci U S A. Oct. 21, 2008;105(42):16278-83. doi: 10.1073/pnas.0804017105. Epub Oct. 13, 2008.

Wilson et al., Macrophage migration inhibitory factor promotes intestinal tumorigenesis. Gastroenterology. Nov. 2005;129(5):1485-503.

Winner et al., A novel, macrophage migration inhibitory factor suicide substrate inhibits motility and growth of lung cancer cells. Cancer Res. Sep. 15, 2008;68(18):7253-7. doi: 10.1158/0008-5472.CAN-07-6227.

Yoshihisa et al., Macrophage migration inhibitory factor is essential for eosinophil recruitment in allergen-induced skin inflammation. J Invest Dermatol. Apr. 2011;131(4):925-31. doi: 10.1038/jid.2010.418. Epub Dec. 30, 2010.

(56) References Cited

OTHER PUBLICATIONS

Zea et al., Arginase-producing myeloid suppressor cells in renal cell carcinoma patients: a mechanism of tumor evasion. Cancer Res. Apr. 15, 2005;65(8):3044-8.

* cited by examiner

ISOINDOLIN-1-ONES AS MACROPHAGE MIGRATION INHIBITORY FACTOR (MIF) INHIBITORS

RELATED APPLICATIONS

The present application claims priority under 35 U.S.C. §119(e) to U.S. provisional patent application, U.S. Ser. No. 61/916,988, filed Dec. 17, 2013, the entire contents of which is incorporated herein by reference.

BACKGROUND OF THE INVENTION

Macrophage migration inhibitory factor (MIF) is a cytokine secreted by activated lymphocytes and macrophages that critically regulates inflammation. As a multifunctional protein, MIF is thought to act as a major regulator of inflammation and a central upstream mediator of innate immune responses (Calandra, T., et al., *Nat. Rev. Immunol.* 2003, 3, 791-800), and play an important role in downstream signaling events via its binding with its known receptors CD74, CXCR2 and CXCR4 (Leng, L., et al., *J. Exp. Med.* 2003, 197(11), 1467-76; Gore, Y., et al., *J. Biol. Chem.* 2008, 283, 2784-92; Bernhagen, J., et al., *Nat. Med.* 2007, 13, 587-596; Cho, Y., et al., *Proc. Natl. Acad. Sci. USA* 2010, 107, 11313-8; McLean, L. R., et al., *Bioorg. Med. Chem. Lett.* 2010, 20, 1821-4; Weber, C., et al., *Proc. Natl. Acad. Sci. USA* 2008, 105, 16278-83).

Among cytokines, MIF is unique in that it functions as an enzyme exhibiting tautomerase catalytic activity. Structure analysis demonstrates that MIF exists as a homotrimer with the active site for the tautomerase activity located between two adjacent monomers of the homotrimer (Lubetsky, J. B., et al., *Biochemistry* 1999, 38, 7346-54). MIF catalyzes the tautomerization of D-dopachrome, phenylpyruvate, and certain catecholamines. (S,R)-3-(4-Hydroxyphenyl)-4,5-dihydro-5-isoxazole acetic acid methyl ester (ISO-1), an inhibitor of MIF tautomerase activity, binds to the same position of the active site as does p-hydroxyphenylpyruvic acid (a substrate of MIF), inhibits the binding of MIF to the ectodomain of its receptor CD74, and antagonizes biological activities of MIF (Leng, L., et al., *J. Immunol.* 2011, 186, 527-538; Lubetsky, J. B., et al., *J. Biol. Chem.* 2002, 277, 24976-82). Interestingly, N-acetyl-p-benzoquinone imine (NAPQI), a metabolite of acetaminophen, forms a covalent complex with MIF at its active site to irreversibly inhibit MIF tautomerase activity and biological effects of MIF (Senter, P. D., et al., *Proc. Natl. Acad. Sci. USA* 2002, 99, 144-9). Additionally, other small molecules have been shown to form covalent complexes with MIF and irreversibly inhibit MIF's tautomerase activity (Winner, M., et al., *Cancer Res.* 2008, 68, 7253-7257; Cross, J. V., et al., *Biochem. J.* 2009, 423, 315-321). Because small molecule inhibitors of MIF tautomerase have been reported to antagonize the biological function of MIF, inhibition of MIF's tautomerase activity has been used to screen for drug candidates for treating inflammatory and neoplastic disease (Garai, J., et al., *Curr. Med. Chem.* 2009, 16, 1091-1114; Xu, L., et al., *Drug Discovery Today* 2013, 18, 592-600). Recent studies of the P1G mutation in a mouse breast cancer model suggest that MIF tautomerase activity is an important determinant of tumor growth and metastasis (Simpson, K. D., et al., *J. Immunol.* 2012, 189, 5533-5540). Moreover, small molecule reversible MIF tautomerase inhibitors, by their direct and/or indirect enhancement of CD8+ T-cell immune responses, could surprisingly fill an unmet need for safer and more efficacious agents to treat cancer and other proliferative diseases, prevent metastasis, and also provide safer and more efficacious agents for treating and preventing infections by viruses, plasmodia, fungi, mycobacteria, helminths and other microbes whose clearance is enhanced by a CD8+ T-cell immune response. Additionally, the ability of an anti-MIF antibody or a small molecule MIF inhibitor to reduce airway hyper-responsiveness and airway remodeling in mouse models of asthma suggests that MIF tautomerase inhibitors could also have utility in treating asthma (see e.g. Amano, T., et al., *Inflam. Res.* 2007, 56, 24-31; Chen, P.-F., et al., *Mol. Med.,* 2010, 16, 400-408).

SUMMARY OF THE INVENTION

Disclosed herein are isoindolin-1-one potent reversible inhibitors of MIF tautomerase that can inhibit the activity of MIF when administered (e.g., orally or parenterally) to a subject (e.g., an immune competent mammal) and thereby surprisingly satisfy unmet needs for safer and more efficacious agents for both inhibiting MHC class-II immune responses to treat disorders such as asthma, and for enhancing MHC class-I immune responses to treat cancer and other proliferative diseases, and treat and/or prevent infections by certain microbes (e.g., such as but not limited to viruses, plasmodia, fungi, mycobacteria and helminthes) whose clearance is enhanced by a CD8+ T-cell immune response.

In one aspect, provided is a compound of Formula (I):

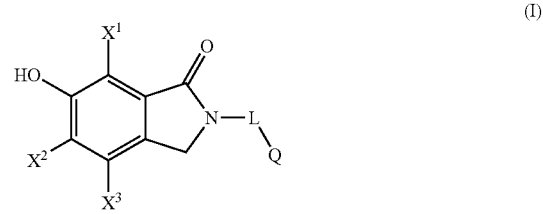

or a pharmaceutically acceptable salt, stereoisomer, or prodrug thereof, wherein $X^1$, $X^2$, $X^3$, L, and Q are as defined herein. In certain embodiments, the compound of Formula (I) is a macrophage migration inhibitory factor (MIF) tautomerase inhibitor.

In another aspect, provided is a pharmaceutical composition comprising a MIF tautomerase inhibitor, as described herein, and a pharmaceutically acceptable excipient.

In yet another aspect, provided is a method of treating a disease or disorder associated with overexpression of MIF tautomerase activity, comprising administering to a subject in need of such treatment an effective amount of a MIF tautomerase inhibitor, as described herein.

In yet another aspect, provided is a method of treating asthma in a subject in need thereof, comprising administering to the subject an effective amount of a MIF tautomerase inhibitor, as described herein.

In yet another aspect, provided is a method of treating a cancer or other proliferative disease (e.g., such as, but not limited to, polycythemia vera, primary myelofibrosis, essential thrombocythemia, idiopathic pulmonary fibrosis, and atherosclerosis) in a subject in need thereof, comprising administering to the subject an effective amount of a MIF tautomerase inhibitor, as described herein.

In yet another aspect, provided is a method of treating a cancer in a subject in need thereof comprising administering to the subject an effective amount of a MIF tautomerase inhibitor as described herein, optionally in combination with at least one antineoplastic agent and/or a therapy (e.g., such as but not limited to x-ray irradiation therapy). In certain embodiments, the cancer is breast cancer.

In yet another aspect, provided is a method of treatment to prevent or suppress metastasis of a cancer in a subject comprising administering to a subject in need of such treatment an effective amount of a MIF tautomerase inhibitor as described herein, optionally in combination with at least one antineoplastic agent and/or a therapy (e.g., such as but not limited to x-ray irradiation therapy). In certain embodiments, the cancer is breast cancer, and the method comprises preventing or suppressing metastatic breast cancer.

In yet another aspect, provided is a method of treatment to prevent or suppress tumor growth in a subject comprising administering to the subject an effective amount of a MIF tautomerase inhibitor as disclosed herein, optionally in combination with at least one antineoplastic agent and/or a therapy (e.g., such as but not limited to x-ray irradiation therapy). In certain embodiments, the tumor growth is breast cancer tumor growth.

In yet another aspect, provided is a method of treating a microbial infection in a subject comprising administering to the subject an effective amount of a MIF tautomerase inhibitor as disclosed herein, optionally in combination with at least one antimicrobial agent.

In yet another aspect, provided is a method of treatment to maintain a microbial infection in a latent state in a subject comprising administering to the subject an effective amount of a MIF tautomerase inhibitor as disclosed herein, optionally in combination with an antimicrobial agent.

In still yet another aspect, provided is a method of vaccination comprising administering to a subject in need of such treatment an effective amount of a MIF tautomerase inhibitor, such as but not limited to one disclosed herein, in combination with an antigen formulation that promotes CD8+ T-cell based immunity in the subject in need thereof.

In still yet another aspect, provided is a method of treating or vaccinating a subject in need thereof with a MIF tautomerase inhibitor or a MIF tautomerase inhibitor augmented vaccine, wherein the subject is treated or vaccinated only if the subject's HLA haplotype matches more closely to the HLA haplotypes of those who previously benefited from the therapy or vaccination than to the HLA haplotypes of those who did not benefit from the therapy or vaccination.

The details of one or more embodiments of the invention are set forth in the Detailed Description below. Other features, objects, and advantages of the invention will be apparent from the Examples and the Claims.

DEFINITIONS

Chemical Definitions

Definitions of specific functional groups and chemical terms are described in more detail below. The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, compounds described herein can be in the form of an individual enantiomer, diastereomer or geometric isomer, or can be in the form of a mixture of stereoisomers, including racemic mixtures and mixtures enriched in one or more stereoisomer. Each of these forms is encompassed by the term "stereoisomers." Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, NY, 1962); and Wilen, S. H. *Tables of Resolving Agents and Optical Resolutions* p. 268 (E. L. Eliel, Ed., Univ. of Notre Dame Press, Notre Dame, Ind. 1972). The invention additionally encompasses compounds as individual isomers substantially free of other isomers, and alternatively, as mixtures of various isomers.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}$F with $^{18}$F, or the replacement of a carbon by a $^{13}$C- or $^{14}$C-enriched carbon are within the scope of the disclosure. Such compounds are useful, for example, as analytical tools or probes in biological assays.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

As used herein, "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), iso-propyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") with one or more substituents. In certain embodiments, the alkyl group is an unsubstituted $C_{1-10}$ alkyl (e.g., —$CH_3$). In certain embodiments, the alkyl group is a substituted $C_{1-10}$ alkyl.

As used herein, "haloalkyl" is a substituted alkyl group as defined herein wherein one or more of the hydrogen atoms are independently replaced by a halogen, e.g., fluoro, bromo, chloro, or iodo. "Perhaloalkyl" is a subset of haloalkyl, and refers to an alkyl group wherein all of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). In some embodiments, all of the haloalkyl hydrogen atoms are replaced with fluoro to provide a perfluoroalkyl group. In some embodiments, all of the haloalkyl hydrogen atoms are replaced with chloro to provide a "perchloroalkyl" group. Examples of haloalkyl groups include —$CF_3$, —$CF_2CF_3$, —$CF_2CF_2CF_3$, —$CCl_3$, —$CFCl_2$, —$CF_2Cl$, and the like.

As used herein, "heteroalkyl" refers to an alkyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("hetero$C_{1-10}$ alkyl"). In some embodiments, a heteroalkyl group is a saturated group having 1 to 9 carbon atoms and 1 or more heteroatoms within the parent chain ("hetero$C_{1-9}$ alkyl"). In some embodiments, a heteroalkyl group is a saturated group having 1 to 8 carbon atoms and 1 or more heteroatoms within the parent chain ("hetero$C_{1-8}$ alkyl"). In some embodiments, a heteroalkyl group is a saturated group having 1 to 7 carbon atoms and 1 or more heteroatoms within the parent chain ("hetero$C_{1-7}$ alkyl"). In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 5 carbon atoms and 1 or 2 heteroatoms within the parent chain ("hetero$C_{1-5}$ alkyl"). In some embodiments, a heteroalkyl group is a saturated group having 1 to 4 carbon atoms and 1 or 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("hetero$C_{1-2}$ alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms within the parent chain ("hetero$C_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted hetero$C_{1-10}$ alkyl. In certain embodiments, the heteroalkyl group is a substituted hetero$C_{1-10}$ alkyl.

As used herein, "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl.

As used herein, "heteroalkenyl" refers to an alkenyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("hetero$C_{2-10}$ alkenyl"). In some embodiments, a heteroalkenyl group has 2 to 9 carbon atoms at least one double bond, and 1 or more heteroatoms within the parent chain ("hetero$C_{2-9}$ alkenyl"). In some embodiments, a heteroalkenyl group has 2 to 8 carbon atoms, at least one double bond, and 1 or more heteroatoms within the parent chain ("hetero$C_{2-8}$ alkenyl"). In some embodiments, a heteroalkenyl group has 2 to 7 carbon atoms, at least one double bond, and 1 or more heteroatoms within the parent chain ("hetero$C_{2-7}$ alkenyl"). In some embodiments, a heteroalkenyl group has 2 to 6 carbon atoms, at least one double bond, and 1 or more heteroatoms within the parent chain ("hetero$C_{2-6}$ alkenyl"). In some embodiments, a heteroalkenyl group has 2 to 5 carbon atoms, at least one double bond, and 1 or 2 heteroatoms within the parent chain ("hetero$C_{2-5}$ alkenyl"). In some embodiments, a heteroalkenyl group has 2 to 4 carbon atoms, at least one double bond, and 1 or 2 heteroatoms within the parent chain ("hetero$C_{2-4}$ alkenyl"). In some embodiments, a heteroalkenyl group has 2 to 3 carbon atoms, at least one double bond, and 1 heteroatom within the parent chain ("hetero$C_{2-3}$ alkenyl"). In some embodiments, a heteroalkenyl group has 2 to 6 carbon atoms, at least one double bond, and 1 or 2 heteroatoms within the parent chain ("hetero$C_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted hetero$C_{2-10}$ alkenyl. In certain embodiments, the heteroalkenyl group is a substituted hetero$C_{2-10}$ alkenyl.

As used herein, "alkynyl" refers to a radical of a straight-chain or branched hydrocarbon group having from 2 to 10 carbon atoms and one or more carbon-carbon triple bonds (e.g., 1, 2, 3, or 4 triple bonds) ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_2$-alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{2-10}$ alkynyl. In certain embodiments, the alkynyl group is a substituted $C_{2-10}$ alkynyl.

As used herein, "heteroalkynyl" refers to an alkynyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("hetero$C_{2-10}$ alkynyl"). In some embodiments, a heteroalkynyl group has 2 to 9 carbon atoms, at least one triple bond, and 1 or more heteroatoms within the parent chain ("hetero$C_{2-9}$ alkynyl"). In some embodiments, a heteroalkynyl group has 2 to 8 carbon atoms, at least one triple bond, and 1 or more heteroatoms within the parent chain ("hetero$C_{2-8}$ alkynyl"). In some embodiments, a heteroalkynyl group has 2 to 7 carbon atoms, at least one triple bond, and 1 or more heteroatoms within the parent chain ("hetero$C_{2-7}$ alkynyl"). In some embodiments, a heteroalkynyl group has 2 to 6 carbon atoms, at least one triple bond, and 1 or more heteroatoms within the parent chain ("hetero$C_{2-6}$ alkynyl"). In some embodiments, a heteroalkynyl group has 2 to 5 carbon atoms, at least one triple bond, and 1 or 2 heteroatoms within the parent chain ("hetero$C_{2-5}$ alkynyl"). In some embodiments, a heteroalkynyl group has 2 to 4 carbon atoms, at least one triple bond, and 1 or 2 heteroatoms within the parent chain ("hetero$C_{2-4}$ alkynyl"). In some embodiments, a heteroalkynyl group has 2 to 3 carbon atoms, at least one triple bond, and 1 heteroatom within the parent chain ("hetero$C_{2-3}$ alkynyl"). In some embodiments, a heteroalkynyl group has 2 to 6 carbon atoms, at least one triple bond, and 1 or 2 heteroatoms within the parent chain ("hetero$C_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted hetero$C_{2-10}$ alkynyl. In certain embodiments, the heteroalkynyl group is a substituted hetero$C_{2-10}$ alkynyl.

As used herein, "carbocyclyl" or "carbocyclic" refers to a radical of a non-aromatic cyclic hydrocarbon group having from 3 to 14 ring carbon atoms ("$C_{3-14}$ carbocyclyl") and zero heteroatoms in the non-aromatic ring system. In some embodiments, a carbocyclyl group has 3 to 10 ring carbon atoms ("$C_{3-10}$ carbocyclyl"). In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 4 to 6 ring carbon atoms ("$C_{4-6}$ carbocyclyl"). In some embodiments, a carbocyclyl group has 5 to 6 ring carbon atoms ("$C_{5-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-14}$ carbocyclyl. In certain embodiments, the carbocyclyl group is a substituted $C_{3-14}$ carbocyclyl.

In some embodiments, "carbocyclyl" is a monocyclic, saturated carbocyclyl group having from 3 to 14 ring carbon atoms ("$C_{3-14}$ cycloalkyl"). In some embodiments, "carbocyclyl" is a monocyclic, saturated carbocyclyl group having from 3 to 12 ring carbon atoms ("$C_{3-12}$ cycloalkyl"). In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_6$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-14}$ cycloalkyl. In certain embodiments, the cycloalkyl group is a substituted $C_{3-14}$ cycloalkyl.

As used herein, "heterocycle" or "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 3 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

As used herein, "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

"Aralkyl" is a subset of "alkyl" and refers to an alkyl group, as defined herein, substituted by an aryl group, as defined herein, wherein the point of attachment is on the alkyl moiety.

As used herein, "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

"Heteroaralkyl" is a subset of "alkyl" and refers to an alkyl group, as defined herein, substituted by a heteroaryl group, as defined herein, wherein the point of attachment is on the alkyl moiety.

As used herein, the term "partially unsaturated" refers to a ring moiety that includes at least one double or triple bond. The term "partially unsaturated" is intended to encompass rings having multiple sites of unsaturation, but is not intended to include aromatic groups (e.g., aryl or heteroaryl moieties) as herein defined.

As used herein, the term "saturated" refers to a ring moiety that does not contain a double or triple bond, i.e., the ring contains all single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

As understood from the above, alkyl, alkenyl, alkynyl, heteroalkyl, heteroalkenyl, heteroalkynyl, carbocyclyl, heterocyclyl, aryl, and heteroaryl groups, as defined herein, are, in certain embodiments, optionally substituted. Optionally substituted refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction.

Unless otherwise indicated, a "substituted" group has a substituent at one or more substitutable positions of the group, and when more than one position in any given structure is substituted, the substituent is either the same or different at each position. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —CH(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$+X, —N(OR$^{ee}$)R$^{ff}$, —SH, —SR$^{ee}$, —SSR$^{ee}$, —C(=O)R$^{ee}$, —C, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{2-6}$ perhaloalkyl, C$_{2-6}$ alkenyl, C$_{2-6}$ alkynyl, heteroC$_{1-6}$ alkyl, heteroC$_{2-6}$ alkenyl, heteroC$_{2-6}$ alkynyl, C$_{3-10}$ carbocyclyl, 3-10 membered heterocyclyl, C$_6$10 aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$ alkenyl, heteroC$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$ alkenyl, heteroC$_{2-6}$ alkynyl, C$_{3-10}$ carbocyclyl, 3-10 membered heterocyclyl, C$_6$10 aryl and 5-10 membered heteroaryl, or two R$^{ff}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$+X, —NH(C$_{1-6}$ alkyl)$_2$+X, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$ alkenyl, hetero$C_{2-6}$ alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein $X^-$ is a counterion.

In certain embodiments, exemplary carbon atom substituents include, but are not limited to, halogen, —CN, —NO$_2$, —OH, —OR$^{aa}$, —N(R$^{bb}$)$_2$, —SH, —SR$^{aa}$, —C(=O)R$^{aa}$, —CO$_2$H, —CHO, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$C$_2$R$^{aa}$, —NR$^{bb}$C(=O)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —C$_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups.

As used herein, the term "halo" or "halogen" refers to fluorine (fluoro, —F), chlorine (chloro, —Cl), bromine (bromo, —Br), or iodine (iodo, —I).

As used herein, a "counterion" is a negatively charged group associated with a positively charged quarternary amine in order to maintain electronic neutrality. Exemplary counterions include halide ions (e.g., F$^-$, Cl$^-$, Br$^-$, I$^-$), NO$_3^-$, ClO$_4^-$, OH$^-$, H$_2$PO$_4^-$, HSO$_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

Nitrogen atoms can be substituted or unsubstituted as valency permits, and include primary, secondary, tertiary, and quarternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{aa}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, the substituent present on the nitrogen atom is an nitrogen protecting group (also referred to herein as an "amino protecting group"). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, $C_{1-10}$ alkyl (e.g., aralkyl, heteroaralkyl), $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)OR$^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), P3-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$, —P(=O)$_2$R$^{aa}$, —P(=O)(R$^{aa}$)$_2$, —P(=O)(OR$^{cc}$)$_2$, —P(=O)$_2$N(R$^{bb}$)$_2$, and —P(=O)(NR$^{bb}$)$_2$, wherein R$^{aa}$, R$^{bb}$, and R$^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, a-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, a-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

These and other exemplary substituents are described in more detail in the Detailed Description, Examples, and claims. The invention is not intended to be limited in any manner by the above exemplary listing of substituents.

Other Definitions

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and $N^+(C_{1-4}\text{ alkyl})_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

A "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or other non-human animals, for example mammals [e.g., primates (e.g., cynomolgus monkeys, rhesus monkeys); commercially relevant mammals such as cattle, pigs, horses, sheep, goats, cats, and/or dogs], birds (e.g., commercially relevant birds such as chickens, ducks, geese, and/or turkeys), reptiles, amphibians, and fish. In certain embodiments, the non-human animal is a mammal. The non-human animal may be a male or female and at any stage of development. A non-human animal may be a transgenic animal.

As used herein, a "prodrug" refers to a compound having groups attached to a nitrogen or oxygen atom which cleave by solvolysis or under physiological conditions to provide a compound of Formula (I). Exemplary cleavable groups attached to a nitrogen atom include, but are not limited to, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, and —P(=O)(NR$^{cc}$)$_2$, wherein R$^{aa}$, R$^{bb}$, and R$^{cc}$ are as defined herein. Exemplary cleavable groups attached to an oxygen atom include, but are not limited to, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —P(=O)$_2$R$^{aa}$, —P(=O)(R$^{aa}$)$_2$, —P(=O)(OR$^{cc}$)$_2$, —P(=O)$_2$N(R$^{bb}$)$_2$, and —P(=O)(NR$^{bb}$)$_2$, wherein R$^{aa}$, R$^{bb}$, and R$^{cc}$ are as defined herein. An exemplary prodrug of Formula (I) includes a compound of the below Formula (Prodrug-I), wherein R$^{XO}$ is a cleavable group attached to oxygen, as defined herein:

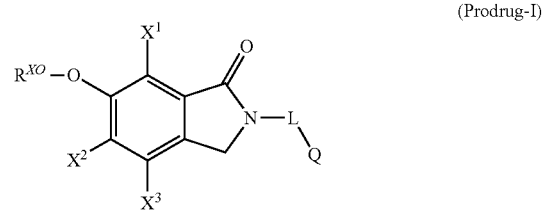

(Prodrug-I)

or a pharmaceutically acceptable salt, or stereoisomer thereof.

As used herein, a "tautomer" refers to a compound in which a hydrogen and double bond have changed position with respect to the other atoms of the molecule. For a pair of tautomers to exist there must be a mechanism for interconversion. Examples of tautomers include keto-enol forms, imine-enamine forms, amide-imino alcohol forms, amidine-aminidine forms, nitroso-oxime forms, thio ketone-enethiol forms, N-nitroso-hydroxyazo forms, nitro-aci-nitro forms, and pyridone-hydroxypyridine forms.

As used herein, a "stereoisomer" refers to an enantiomer or diastereomer of the compound.

The symbol ⌇ if bisecting a bond is used to indicate a point of bond connection or attachment for a substituent.

The symbol ⌇ if used as bond indicates the compound comprises a mixture of stereoisomers.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition ("therapeutic treatment" or "therapeutically treating"), and also contemplates an action that occurs before a subject begins to suffer from the specified disease, disorder or condition ("prophylactic treatment" or "prophylactically treating").

In general, the "effective amount" of a compound refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the age, health, and condition of the subject. An effective amount encompasses therapeutic and prophylactic treatment.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent. For example, in some embodiments, a therapeutically effective amount is an amount sufficient to suppress metastasis of a cancer or tumor growth.

As used herein, and unless otherwise specified, a "prophylactically effective amount" of a compound is an amount sufficient to prevent a disease, disorder or condition, or one or more symptoms associated with the disease, disorder or condition, or prevent its recurrence. A prophylactically effective amount of a compound means an amount of a therapeutic agent, alone or in combination with other agents, which provides a prophylactic benefit in the prevention of the disease, disorder or condition. The term "prophylactically effective amount" can encompass an amount that improves overall prophylaxis or enhances the prophylactic efficacy of another prophylactic agent. For example, in some embodiments, a prophylactically effective amount is an amount sufficient to prevent the metastasis of a cancer or tumor growth.

As used herein "inhibition", "inhibiting", "inhibit" and "inhibitor", and the like, refer to the ability of a compound to reduce, slow, halt or prevent MIF activity in a cell or body fluid relative to vehicle.

The term "$IC_{50}$", as used in this disclosure, shall mean the dose of a particular compound inhibiting MIF activity by 50% relative to a control lacking the compound.

The term "inhibitors" is used interchangeably with the term "antagonists".

DETAILED DESCRIPTION OF CERTAIN EMBODIMENTS OF THE INVENTION

Disclosed herein are isoindolin-1-one potent reversible inhibitors of MIF tautomerase that can block the activity of MIF when administered (e.g., orally or parenterally) and thereby can surprisingly satisfy unmet needs for safer and more efficacious agents for promoting immune responses that inhibit and/or prevent tumor growth and metastasis and eliminate and/or inhibit and/or prevent microbial infections.

Further disclosed herein are uses of MIF tautomerase inhibitors for treatment of MIF-promoted pathologies in a subject in need thereof. MIF-promoted pathologies include, but are not limited to, cancer and other proliferative diseases (e.g., such as, but not limited to, polycythemia vera, primary myelofibrosis, essential thrombocythemia, idiopathic pulmonary fibrosis, and atherosclerosis), tumor growth, metastasis, asthma, microbial infections. Further uses of MIF tautomerase inhibitors include uses in vaccines, e.g., as adjuvants for raising T-cell based immune responses.

Compounds of Formula (I)

As generally described herein, provided are compounds of Formula (I):

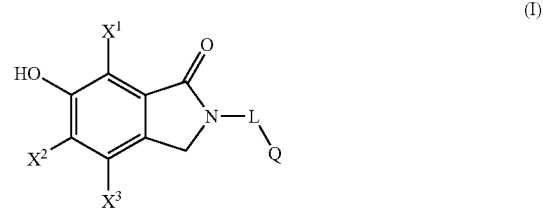

(I)

and pharmaceutically acceptable salts, stereoisomers, and prodrugs thereof, wherein:

$X^1$ is hydrogen, halogen, optionally substituted $C_{1-6}$ alkyl, —$CO_2H$, —$CO_2R^{X1}$, or —$C(=O)NHR^{X1}$, wherein $R^{X1}$ is optionally substituted $C_{1-6}$ alkyl, optionally substituted $C_{3-6}$ carbocyclyl, an oxygen protecting group when attached to oxygen, or a nitrogen protecting group when attached to nitrogen;

$X^2$ is hydrogen, halogen, optionally substituted $C_{1-6}$ alkyl, —$CO_2H$, —$CO_2R^{X2}$, or —$C(=O)NHR^{X2}$, wherein $R^{X2}$ is optionally substituted $C_{1-6}$ alkyl, optionally substituted $C_{3-6}$ carbocyclyl, an oxygen protecting group when attached to oxygen, or a nitrogen protecting group when attached to nitrogen;

$X^3$ is hydrogen, halogen, optionally substituted $C_{1-6}$ alkyl, —OH, —$OR^{X3}$, —$CO_2H$, —$CO_2R^{X3}$, or —$C(=O)NHR^{X3}$, wherein $R^{X3}$ is optionally substituted $C_{1-6}$ alkyl, optionally substituted $C_{3-6}$ carbocyclyl, an oxygen protecting group when attached to oxygen, or a nitrogen protecting group when attached to nitrogen;

L is a linking group selected from the group consisting of:
optionally substituted $C_{3-14}$ carbocyclylene,
-$L^1$-$L^2$-, wherein $L^1$ is optionally substituted $C_{1-6}$ alkylene and attached to the N atom, and $L^2$ is optionally substituted $C_{3-14}$ carbocyclylene and attached to Q,
-$L^3$-$L^4$-, wherein $L^3$ is attached to the N atom and is methylene (—$CH_2$—), ethylene (—$CH_2CH_2$—), or optionally substituted $C_{3-6}$ alkylene, and $L^4$ is optionally substituted $C_{6-14}$ arylene and attached to Q, and
unsubstituted $C_{14}$ alkylene;

Q is:
hydrogen,
—OH (hydroxyl),
$C_{3-12}$ cycloalkyl optionally substituted with substituted or unsubstituted $C_{1-6}$ alkyl, $C_{1-6}$ alkyl optionally substituted with substituted or unsubstituted $C_{3-12}$ cycloalkyl,
aryl optionally substituted with one to three groups independently selected from the group consisting of halogen, carboxyl, hydroxyl, —$OR^Q$, —$CO_2R^Q$, and —$C(=O)NHR^Q$, wherein $R^Q$ is optionally substituted $C_{1-6}$ alkyl, optionally substituted $C_{2-6}$ alkenyl, optionally substituted $C_{2-6}$ alkynyl, optionally substituted $C_{3-6}$ carbocyclyl, an oxygen protecting group when attached to oxygen, or a nitrogen protecting group when attached to nitrogen, or Q is selected from the group consisting of:

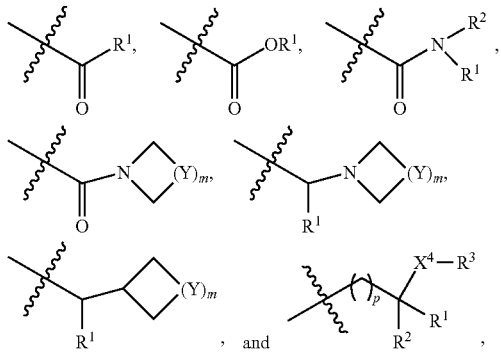

, and wherein $R^1$ and $R^2$ are each independently hydrogen, $C_{3-12}$ cycloalkyl optionally substituted with substituted or unsubstituted $C_{1-6}$ alkyl, or $C_{1-6}$ alkyl optionally substituted with substituted or unsubstituted $C_{3-12}$ cycloalkyl;

each instance of Y is independently, as valency and stability permits, —O—, —S—, —N($R^Y$)—, or —C($R^Y$)$_2$—, wherein m is 2, 3, or 4, and $R^Y$ is hydrogen or $C_{1-6}$ alkyl;

p is 0, 1, 2, 3, or 4;

$X^4$ is oxygen (—O—) or —($R^X$)N—, wherein $R^X$ is selected from the group consisting of:

hydrogen, $C_{3-12}$ cycloalkyl optionally substituted with substituted or unsubstituted $C_{1-6}$ alkyl, $C_{1-6}$ alkyl optionally substituted with substituted or unsubstituted $C_{3-12}$ cycloalkyl, —C(=O)$R^{X5}$, wherein $R^{X5}$ is optionally substituted $C_{1-6}$ alkyl, -$L^{X1}$-CO$_2R^{X6}$, wherein $L^{X1}$ is $C_{1-9}$ alkylene optionally substituted with substituted or unsubstituted alkyl or substituted or unsubstituted aryl, and $R^{X6}$ is hydrogen or optionally substituted $C_{1-6}$ alkyl, and -$L^{X2}$-O—$R^{X7}$, wherein $L^{X2}$ is optionally substituted $C_{1-6}$ alkylene, and $R^{X7}$ is optionally substituted $C_{1-6}$ alkyl;

$R^3$ is:

hydrogen, $C_{3-12}$ cycloalkyl optionally substituted with substituted or unsubstituted $C_{1-6}$ alkyl, $C_{1-6}$ alkyl optionally substituted with substituted or unsubstituted $C_{3-12}$ cycloalkyl, —C(=O)$R^{3A}$ wherein $R^{3A}$ is optionally substituted $C_{1-6}$ alkyl or optionally substituted aryl, $C_{1-6}$ alkyl optionally substituted with a substituted or unsubstituted 5- or 6-membered heterocycle wherein the heterocyclic ring contains from one to four hetero atoms selected from the group consisting of N, S and O, $C_{1-6}$ alkyl optionally substituted with a substituted or unsubstituted heteroaryl ring, aryl optionally substituted with one to three groups selected from the group consisting of halogen, —CO$_2$H, —OH, —OR$^{3B}$, —C(=O)OR$^{3B}$, and —C(=O)NHR$^{3B}$, wherein $R^{3B}$ is optionally substituted $C_{1-6}$ alkyl, or $R^3$ and $R^X$ are joined to form an optionally substituted 5-membered heteroaryl ring, or $R^3$ is a group of formula:

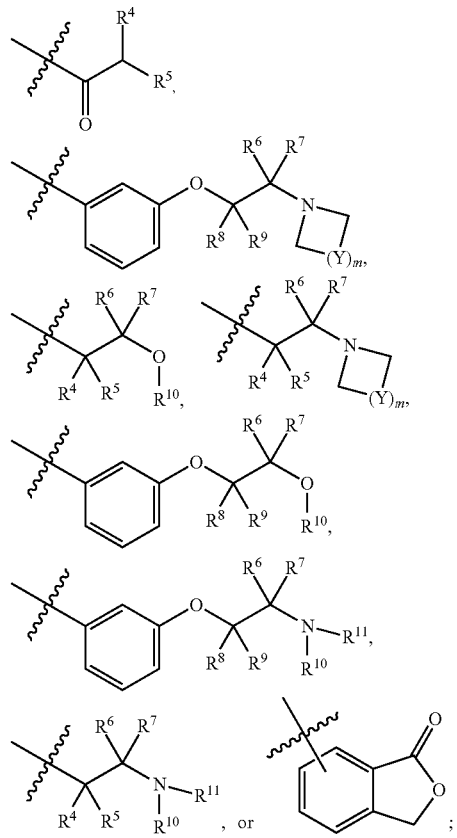

wherein each instance of Y is independently, as valency and stability permits, —O—, —S—, —N($R^Y$)—, or —C($R^Y$)$_2$—, wherein m is 2, 3, or 4, and $R^Y$ is hydrogen or $C_{1-6}$ alkyl;

$R^4$ and $R^5$ are each independently selected from the group consisting of:

hydrogen,

—CO$_2$H,

—C(=O)NHR$^{4A}$, wherein $R^{4A}$ is optionally substituted $C_{1-6}$ alkyl,

—OH,

—OR$^{4A}$, wherein $R^{4A}$ is optionally substituted $C_{1-6}$ alkyl,

-$L^4$-CO$_2R^{4A}$, wherein $L^4$ is $C_{1-9}$ alkylene optionally substituted with substituted or unsubstituted alkyl or substituted or unsubstituted aryl, and $R^{4A}$ is hydrogen or optionally substituted $C_{1-6}$ alkyl, $C_{3-12}$ cycloalkyl optionally substituted with substituted or unsubstituted $C_{1-6}$ alkyl, $C_{1-6}$ alkyl optionally substituted with substituted or unsubstituted $C_{3-12}$ cycloalkyl, 5- or 6-membered optionally substituted heterocyclic ring containing one to four atoms of N, S or O, and aryl unsubstituted or substituted with 1, 2, or 3 groups selected from the group consisting of halogen, —CO$_2$H, —OH, —OR$^{4A}$, —C(=O)OR$^{4A}$, and —C(=O)NHR$^{4A}$, wherein $R^{4A}$ is optionally substituted $C_{1-6}$ alkyl;

$R^6$, $R^7$, $R^8$, and $R^9$ are each independently selected from the group consisting of:

hydrogen, $C_{3-12}$ cycloalkyl optionally substituted with substituted or unsubstituted $C_{1-6}$ alkyl, $C_{1-6}$ alkyl optionally substituted with substituted or unsubstituted $C_{3-12}$ cycloalkyl, -$L^6$-$CO_2R^{6A}$, wherein $L^6$ is absent or $C_{1-9}$ alkylene optionally substituted with substituted or unsubstituted alkyl or substituted or unsubstituted aryl, and $R^{6A}$ is hydrogen or optionally substituted $C_{1-6}$ alkyl, -$L^6$-C(=O)NHR$^{6A}$, wherein $L^6$ is absent or $C_{1-9}$ alkylene optionally substituted with substituted or unsubstituted alkyl or substituted or unsubstituted aryl, and $R^{6A}$ is hydrogen or optionally substituted $C_{1-6}$ alkyl, 5- or 6-membered optionally substituted heterocyclic ring containing one to four atoms of N, S or O, and aryl unsubstituted or substituted with 1, 2, or 3 groups selected from the group consisting of halogen, —$CO_2H$, —OH, —$OR^{6A}$, —C(=O)$OR^{6A}$, and —C(=O)NHR$^{6A}$, wherein $R^{6A}$ is optionally substituted $C_{1-6}$ alkyl;

and $R^{10}$ and $R^{11}$ are each independently selected from the group consisting of:

hydrogen, $C_{3-12}$ cycloalkyl optionally substituted with substituted or unsubstituted $C_{1-6}$ alkyl, $C_{1-6}$ alkyl optionally substituted with substituted or unsubstituted $C_{3-12}$ cycloalkyl, —C(=O)$R^{10A}$, wherein $R^{10A}$ is optionally substituted $C_{1-6}$ alkyl, -$L^{10}$-$CO_2R^{10B}$, wherein $L^{10}$ is $C_{1-9}$ alkylene optionally substituted with substituted or unsubstituted alkyl or substituted or unsubstituted aryl, and $R^{10B}$ is hydrogen or optionally substituted $C_{1-6}$ alkyl, and -$L^{11}$-O—$R^{10A}$, wherein L is optionally substituted $C_{1-6}$ alkylene, and $R^{10A}$ is optionally substituted $C_{1-6}$ alkyl;

provided when L is unsubstituted $C_{1-6}$ alkylene, then Q is:

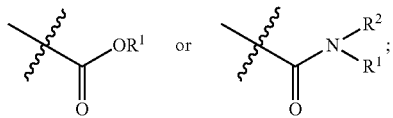

and provided when L is:

optionally substituted $C_{3-14}$ carbocyclylene,

-$L^1$-$L^2$-, wherein $L^1$ is optionally substituted $C_{1-6}$ alkylene and attached to isoindolin-1-one unit, $L^2$ is optionally substituted $C_{3-14}$ carbocyclylene and attached to Q, or -$L^3$-$L^4$-, wherein $L^3$ is attached to the N atom and is methylene (—$CH_2$—), ethylene (—$CH_2CH_2$—), or optionally substituted $C_{3-6}$ alkylene, $L^4$ is optionally substituted $C_{6-14}$ arylene and attached to Q;

then Q is:

hydrogen,

—OH (hydroxyl), $C_{3-12}$ cycloalkyl optionally substituted with substituted or unsubstituted $C_{1-6}$ alkyl, $C_{1-6}$ alkyl optionally substituted with substituted or unsubstituted $C_{3-12}$ cycloalkyl, aryl optionally substituted with one to three groups independently selected from the group consisting of halogen, carboxyl, hydroxyl, —$OR^Q$, —$CO_2R^Q$, and —C(=O)NHR$^Q$, wherein $R^Q$ is optionally substituted $C_{1-6}$ alkyl, optionally substituted $C_{2-6}$ alkenyl, optionally substituted $C_{2-6}$ alkynyl, optionally substituted $C_{3-6}$ carbocyclyl, an oxygen protecting group when attached to oxygen, or a nitrogen protecting group when attached to nitrogen, or Q is selected from the group consisting of:

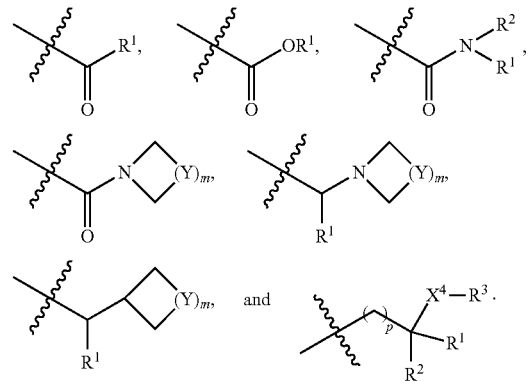

In certain embodiments, at least one of $X^1$, $X^2$ or $X^3$ is hydrogen. In certain embodiments, at least two of $X^1$, $X^2$ or $X^3$ is hydrogen. In certain embodiments, all three of $X^1$, $X^2$ or $X^3$ is hydrogen.

In certain embodiments, at least one of $X^1$, $X^2$ or $X^3$ is halogen (e.g., fluoro or chloro). In certain embodiments, at least two of $X^1$, $X^2$ or $X^3$ is halogen (e.g., fluoro or chloro). In certain embodiments, all three of $X^1$, $X^2$ or $X^3$ is halogen (e.g., fluoro or chloro).

In certain embodiments, $X^1$ is halogen (e.g., fluoro or chloro) and $X^2$ and $X^3$ are each hydrogen. In certain embodiments, $X^2$ is halogen (e.g., fluoro or chloro) and $X^1$ and $X^3$ are each hydrogen. In certain embodiments, $X^3$ is halogen (e.g., fluoro or chloro) and $X^1$ and $X^2$ are each hydrogen. In certain embodiments, $X^3$ and $X^2$ are halogen (e.g., fluoro or chloro) and $X^3$ is hydrogen. In certain embodiments, $X^1$ and $X^3$ are halogen (e.g., fluoro or chloro) and $X^2$ is hydrogen. In certain embodiments, $X^2$ and $X^3$ are halogen (e.g., fluoro or chloro) and $X^1$ is hydrogen.

In certain embodiments, a compound of Formula (I) is a compound of any one of the following Formula:

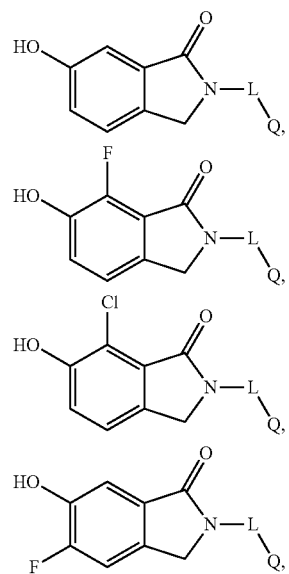

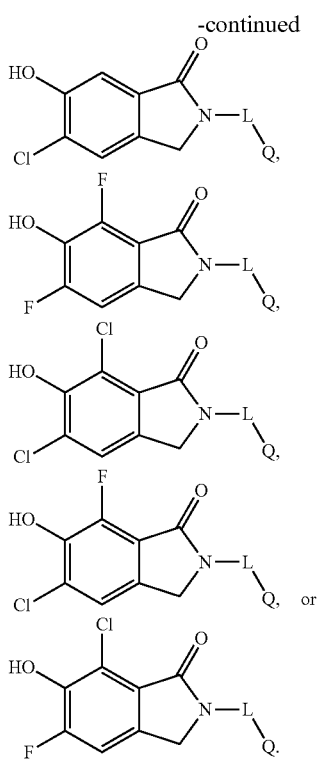

In certain embodiments, a compound of Formula (I) is a compound of Formula (I-a):

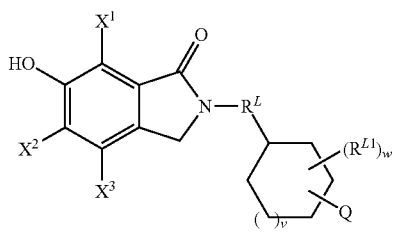

(I-a)

or a pharmaceutically acceptable salt, stereoisomer, or prodrug thereof, wherein $R^L$ is absent or is $L^1$, wherein $L^1$ is an optionally substituted $C_{1-4}$ alkylene (e.g., optionally substituted $C_1$, $C_2$, $C_3$, $C_4$, $C_5$, or $C_6$ alkylene); $R^{L1}$ is hydrogen, halogen, or optionally substituted alkyl; w is 0, 1, or 2; v is 1 or 2; and Q is as defined herein.

In certain embodiments, a compound of Formula (I) is a compound of Formula (I-b):

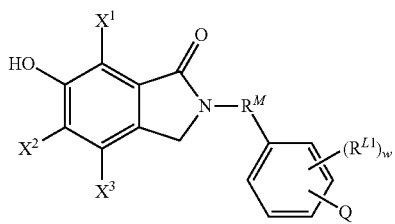

(I-b)

or a pharmaceutically acceptable salt, stereoisomer, or prodrug thereof, wherein $R^M$ is $L^3$ wherein $L^3$ is methylene (—CH$_2$—), ethylene (—CH$_2$CH$_2$—), or optionally substituted $C_{3-4}$ alkylene; $R^{L1}$ is hydrogen, halogen, or optionally substituted alkyl; w is 0, 1, or 2; and Q is as defined herein.

In certain embodiments, L is a linking group selected from the group consisting of:

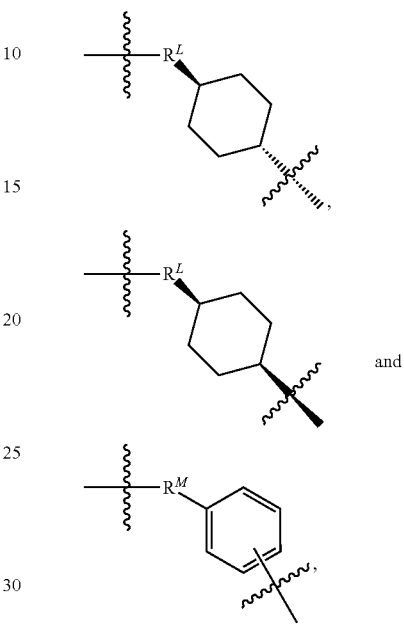

and wherein $R^L$ is absent or is $L^1$, wherein $L^1$ is an optionally substituted $C_{1-4}$ alkylene; $R^M$ is $L^3$ and $L^3$ is methylene (—CH$_2$—), ethylene (—CH$_2$CH$_2$—), or optionally substituted $C_{3-4}$ alkylene; the left sides of the L groups are attached to isoindolin-1-one unit, and the right sides of the L groups are attached to Q.

In certain embodiments, $X^1$ and $X^2$ are each independently hydrogen, fluoro, or chloro; $X^3$ is hydrogen; L is

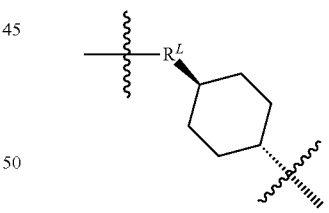

wherein $R^L$ is $L^1$, wherein $L^1$ is methylene, the left side of L is attached to isoindolin-1-one unit, and the right side of L is attached to Q; and Q is

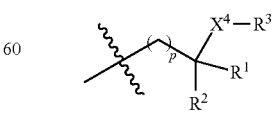

wherein p is 0; $X^4$ is —O—; $R^1$ and $R^2$ are each independently hydrogen or $C_{1-6}$ alkyl optionally substituted with substituted or unsubstituted $C_{3-12}$ cycloalkyl; $R^3$ is

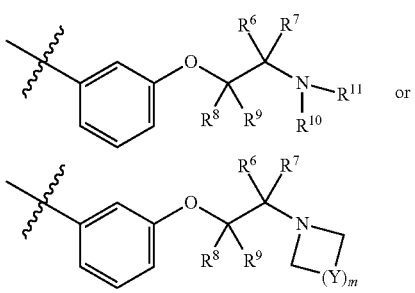

wherein $R^6$ is selected from the group consisting of hydrogen, -$L^6$-$CO_2R^{6A}$, and -$L^6$-C(=O)NH$R^{6A}$, wherein $L^6$ is absent or $C_{1-9}$ alkylene optionally substituted with substituted or unsubstituted alkyl or substituted or unsubstituted aryl, and $R^{6A}$ is hydrogen or optionally substituted $C_{1-6}$ alkyl; $R^7$, $R^8$ and $R^9$ are each independently hydrogen or $C_{1-6}$ alkyl optionally substituted with substituted or unsubstituted $C_{3-12}$ cycloalkyl; $R^{10}$ and $R^{11}$ are each independently hydrogen, $C_{1-6}$ alkyl, or —C(=O)$R^{10A}$, wherein $R^{10A}$ is optionally substituted $C_{1-6}$ alkyl; and Y is independently, as valency and stability permits, —O—, —S—, —N($R^Y$)—, or —C($R^Y$)$_2$—, wherein m is 2, 3, or 4, and $R^Y$ is hydrogen or $C_{1-6}$ alkyl.

In certain embodiments, $X^1$ and $X^2$ are each independently hydrogen, fluoro, or chloro; $X^3$ is hydrogen; L is

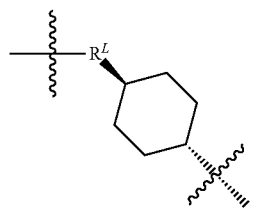

wherein $R^L$ is $L^1$, wherein $L^1$ is methylene, the left side of L is attached to isoindolin-1-one unit, and the right side of L is attached to Q; and Q is

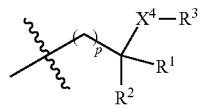

wherein p is 0; $X^4$ is —O—; $R^1$ and $R^2$ are each independently hydrogen or $C_{1-6}$ alkyl optionally substituted with substituted or unsubstituted $C_{3-12}$ cycloalkyl; $R^3$ is hydrogen, $C_{3-12}$ cycloalkyl optionally substituted with substituted or unsubstituted $C_{1-6}$ alkyl, $C_{1-6}$ alkyl optionally substituted with substituted or unsubstituted $C_{3-12}$ cycloalkyl, —C(=O)$R^{3A}$ wherein $R^{3A}$ is optionally substituted $C_{1-6}$ alkyl or optionally substituted aryl, or

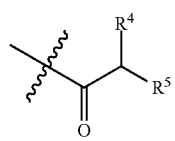

wherein $R^4$ and $R^5$ are each independently hydrogen, —OH, —O$R^{4A}$ wherein $R^{4A}$ is optionally substituted $C_{1-6}$ alkyl, $C_{1-6}$ alkyl optionally substituted with substituted or unsubstituted $C_{3-12}$ cycloalkyl, $C_{3-12}$ cycloalkyl optionally substituted with substituted or unsubstituted $C_{1-6}$ alkyl, or -$L^4$-$CO_2R^{4A}$ wherein $L^4$ is $C_{1-6}$ alkylene optionally substituted with substituted or unsubstituted alkyl or substituted or unsubstituted aryl and $R^{4A}$ is hydrogen or optionally substituted $C_{1-6}$ alkyl.

In certain embodiments, $X^1$ and $X^2$ are each independently hydrogen, fluoro, or chloro; $X^3$ is hydrogen; L is

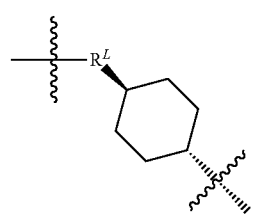

wherein $R^L$ is $L^1$, wherein $L^1$ is methylene, the left side of L is attached to isoindolin-1-one unit, and the right side of L is attached to Q; Q is

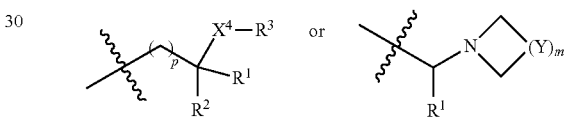

wherein p is 0; $X^4$ is —($R^X$)N— wherein $R^X$ is hydrogen, $C_{3-12}$ cycloalkyl optionally substituted with substituted or unsubstituted $C_{1-6}$ alkyl, $C_{1-6}$ alkyl optionally substituted with substituted or unsubstituted $C_{3-12}$ cycloalkyl, —C(=O)$R^{X5}$ wherein $R^{X5}$ is optionally substituted $C_{1-6}$ alkyl, -$L^{X1}$-$CO_2R^{X6}$ wherein $L^{X1}$ is $C_{1-9}$ alkylene optionally substituted with substituted or unsubstituted alkyl or substituted or unsubstituted aryl, and $R^{X6}$ is hydrogen or optionally substituted $C_{1-6}$ alkyl, or -$L^{X2}$-O—$R^{X7}$ wherein $L^{X2}$ is optionally substituted $C_{1-6}$ alkylene and $R^{X7}$ is optionally substituted $C_{1-6}$ alkyl; $R^1$ and $R^2$ are each independently hydrogen or $C_{1-6}$ alkyl optionally substituted with substituted or unsubstituted $C_{3-12}$ cycloalkyl; Y is independently, as valency and stability permits, —O—, —S—, —N($R^Y$)—, or —C($R^Y$)$_2$—, wherein m is 2, 3, or 4, and $R^Y$ is hydrogen or $C_{1-6}$ alkyl; and $R^3$ is hydrogen, optionally substituted $C_{1-6}$ alkyl or

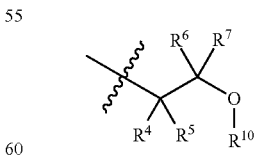

wherein $R^4$, $R^5$, $R^6$, $R^7$ and $R^{10}$ are each independently hydrogen or $C_{1-6}$ alkyl optionally substituted with substituted or unsubstituted $C_{3-12}$ cycloalkyl.

In certain embodiments, $X^1$ and $X^2$ are each independently hydrogen, fluoro, or chloro; $X^3$ is hydrogen; L is

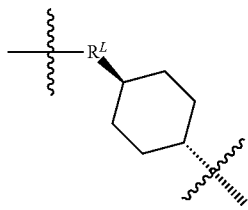

wherein $R^L$ is $L^1$, wherein $L^1$ is methylene, the left side of L is attached to isoindolin-1-one unit, and the right side of L is attached to Q; and Q is

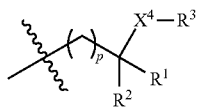

wherein p is 0; $X^4$ is —O—; $R^1$ and $R^2$ are each independently hydrogen or $C_{1-6}$ alkyl optionally substituted with substituted or unsubstituted $C_{3-12}$ cycloalkyl; $R^3$ is

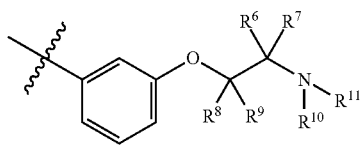

wherein $R^6$ is hydrogen or -$L^6$-$CO_2R^{6A}$, wherein $L^6$ is absent or $C_{1-9}$ alkylene optionally substituted with substituted or unsubstituted alkyl or substituted or unsubstituted aryl, and $R^{6A}$ is hydrogen; $R^7$, $R^8$, and $R^9$ are each independently hydrogen or $C_{1-6}$ alkyl optionally substituted with substituted or unsubstituted $C_{3-12}$ cycloalkyl; $R^{10}$ and $R^{11}$ are each independently hydrogen, —C(=O)$R^{10A}$ wherein $R^{10A}$ is optionally substituted $C_{1-6}$ alkyl, or $C_{1-6}$ alkyl optionally substituted with substituted or unsubstituted $C_{3-12}$ cycloalkyl.

In certain embodiments, $X^1$ and $X^2$ are each independently hydrogen, fluoro, or chloro; X is hydrogen; L is

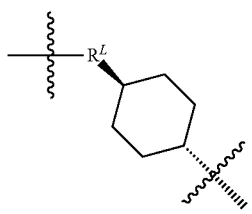

wherein $R^L$ is $L^1$, wherein $L^1$ is methylene, the left side of L is attached to isoindolin-1-one unit, and the right side of L is attached to Q; Q is

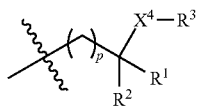

wherein p is 0; $X^4$ is —O—; $R^1$, $R^2$ and $R^3$ are each independently hydrogen or $C_{1-6}$ alkyl optionally substituted with substituted or unsubstituted $C_{3-12}$ cycloalkyl.

In certain embodiments, $X^1$ and $X^2$ are each independently hydrogen, fluoro, or chloro; $X^3$ is hydrogen; L is

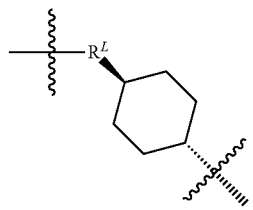

wherein $R^L$ is $L^1$, wherein $L^1$ is methylene, the left side of L is attached to isoindolin-1-one unit, and the right side of L is attached to Q; Q is

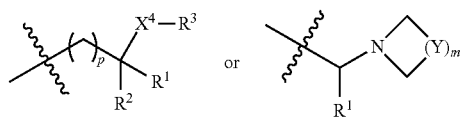

wherein p is 0; $X^4$ is —($R^X$)N— wherein $R^X$ is hydrogen or -$L^{X1}$-$CO_2R^{X6}$, wherein $L^{X1}$ is $C_{1-6}$ alkylene optionally substituted with substituted or unsubstituted alkyl or substituted or unsubstituted aryl, and $R^{X6}$ is hydrogen; $R^1$ and $R^2$ are each independently hydrogen or $C_{1-6}$ alkyl optionally substituted with substituted or unsubstituted $C_{3-12}$ cycloalkyl; Y is independently, as valency and stability permits, —O—, —S—, —N($R^Y$)—, or —C($R^Y$)$_2$—, wherein m is 2, 3, or 4, and $R^Y$ is hydrogen or $C_{1-6}$ alkyl; $R^3$ is hydrogen or $C_{1-6}$ alkyl optionally substituted with substituted or unsubstituted $C_{3-12}$ cycloalkyl.

In certain embodiments, $X^1$ and $X^2$ are each independently hydrogen, fluoro, or chloro; $X^3$ is hydrogen; L is

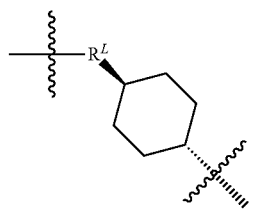

wherein $R^L$ is $L^1$, wherein $L^1$ is methylene, the left side of L is attached to isoindolin-1-one unit, and the right side of L is attached to Q; and Q is

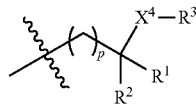

wherein p is 0; $X^4$ is —($R^X$)N— wherein $R^X$ is -$L^{X1}$-$CO_2R^{X6}$, wherein $L^{X1}$ is $C_{1-6}$ alkylene optionally substituted with substituted or unsubstituted alkyl or substituted or unsubstituted aryl, and $R^{X6}$ is hydrogen; and $R^1$, $R^2$, and $R^3$ are each independently hydrogen or methyl.

In certain embodiments, $X^1$ and $X^2$ are each independently hydrogen or fluoro; $X^3$ is hydrogen; L is

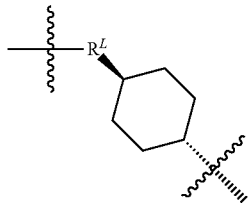

wherein $R^L$ is $L^1$, wherein $L^1$ is methylene, the left side of L is attached to isoindolin-1-one unit, and the right side of L is attached to Q; and Q is

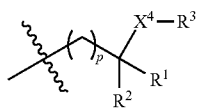

wherein p is 0; $X^4$ is —$(R^X)$N— wherein $R^X$ is hydrogen or $C_{1-6}$ alkyl; $R^3$ is hydrogen or $C_{1-6}$ alkyl; $R^1$ and $R^2$ are each independently hydrogen or methyl.

In certain embodiments, $X^1$ and $X^2$ are each independently hydrogen or chloro; $X^3$ is hydrogen; L is

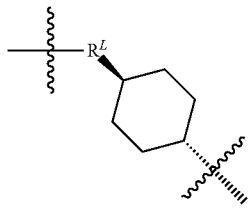

wherein $R^L$ is $L^1$, wherein $L^1$ is methylene, the left side of L is attached to isoindolin-1-one unit, and the right side of L is attached to Q; and Q is

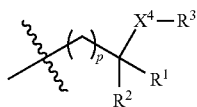

wherein p is 0; $X^4$ is —$(R^X)$N— wherein $R^X$ is hydrogen or $C_{1-6}$ alkyl; $R^3$ is hydrogen or $C_{1-6}$ alkyl; $R^1$ and $R^2$ are each independently hydrogen or methyl.

In certain embodiments, $X^1$ and $X^2$ are each independently fluoro or chloro; $X^3$ is hydrogen; L is

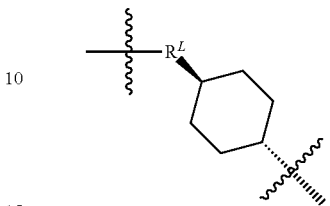

wherein $R^L$ is $L^1$, wherein $L^1$ is methylene, the left side of L is attached to isoindolin-1-one unit, and the right side of L is attached to Q; and Q is

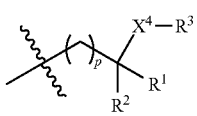

wherein p is 0; $X^4$ is —$(R^X)$N— wherein $R^X$ is hydrogen or $C_{1-6}$ alkyl; $R^3$ is hydrogen or $C_{1-6}$ alkyl; $R^1$ and $R^2$ are each independently hydrogen or methyl.

In certain embodiments, wherein Q is

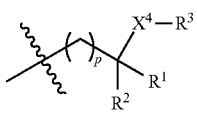

$R^2$ and X is —$(R^X)$N—, $R^3$ and $R^X$ are joined to form an optionally substituted 5-membered heteroaryl ring, e.g., an optionally substituted imidazole ring.

Exemplary compounds of Formula (I), and pharmaceutically acceptable salts, stereoisomers, and prodrugs thereof, are provided herein. For example, in certain embodiments, a compound of Formula (I) is a compound, or a pharmaceutically acceptable salt, stereoisomer, or prodrug thereof, as provided in Table 1, below; wherein the designated relative potency of MIF tautomerase inhibitors is based on the $IC_{50}$ as determined by the method described in Biochemical Assay of the Examples as follows: A, $IC_{50}<1$ μM; B, $1$ μM$\leq IC_{50}<5$ μM; C, $5$ μM$\leq IC_{50}<10$ μM; D, $10$ μM$\leq IC_{50}<50$ μM; E, $50$ μM$\leq IC_{50}<200$ μM.

TABLE 1

Exemplary Isoindolin-1-ones

| Compound | $IC_{50}$ |
|---|---|
| 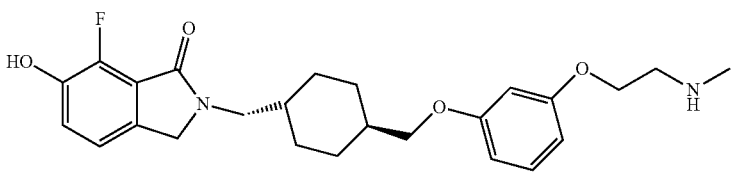 | A |

TABLE 1-continued

Exemplary Isoindolin-1-ones

| Compound | IC$_{50}$ |
|---|---|
| (structure) | A |
| (structure) | A |
| (structure) | A |
| (structure) | A |
| (structure) | A |
| (structure) | A |
| (structure) | A |
| (structure) | A |

TABLE 1-continued

Exemplary Isoindolin-1-ones

| Compound | IC$_{50}$ |
|---|---|
| | A |
| | A |
| | A |
| | A |
| | A |
| | A |
| | A |
| | A |

TABLE 1-continued

Exemplary Isoindolin-1-ones

| Compound | IC$_{50}$ |
|---|---|
| (structure) | |
| (structure) | A |
| (structure) | A |
| (structure) | A |
| (structure) | A |
| (structure) | A |
| (structure) | A |
| (structure) | A |
| (structure) R/S or S/R = 81/19 | A |

TABLE 1-continued

Exemplary Isoindolin-1-ones

| Compound | IC$_{50}$ |
|---|---|
| (structure: 5-fluoro-6-hydroxy-isoindolin-1-one with N-CH2-cyclohexyl-CH(CH3)-O-(3-fluorophenyl); R/S or S/R = 19/81) | A |
| (structure: 6-hydroxy-isoindolin-1-one with N-CH2-cyclohexyl-CH(CH2CH3)-O-(3-fluorophenyl)) | A |
| (structure: 5-fluoro-6-hydroxy-isoindolin-1-one with N-CH2-cyclohexyl-CH(CH3)-O-(3-fluorophenyl)) | A |
| (structure: 7-fluoro-6-hydroxy-isoindolin-1-one with N-CH2-cyclohexyl-CH(CH3)-O-(3-fluorophenyl)) | A |
| (structure: 7-fluoro-6-hydroxy-isoindolin-1-one with N-CH2-cyclohexyl-CH2-O-(3-fluorophenyl)) | A |
| (structure: 6-hydroxy-isoindolin-1-one with N-CH2-cyclohexyl-CH(CH3)-O-(3-fluorophenyl)) | A |
| (structure: 6-hydroxy-isoindolin-1-one with N-CH2-cyclohexyl-CH2-O-(3-fluorophenyl)) | A |
| (structure: 6-hydroxy-isoindolin-1-one with N-CH2-cyclohexyl-CH2-O-(2-fluorophenyl)) | A |
| (structure: 6-hydroxy-isoindolin-1-one with N-CH2-cyclohexyl-CH2-O-(4-fluorophenyl)) | A |

TABLE 1-continued

Exemplary Isoindolin-1-ones

| Compound | IC$_{50}$ |
|---|---|
| | A |
| | A |
| | A |
| | A |
| | A |
| | A |
| | A |

TABLE 1-continued

Exemplary Isoindolin-1-ones

| Compound | IC$_{50}$ |
|---|---|
| (structure) | A |
| (structure) | A |
| (structure) | A |
| (structure) | A |
| (structure) | A |
| (structure) | A |
| (structure) | A |
| (structure) | A |
| (structure) | A |

TABLE 1-continued

Exemplary Isoindolin-1-ones

| Compound | IC$_{50}$ |
|---|---|
| (structure) | A |
| (structure) | A |
| (structure) | A |
| (structure) | A |
| (structure) | A |
| (structure) | A |
| (structure) | A |
| (structure) | A |
| (structure) | A |

TABLE 1-continued

Exemplary Isoindolin-1-ones

| Compound | IC$_{50}$ |
|---|---|
| (structure) | A |
| (structure) | A |
| (structure) dr = 72/28 | A |
| (structure) dr = 23/77 | A |
| (structure) dr = 56/44 | A |
| (structure) dr = 83/17 | A |
| (structure) dr = 2/98 | A |

TABLE 1-continued

Exemplary Isoindolin-1-ones

| Compound | IC$_{50}$ |
|---|---|
| [structure: 4-fluoro-5-hydroxy-isoindolin-1-one linked via CH$_2$-cyclohexyl-CH(CH$_3$)-NH to leucine-COOH]<br>dr = 94/6 | A |
| [structure: 4-fluoro-5-hydroxy-isoindolin-1-one linked via CH$_2$-cyclohexyl-CH(CH$_3$)-NH to serine-COOH]<br>dr = 2/98 | A |
| [structure: 4-fluoro-5-hydroxy-isoindolin-1-one linked via CH$_2$-cyclohexyl-CH(CH$_3$)-NH to valine-COOMe]<br>dr = 98/2 | A |
| [structure: 4-fluoro-5-hydroxy-isoindolin-1-one linked via CH$_2$-cyclohexyl-CH(CH$_3$)-NH to leucine-COOH]<br>dr = 6/94 | A |
| [structure: 4-fluoro-5-hydroxy-isoindolin-1-one linked via CH$_2$-cyclohexyl-CH(CH$_3$)-NH to valine-COOH]<br>dr = 98/2 | A |
| [structure: 4-fluoro-5-hydroxy-isoindolin-1-one linked via CH$_2$-cyclohexyl-CH(CH$_3$)-NH to valine-COOMe]<br>dr = 22/78 | A |

TABLE 1-continued

Exemplary Isoindolin-1-ones

| Compound | IC$_{50}$ |
|---|---|
| dr = 19/81 | A |
| dr = 22/78 | A |
| dr = 100/0 | A |
| dr = 10/90 | A |
| dr = 100/0 | A |
| dr = 10/90 | A |

TABLE 1-continued

Exemplary Isoindolin-1-ones

| Compound | IC$_{50}$ |
|---|---|
| dr = 73/27 | A |
| dr = 100/0 | A |
| dr = 100/0 | A |
| dr = 10/90 | A |
| | A |
| | A |
| | A |

TABLE 1-continued

Exemplary Isoindolin-1-ones

| Compound | IC$_{50}$ |
|---|---|
| (structure) | A |
| (structure) | A |
| (structure) | A |
| (structure) | A |
| (structure) | A |
| (structure) | A |
| (structure) | A |
| (structure) | A |

TABLE 1-continued

Exemplary Isoindolin-1-ones

| Compound | IC$_{50}$ |
|---|---|
| | A |
| | A |
| | A |
| | B |
| | B |
| | B |
| | B |
| | B |
| cis/trans = 72/28 | |

TABLE 1-continued

Exemplary Isoindolin-1-ones

| Compound | IC$_{50}$ |
|---|---|
| (structure; cis/trans = 43/57) | B |
| (structure) | B |
| (structure) | B |
| (structure) | B |
| (structure) | B |
| (structure) | B |
| (structure) | B |
| (structure) | B |
| (structure) | B |
| (structure) | B |

TABLE 1-continued
Exemplary Isoindolin-1-ones
| Compound | IC$_{50}$ |
|---|---|
| 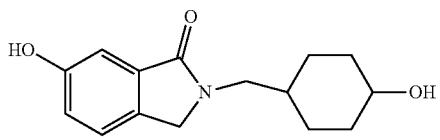 trans/cis = 64/36 | B |
| 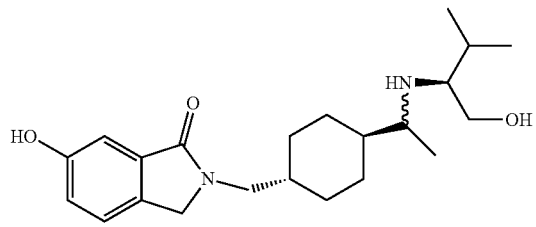 dr = 98/2 | B |
| 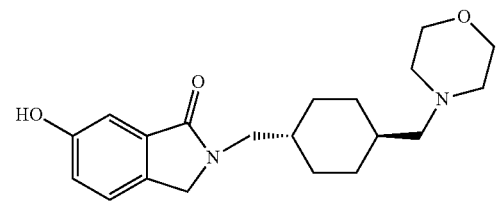 [SMILES: O=C1c2cc(O)ccc2CN1C[C@H]1CC[C@H](CN2CCOCC2)CC1] | B |
| 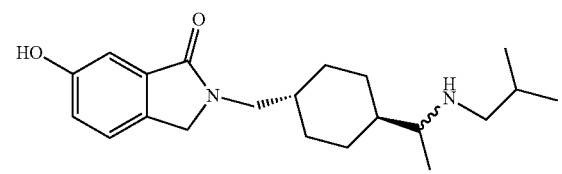 [SMILES: CC(C)CNC(C)[C@H]1CC[C@H](CN2Cc3ccc(O)cc3C2=O)CC1] | B |
| 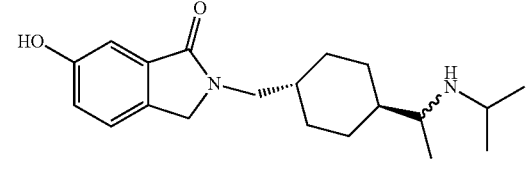 [SMILES: CC(C)NC(C)[C@H]1CC[C@H](CN2Cc3ccc(O)cc3C2=O)CC1] | B |
| 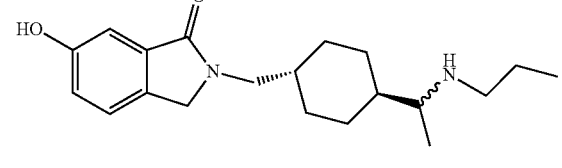 | B |
| 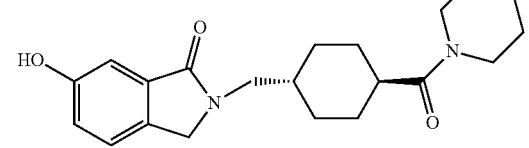 | B |

TABLE 1-continued

Exemplary Isoindolin-1-ones

| Compound | IC$_{50}$ |
|---|---|
| (structure: 7-F, 6-HO, 5-Cl isoindolin-1-one N-CH2-cyclohexyl-CH(NH2)CH3, HCl) | B |
| (structure: 7-F, 6-HO, 5-F isoindolin-1-one N-CH2-cyclohexyl-CH(NH2)CH3) | B |
| (structure: 6-HO isoindolin-1-one N-CH2-cyclohexyl-CH(NH2)CH3) | B |
| (structure: 7-F, 6-HO isoindolin-1-one N-CH2-cyclohexyl-CH2NH2) | B |
| (structure: 6-HO isoindolin-1-one N-CH2-cycloheptyl) | B |
| (structure: 6-HO isoindolin-1-one N-CH2-cyclohexyl) | B |
| (structure: 6-HO isoindolin-1-one N-cyclohexyl-CH3) | B |
| (structure: 6-HO isoindolin-1-one N-(CH2)4-C(O)OMe) | B |
| (structure: 6-HO isoindolin-1-one N-CH2-cyclohexyl-C(O)O-cyclopentyl) | C |

TABLE 1-continued

Exemplary Isoindolin-1-ones

| Compound | IC$_{50}$ |
|---|---|
| ![structure] | C |
| ![structure] | C |
| ![structure] | C |
| ![structure] | C |
| ![structure] | C |
| ![structure] | C |
| ![structure] | C |
| ![structure] | C |
| ![structure] | D |

TABLE 1-continued

Exemplary Isoindolin-1-ones

| Compound | IC$_{50}$ |
|---|---|
| (structure) | D |
| (structure) | D |
| (structure) | D |
| (structure) | D |
| (structure) | D |
| (structure) | D |
| (structure) | D |
| (structure) | E |

Pharmaceutical Compositions

In another aspect, provided are pharmaceutical compositions comprising a compound of Formula (I), or a pharmaceutically acceptable salt, stereoisomer, or prodrug thereof, and a pharmaceutically acceptable excipient.

An "active ingredient," as used herein, refers to a compound of Formula (I), or a pharmaceutically acceptable salt, stereoisomer, or prodrug thereof. In certain embodiments, the active ingredient is present in an effective amount, e.g., a therapeutically effective amount or a prophylactically effective amount.

A pharmaceutical composition can be administered via one or more routes of administration using one or more of a variety of methods known in the art. As will be appreciated by the skilled artisan, the route and/or mode of administration will vary depending upon the desired results. The preferred route of administration is oral; however, depending on the condition of the patient, the desired result and the properties of the pharmaceutical composition other routes of administration may be used including but not limited to the following parenteral and non-parenteral routes of administration: intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal via injection and infusion; and intranasal, vaginal, rectal, sublingual or topical administration.

Depending on the route of administration, the pharmaceutical composition or active ingredient may be coated in a material to protect the compound from the action of acids and other natural conditions that may inactivate the compound.

Pharmaceutically acceptable excipients include any and all solvents, diluents or other liquid vehicles, dispersion or suspension aids, surface active agents, isotonic agents, thickening or emulsifying agents, preservatives, solid binders, lubricants and the like, as suited to the particular dosage form desired. General considerations in the formulation and/or manufacture of pharmaceutical compositions agents can be found, for example, in *Remington's Pharmaceutical Sciences*, Sixteenth Edition, E. W. Martin (Mack Publishing Co., Easton, Pa., 1980), and *Remington: The Science and Practice of Pharmacy*, 21$^{st}$ Edition (Lippincott Williams & Wilkins, 2005).

Pharmaceutical compositions described herein can be prepared by any method known in the art of pharmacology. In general, such preparatory methods include the steps of bringing the active ingredient into association with the excipient and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable carrier, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of a pharmaceutical composition include, but are not limited to, inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof.

Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include, but are not limited to, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof.

Exemplary binding agents include, but are not limited to, starch (e.g. cornstarch and starch paste), gelatin, sugars (e.g.

sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, etc., and/or combinations thereof.

Exemplary preservatives include, but are not limited to, antioxidants, chelating agents, antimicrobial preservatives, antifungal preservatives, alcohol preservatives, acidic preservatives, and other preservatives.

Exemplary antioxidants, but are not limited to, include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include, but are not limited to, ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include, but are not limited to, ethanol, polyethylene glycol, phenol, phenolic compounds, bisphenol, chlorobutanol, hydroxybenzoate, and phenylethyl alcohol.

Exemplary acidic preservatives include, but are not limited to, vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary natural oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor, alcohols, oils, modified oils, glycols, polysorbates, cyclodextrins, polymers, and combinations thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of the active ingredient, it is often desirable to slow the absorption of the active ingredient from subcutaneous or intramuscular injection. This can be accomplished by the use of a liquid suspension of crystalline or amorphous material with poor water solubility. The rate of absorption of the active ingredient then depends upon its rate of dissolution which, in turn, may depend upon crystal size and crystalline form. Alternatively, delayed absorption of a parenterally administered active ingredient is accomplished by dissolving or suspending the drug in an oil vehicle.

Compositions for rectal or vaginal administration are typically suppositories which can be prepared by mixing the conjugates of this invention with suitable non-irritating excipients or carriers such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient can be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

The active ingredient can be prepared with carriers that will protect the active ingredient against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

Pharmaceutical compositions can be administered with medical devices known in the art. For example, in a preferred embodiment, a pharmaceutical composition of this disclosure can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present disclosure include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation. General considerations in the formulation and/or manufacture of pharmaceutical compositions can be found, for example, in *Remington: The Science and Practice of Pharmacy* $21^{st}$ ed., Lippincott Williams & Wilkins, 2005.

The exact amount of the active ingredient required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of an active ingredient for administration one or more times a day to a 70 kg adult human may comprise about 0.1 mg to about 1000 mg, of the active ingredient per unit dosage form e.g., about 0.1 mg to about 900 mg, about 0.1 mg to about 800 mg, about 0.1 mg to about 700 mg, about 0.1 mg to about 600 mg, about 0.1 mg to about 500 mg, about 0.1 mg to about 400 mg, about 0.1 mg to about 300 mg, about 0.1 mg to about 200 mg, about 0.1 mg to about 100 mg, about 0.1 mg to about 90 mg, about 0.1 mg to about 80 mg, about 0.1 mg to about 70 mg, about 0.1 mg to about 60 mg, about 0.1 mg to about 50 mg, about 0.1 mg to about 40 mg, about 0.1 mg to about 30 mg, about 0.1 mg to about 20 mg, about 0.1 mg to about 10 mg, about 0.1 mg to about 5 mg, or about 0.1 mg to about 1 mg of the active ingredient per unit dosage form delivered one or more times a day to a 70 kg adult human.

In certain embodiments, the active ingredient may be administered orally or parenterally at dosage levels sufficient to deliver from about 0.06 mg/m$^2$ to about 600 mg/m$^2$ of body surface area, one or more times a day, to obtain the desired therapeutic effect e.g., the active ingredient is administered at a dosage level sufficient to deliver from about 0.06 mg/m$^2$ to about 500 mg/m$^2$, about 0.06 mg/m$^2$ to about 400 mg/m$^2$, about 0.06 mg/m$^2$ to about 300 mg/m$^2$, about 0.06 mg/m$^2$ to about 200 mg/m$^2$, about 0.06 mg/m$^2$ to about 100 mg/m$^2$, about 0.06 mg/m$^2$ to about 90 mg/m$^2$, about 0.06 mg/m$^2$ to about 80 mg/m$^2$, about 0.06 mg/m$^2$ to about 70 mg/m$^2$, about 0.06 mg/m$^2$ to about 60 mg/m$^2$, about 0.06 mg/m$^2$ to about 50 mg/m$^2$, about 0.06 mg/m$^2$ to about 40 mg/m$^2$, about 0.06 mg/m$^2$ to about 30 mg/m$^2$, about 0.06 mg/m$^2$ to about 20 mg/m$^2$, or about 0.06 mg/m$^2$ to about 10 mg/m$^2$ of body surface area to obtain the desired therapeutic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that the active ingredient or composition, as described herein, can be administered in combination with one or more additional therapeutically active agents. The active ingredient or compositions can be administered in combination with additional therapeutically active agents that improve their bioavailability, reduce and/or modify their metabolism, inhibit their excretion, and/or modify their distribution within the body. It will also be appreciated that the therapy employed may achieve a desired effect for the same disorder (for example, a compound can be administered in combination with an anti-cancer agent, etc.), and/or it may achieve different effects (e.g., control of adverse side-effects, e.g., emesis controlled by an anti-emetic).

The active ingredient or composition can be administered concurrently with, prior to, or subsequent to, one or more additional therapeutically active agents. In general, each agent will be administered at a dose and/or on a time schedule determined for that agent. It will further be appreciated that the additional therapeutically active agent utilized in this combination can be administered together in a single composition or administered separately in different compositions. The particular combination to employ in a regimen will take into account compatibility of the active ingredient with the additional therapeutically active agent and/or the desired therapeutic effect to be achieved. In general, it is expected that additional therapeutically active agents utilized in combination be utilized at levels that do not exceed the levels at which they are utilized individually. In some embodiments, the levels utilized in combination will be lower than those utilized individually.

Exemplary additional therapeutically active agents include, but are not limited to, cancer therapies (e.g., an anti-neoplastic agent or other anti-cancer therapy such as x-ray irradiation therapy), antibiotics, anti-viral agents, anesthetics, anti-coagulants, inhibitors of an enzyme, steroidal agents, steroidal or non-steroidal anti-inflammatory agents, antihistamine, immunosuppressant agents, anti-neoplastic agents, antigens, vaccines, antibodies, decongestant, sedatives, opioids, pain-relieving agents, analgesics, anti-pyretics, hormones, prostaglandins, progestational agents, anti-glaucoma agents, ophthalmic agents, anti-cholinergics, anti-depressants, anti-psychotics, hypnotics, tranquilizers, anti-convulsants/anti-epileptics (e.g., Neurontin, Lyrica, valproates (e.g., Depacon), and other neurostabilizing agents), muscle relaxants, anti-spasmodics, muscle contractants, channel blockers, miotic agents, anti-secretory agents, anti-thrombotic agents, anticoagulants, anti-cholinergics, P-adrenergic blocking agents, diuretics, cardiovascular active agents, vasoactive agents, vasodilating agents, anti-hypertensive agents, angiogenic agents, modulators of cell-extracellular matrix interactions (e.g., cell growth inhibitors and anti-adhesion molecules), or inhibitors/intercalators of DNA, RNA, protein-protein interactions, protein-receptor interactions, etc. Therapeutically active agents include small organic molecules such as drug compounds (e.g., compounds approved by the Food and Drugs Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins and cells.

Methods of Use and Treatment

MIF has been implicated in the pathogenesis of a wide range of disorders wherein an inflammatory immune response is a determinant of disease pathology (Grieb, G., et al., *Drug News Perspect*. 2010, 23, 257-264). Animal models wherein MIF expression is suppressed and/or studies of the effect of anti-MIF antibodies or small molecule inhibitors have identified MIF as a potential therapeutic target for inflammatory diseases such as multiple sclerosis (Kithcart, A. P., et al., *FASEB* 2010, 24, 4459-66), systemic lupus erythematosus (Wang, F., et al., *Arthritis Research & Therapy* 2012, 14:R103), arthritis (Willeke, P., et al., *Scand. J. Rheumatol*. 2012, 41, 242-3), periodontal disease (Madeira, M. F. M., et al., *Microbes and Infection* 2012, 14, 198-206), atopic dermatitis (Yoshihisa, Y., et al., *J. Invest. Dermatol*. 2011, 131, 925-31) and sepsis (Al-Abed, Y., et al., *J. Biol. Chem*. 2005, 280, 36541-4). Additionally, the observation that MIF antagonists block the toxic effects of Aβ on neuroblastoma cells suggests that MIF tautomerase inhibitors might delay the onset and progression of Alzheimer's disease (AD) by blocking the neuronal cell death seen in AD (Bacher, M., et al., *Mol. Med.* 2010, 16 (3-4), 116-121).

Although the aforementioned studies suggest that MIF induces an inflammatory response other studies suggest that MIF may in certain settings down regulate an inflammatory response. The observation that decreasing expression of MIF or antagonizing MIF activity with antibodies or small molecules inhibits MHC class-II immune responses (e.g. see Mizue, Y., et al., *PNAS* 2005, 102, 14410-14415), but enhances MHC class-I immune responses (e.g. see Abe, R., et al. *J. Immunol.* 2001, 166, 747-753) suggests that MIF inhibitors could have utility in treating disorders wherein a therapeutic effect might be obtained by inhibiting an MHC class-II immune response, e.g. asthma—a disorder wherein patients express elevated levels of MIF (e.g. see Rossi, A., et al., *J. Clin. Invest.* 1998, 101, 2869-2874), as well as diseases wherein a therapeutic effect might be obtained by enhancing an MHC class-I immune response (e.g. certain microbial infections, cancer and other proliferative diseases). Consistent with this hypothesis suppression of MIF expression or antagonizing the activity of MIF with antibodies or small molecule MIF tautomerase inhibitors reduces the airway hyper-responsiveness and airway remodeling seen in mouse models of asthma (e.g. see Magalhaes, E., et al., *Eur. J. Immunol.* 2007, 37, 1097-1106; Mizue, Y., et al., *PNAS* 2005, 102, 14410-14415; Chen, P.-F., et al., *Mol. Med.* 2010, 16, 400-408; Amano, T., et al., *Inflamm Res.* 2007, 56, 24-31). Analogous studies in mice of the effect of suppression of MIF expression and/or studies of the effect of anti-MIF antibodies or small molecule MIF tautomerase inhibitors have identified MIF as a potential therapeutic target for inhibiting tumor cell growth, metastasis and angiogenesis. These studies have implicated MIF in the growth of a prostate cancer cell line (Meyer-Siegler, K. L., et al., *J. Immunol.* 2006, 177, 8730-9), the growth and angiogenesis of lymphoma (Chesney, J., et al., *Mol. Med.* 1999, 5, 181-191), the growth of a lung adenocarcinoma (Winner, M., et al., *Cancer Res.* 2008, 68, 7253-757), the progression of tumors in a mouse model for HER2+ human breast cancer (Schulz, R., et al., *J. Exp. Med.* 2012, 209, 275-278), ulcerative colitis-induced colorectal tumorigensis (Wilson, J. M., et al., *Gastroenterology* 2005, 129, 1485-1503), nitrosoamine-induced bladder cancer (Taylor, J. A., et al., *BMC Cancer* 2007, 7, 135), and UVB-induced skin cancer (Martin, J., et al., *FASEB J.* 2009, 23, 720-730). Moreover, evidence has been presented suggesting that the anti-neoplastic activity of anti-MIF antibodies is due in part their enhancement of cytotoxic T-lymphocyte (CTL) activity (Abe, R., et al., *J. Immunol.* 2001, 166, 747-753).

The observation (e.g. Bini, L., et al., *Electrophoresis* 1997, 18, 2832-2841; Meyer-Siegler, K., et al., *Diagn. Mol. Pathol.* 1998, 7, 44-50; Shimizu, T., et al., *Biophys. Res. Commun.* 1999, 264, 751-758; Bando, H., et al., *Jpn. J. Cancer Res.* 2002, 93, 389-396; Ren, Yi., et al., *Int. J. Cancer* 2003, 107, 22-29; He, X., et al., *Gut* 2006, 55, 797-802) that MIF is overexpressed in many solid tumors suggests that overexpression of MIF and concomitant MIF-mediated suppression of CTL activity may well be an important determinant of the ability of tumor cells to evade a CD8+ T-cell based immune response. In that regard it is interesting to note that MIF expression induces expansion of myeloid derived suppressor cells (MDSCs) (Simpson, K. D., et al., *J. Immunol.* 2012, 189, 5533-40). MDSCs inhibit T cell responses (Almand, B., et al., *J. Immunol.* 2001, 166, 678-689), impair T cell proliferation (Zea, A. H., et al., *Cancer Res.* 2005, 65, 3044-8), and suppress innate and adaptive immune surveillance in most cancer patients (Ostrand-Rosenberg, S., et al., *J. Immunol.* 2009, 182, 4499-4506).

Moreover, it has been shown that MIF tautomerase induces expansion of MDSCs and thereby promotes tumor growth and metastasis in subjects, such as immune competent animals (Simpson, K. D., et al., *J. Immunol.* 2012, 189, 5533-40). This finding suggests that small molecule reversible inhibitors of MIF tautomerase could antagonize MIF-mediated suppression of a CD8+ T-cell immune response, and thereby provide safer more efficacious agents to treat cancer and other proliferative diseases, prevent metastasis, and also provide safer and more efficacious agents for treating or preventing infections by microbes (e.g., viruses, plasmodia, mycobacteria, fungi and helminths and other microbes) whose clearance is enhanced by a CD8+ T-cell immune response.

Additionally, the aforementioned findings suggest that MIF tautomerase inhibitors could enhance responses to peptide antigens in T-cell vaccines. Since MIF tautomerase inhibitors enhance CD8+ T-cell immune responses, a subject's response to therapy with a MIF tautomerase inhibitor may be dependent upon the subject's HLA haplotype and the target of the immune response. Thus, it may be important to determine the HLA haplotype of a subject to determine whether the subject will benefit from treatment or prophylaxis (e.g. with a vaccine) with a MIF tautomerase inhibitor by comparing the subject's HLA haplotype with those of subjects who have had favorable and unfavorable therapeutic or prophylactic responses to a MIF tautomerase inhibitor.

Moreover in cases where an infecting microbe expresses a MIF-tautomerase that potently suppresses a CD8+ T-cell immune response, it might be important to use MIF inhibitors that target the microbe's MIF (which may be more potent than the host's MIF in inhibiting the host's CD8+ T-cell immune response) to raise a therapeutically effective CD8+ T-cell immune response against the infecting microbe.

Thus, in one aspect, provided is a method of treating a disease or disorder associated with overexpression of MIF tautomerase activity, e.g., as described above and herein, comprising administering to a subject in need of such treatment an effective amount of a compound of Formula (I), or a pharmaceutically acceptable salt, stereoisomer, or prodrug thereof.

In yet another aspect, provided is a method of treating asthma in a subject in need thereof comprising administering to the subject an effective amount of a compound of Formula (I), or a pharmaceutically acceptable salt, stereoisomer, or prodrug thereof.

In yet another aspect, provided is a method of treating a cancer or other proliferative disease (e.g., such as but not limited to polycythemia vera, primary myelofibrosis, essential thrombocythemia, idiopathic pulmonary fibrosis, or atherosclerosis) in a subject in need thereof, comprising administering to the subject an effective amount of a compound of Formula (I), or a pharmaceutically acceptable salt, stereoisomer, or prodrug thereof.

In yet another aspect, provided is a method of treating a cancer in a subject comprising administering to the subject an effective amount of a compound of Formula (I), or a pharmaceutically acceptable salt, stereoisomer, or prodrug thereof, optionally in combination with at least one antineoplastic agent and/or a therapy such as but not limited to x-ray irradiation therapy.

In yet another aspect, provided is a method of treatment to prevent or suppress metastasis of a cancer in a subject comprising administering to a subject in need of such treatment an effective amount of a compound of Formula (I) or a pharmaceutically acceptable salt, stereoisomer, or prodrug thereof, optionally in combination with at least one anti-neoplastic agent and/or a therapy (e.g., such as but not limited to x-ray irradiation therapy).

In yet another aspect, provided is a method of treatment to prevent or suppress tumor growth in a subject comprising administering to a subject in need of such treatment an effective amount of a compound of Formula (I), or a pharmaceutically acceptable salt, stereoisomer, or prodrug thereof, optionally in combination with at least one anti-neoplastic agent and/or a therapy (e.g., such as but not limited to x-ray irradiation therapy).

Exemplary cancers include, but are not limited to, acoustic neuroma, adenocarcinoma, adrenal gland cancer, anal cancer, angiosarcoma (e.g., lymphangiosarcoma, lymphangioendotheliosarcoma, hemangiosarcoma), appendix cancer, benign monoclonal gammopathy, biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma; medulloblastoma), bronchus cancer, carcinoid tumor, cervical cancer (e.g., cervical adenocarcinoma), choriocarcinoma, chordoma, craniopharyngioma, colorectal cancer (e.g., colon cancer, rectal cancer, colorectal adenocarcinoma), epithelial carcinoma, ependymoma, endotheliosarcoma (e.g., Kaposi's sarcoma, multiple idiopathic hemorrhagic sarcoma), endometrial cancer (e.g., uterine cancer, uterine sarcoma), esophageal cancer (e.g., adenocarcinoma of the esophagus, Barrett's adenocarinoma), Ewing sarcoma, eye cancer (e.g., intraocular melanoma, retinoblastoma), familiar hypereosinophilia, gall bladder cancer, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC), throat cancer (e.g., laryngeal cancer, pharyngeal cancer, nasopharyngeal cancer, oropharyngeal cancer)), hematopoietic cancers (e.g., leukemia such as acute lymphocytic leukemia (ALL) (e.g., B-cell ALL, T-cell ALL), acute myelogenous leukemia (AML) (e.g., B-cell AML, T-cell AML), chronic myelogenous leukemia (CML) (e.g., B-cell CML, T-cell CML), and chronic lymphocytic leukemia (CLL) (e.g., B-cell CLL, T-cell CLL); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma (DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., "Waldenstrom's macroglobulinemia"), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, anaplastic large cell lymphoma); a mixture of one or more leukemia/lymphoma as described above; and multiple myeloma (MM)), heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, small cell lung cancer (SCLC), non-small cell lung cancer (NSCLC), adenocarcinoma of the lung), leiomyosarcoma (LMS), mastocytosis (e.g., systemic mastocytosis), myelodysplastic syndrome (MDS), mesothelioma, myeloproliferative disorder (MPD) (e.g., polycythemia Vera (PV), essential thrombocytosis (ET), agnogenic myeloid metaplasia (AMM) a.k.a. myelofibrosis (MF), chronic idiopathic myelofibrosis, chronic myelogenous leukemia (CML), chronic neutrophilic leukemia (CNL), hypereosinophilic syndrome (HES)), neuroblastoma, neurofibroma (e.g., neurofibromatosis (NF) type 1 or type 2, schwannomatosis), neuroendocrine cancer (e.g., gastroenteropancreatic neuroendoctrine tumor (GEP-NET), carcinoid tumor), osteosarcoma, ovarian cancer (e.g., cystadenocarcinoma, ovarian embryonal carcinoma, ovarian adenocarcinoma), papillary adenocarcinoma, pancreatic cancer (e.g., pancreatic andenocarcinoma, intraductal papillary mucinous neoplasm (IPMN), Islet cell tumors), penile cancer (e.g., Paget's disease of the penis and scrotum), pinealoma, primitive neuroectodermal tumor (PNT), prostate cancer (e.g., prostate adenocarcinoma), rectal cancer, rhabdomyosarcoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), urethral cancer, vaginal cancer, and vulvar cancer (e.g., Paget's disease of the vulva).

In certain embodiments, the cancer is breast cancer, e.g., metastatic breast cancer. In certain embodiments, the tumor growth is breast cancer tumor growth.

In another aspect, provided is a method of treating a microbial infection comprising administering to a subject in need of such treatment an effective amount of a compound of Formula (I), or a pharmaceutically acceptable salt, stereoisomer, or prodrug thereof, optionally in combination with at least one antimicrobial agent.

In yet another aspect, provided is a method of treatment to maintain a microbial infection in a latent state comprising administering to a subject in need of such treatment an effective amount of a compound of Formula (I), or a pharmaceutically acceptable salt, stereoisomer, or prodrug thereof, optionally in combination with at least one antimicrobial agent.

Exemplary microbial infections include, but are not limited to, an infection with a virus, such as but not limited to HIV, ebola virus, hepatitis C virus, herpes simplex virus I, herpes simplex virus II or varicella zoster virus; a mycobacterium, such as but not limited to *Mycobacterium tuberculosis*; a Plasmodium, such as but not limited to *Plasmodium falciparum, Plasmodium vivax, Plasmodium ovale* or *Plasmodium malariae*; a fungus, such as but not limited to *Candida albicans, Cryptococcus neoformans, Aspergillus fumigatus, Epidermophyton floccosum*, or *Trichophyton* rubrum; or a helminth such as but not limited to *Ascariasis lumbricoides, Trichuris trichiura*, or *Necator americanus*.

In yet another aspect, provided is a method of vaccination comprising administering a compound of Formula (I), or a pharmaceutically acceptable salt, stereoisomer, or prodrug thereof, or at least one MIF tautomerase inhibitor such as one disclosed elsewhere (e.g. ISO-1 (U.S. Pat. No. 8,362,053 B2), 4-IPP (Winner, M., et al., *Cancer Res.* 2008, 68, 7253-7257), and the 3,4-dihydro-benzo[e][1,3]oxazin-2-ones disclosed by Billich., et al. (U.S. Pat. No. 7,378,416 B2)), in combination with an antigen formulation that promotes CD8+ T-cell based immunity in a subject in need thereof.

In yet still another aspect, provided is a method of treating or vaccinating a subject in need thereof with a MIF tautomerase inhibitor or a MIF tautomerase inhibitor augmented vaccine, wherein the subject's HLA haplotype is determined, and the subject is treated or vaccinated only if the subject's HLA haplotype matches more closely to the HLA haplotypes of those who previously benefited from the therapy or vaccination than to the HLA haplotypes of those who did not benefit from the therapy or vaccination.

EXEMPLIFICATION

In order that the invention described herein may be more fully understood, Reaction Schemes 1-13 for preparing MIF inhibitors of Formula (I) are set forth by way of example. It should be understood that these examples are for illustrative purposes only and are not to be construed as limiting this invention in any manner.

Synthetic Methods

Abbreviations used in the examples are as follows:
THF=tetrahydrofuran
TMEDA=tetramethylethylenediamine
EtOAc=ethyl acetate
AcOH=acetic acid
MeCN=acetonitrile
DMF=dimethylformamide
MeOH=methanol
EtOH=ethanol
DIPEA=diisopropylethylamine
DCE=1,2-dichloroethane
DCM=dichloromethane
HPLC=high performance liquid chromatography
MS=mass spectrometry
PCC=pyridinium chlorochromate
DMAP=4-dimethylaminopyridine
TFA=trifluoroacetic acid
Tris=tris(hydroxymethyl)aminomethane
Cbz=benzyloxycarbonyl
DEAD=diethyl azodicarboxylate
DIAD=diisopropyl azodicarboxylate
Et$_3$N or TEA=triethylamine
NBS=N-bromosuccinimide
EDCI=1-ethyl-3-(3-dimethylaminopropyl)carbodiimide
HOBt=hydroxybenzotriazole
DIBAL-H=diisobutylaluminium hydride
DMSO=dimethyl sulfoxide2-PrOH=isopropanol
TMP=2,2,6,6-tetramethylpiperidine
t-Boc=tert-butyloxycarbonyl
dr=diastereomeric ratio

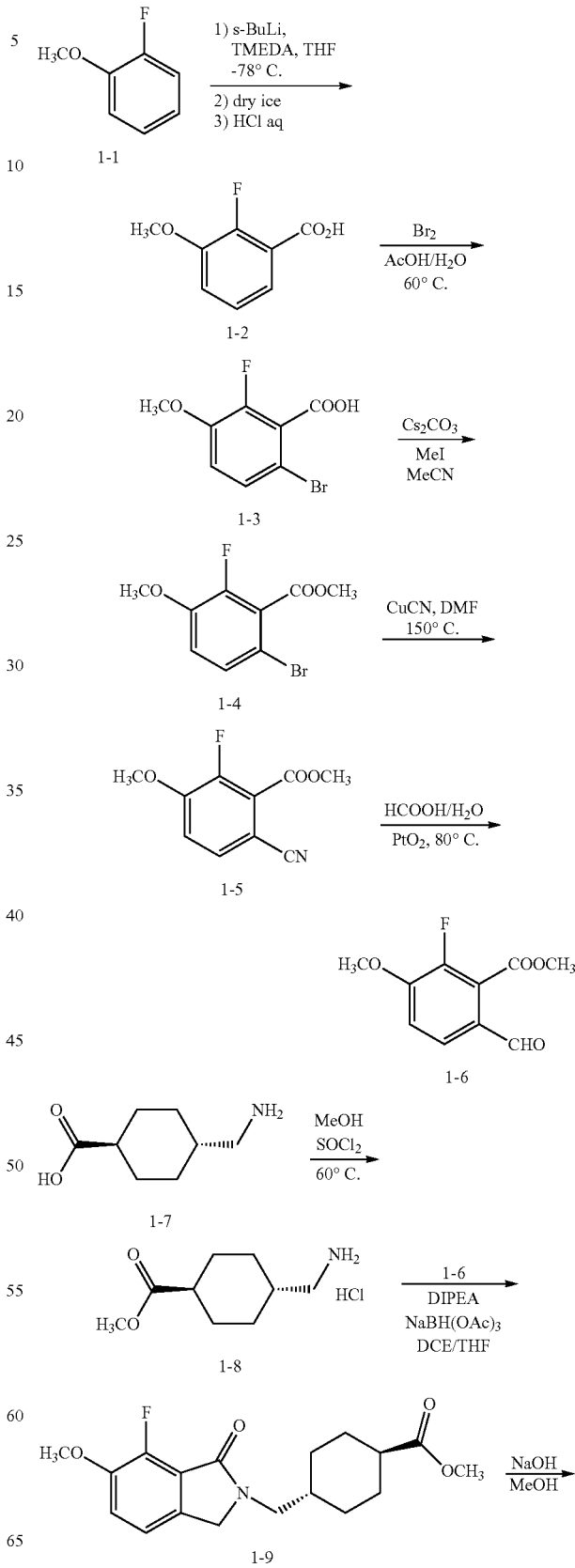

-continued

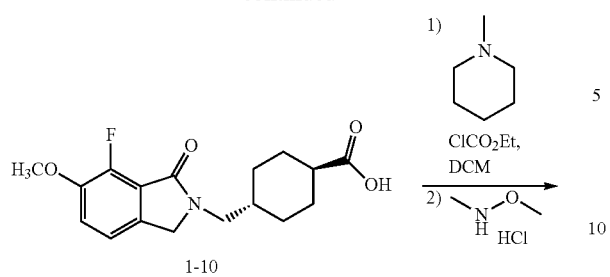

1-10

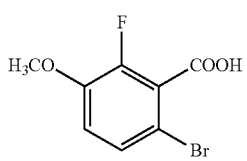 [SMILES: COc1ccc(Br)c(C(=O)O)c1F]

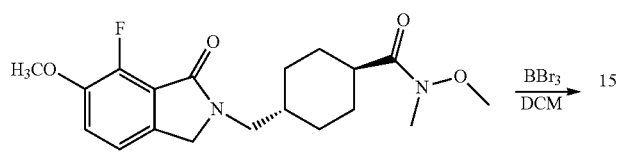

1-11

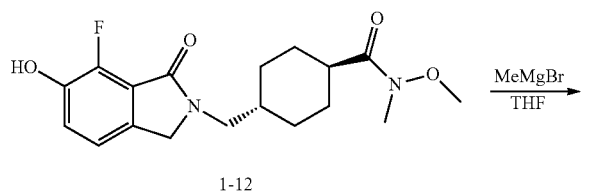

1-12

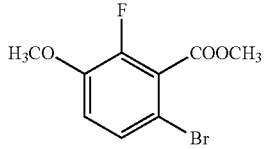 [SMILES: COC(=O)c1c(Br)ccc(OC)c1F]

1-13

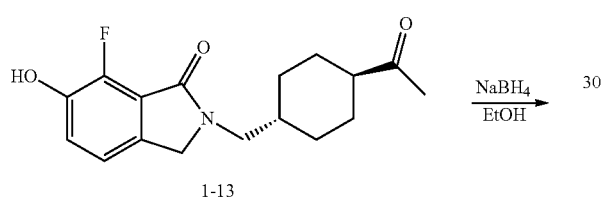

1-14

Example 1

H₃CO, F, CO₂H

2-Fluoro-3-methoxybenzoic acid (1-2)

Compound 1-2 was prepared from 1-1 (Alfa Aesar) by a procedure similar to that described in Bridges, A. J., et al., *Tetrahedron Letters* 1992, 33, 7495-8 and Katsoulos, G., et al., *Synlett* 1991, 731-2.

Example 2

H₃CO, F, COOH, Br

6-Bromo-2-fluoro-3-methoxybenzoic acid (1-3)

Compound 1-3 was prepared from 1-2 by a procedure similar to that described in PCT Int. Appl. 2008020306.

Example 3

H₃CO, F, COOCH₃, Br

Methyl 6-bromo-2-fluoro-3-methoxybenzoate (1-4)

Compound 1-3 (76.3 g, 0.308 mol) was dissolved in acetonitrile (1.8 L) in a 3-L 3-necked flask under an argon atmosphere at rt, and anhydrous cesium carbonate (115 g, 0.354 mol) was added to the stirred solution followed by slow addition of methyl iodide (28.8 mL, 0.461 mol). After the resultant suspension was stirred vigorously for 46 h, the solids were filtered off through a short pad of Celite and washed with EtOAc (3×100 mL). The filtrate was concentrated to remove MeCN, taken up in diethyl ether (300 mL), and washed with 0.5 N HCl (300 mL). The separated aqueous solution was extracted with ether (3×100 mL) and the combined organic phases were washed with 0.5 N HCl (200 mL) and water (2×200 mL). The resulting organic phase was dried over Na₂SO₄, filtered, concentrated to yield 1-4 as an orange oil (82 g, 100% yield). HPLC >99% pure.

Example 4

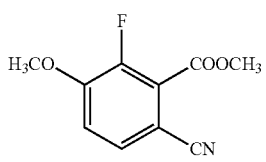 [SMILES: COC(=O)c1c(C#N)ccc(OC)c1F]

Methyl 6-cyano-2-fluoro-3-methoxybenzoate (1-5)

Compound 1-5 was prepared from 1-4 by a procedure similar to that described in Powers, J. J., et al., *Tetrahedron Letters* 2009, 50, 1267-9.

Example 5

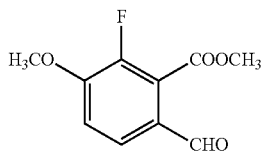

Methyl 2-fluoro-6-formyl-3-methoxybenzoate (1-6)

A mixture of 1-5 (5.43 g, 26 mmol) and platinum(IV) oxide (1.18 g, 5.2 mmol) in 60 mL of 88% aqueous formic acid and 6 mL of water was stirred at 80° C. for 2 h, after which time additional 88% aqueous formic acid (20 mL), water (2 mL) and platinum(IV) oxide (0.8 g, 3.53 mmol) were added and the reaction mixture stirred for 3 h. The reaction mixture was then cooled to rt, diluted with water (30 mL) and filtered. The solid residue on the filter was washed with ether (2×25 mL) and then EtOAc (2×30 mL). The aqueous phase from the filtrate and washings was separated and extracted with EtOAc (3×50 mL). The organic phases were combined, washed with water (3×30 mL), dried over $Na_2SO_4$, filtered through a short pad of silica gel, and concentrated to yield crude 1-6 as a yellow oil (contained ~17 mmol (66%) of 1-6 and ~9 mmol (34%) of 1-5 based on HPLC), which was used in the next step without further purification.

Example 6

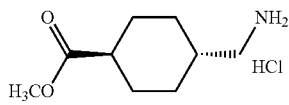

Trans-methyl 4-(aminomethyl)cyclohexanecarboxylate hydrochloride (1-8)

Compound 1-7 (TCI America) (14.4 g, 91.7 mmol) was mixed with MeOH (150 mL) and to this resultant suspension was added thionyl chloride (14.4 mL, 201.6 mmol) dropwise at 0° C. with stirring. The amino acid (1-7) dissolved gradually upon the addition of thionyl chloride. The reaction mixture was stirred at 60° C. overnight, cooled to rt, and solvent evaporated to yield 1-8 as a white solid (20 g, 100% yield).

Example 7

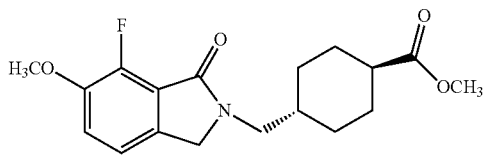 [SMILES: COc1ccc2c(c1F)C(=O)N(C[C@H]1CC[C@H](C(=O)OC)CC1)C2]

Trans-methyl 4-((7-fluoro-6-methoxy-1-oxoisoindolin-2-yl)methyl)cyclohexanecarboxylate (1-9)

To a solution of crude 1-6 (containing ~17 mmol of 1-6) in DCE/THF (180 mL/25 mL) were added compound 1-8 (5.4 g, 26 mmol) and DIPEA (2.25 mL, 13 mmol) at rt. The mixture was stirred for 20 min before $NaBH(OAc)_3$ (97%) (7.29 g, 32 mmol) was added. After the reaction mixture was stirred at rt for 40 h, it was washed with 2 N HCl (3×50 mL) and the combined aqueous phase was extracted with DCM (60 mL). All the organic phases were combined, dried over $Na_2SO_4$, filtered and concentrated to yield a residue. The residue was taken up in hexane/EtOAc (1/1, 30 mL) and kept at −20° C. for 15 min to yield a white solid, which was collected via vacuum filtration and washed with hexane to yield a crop of 1-9 (95% pure on HPLC). The filtrate was concentrated and purified by flash chromatography on silica gel (EtOAc/MeOH=10/1) to afford a second crop of product. The two crops of 1-9 were combined to yield 1-9 as a white solid (5.3 g, 93% yield). HPLC 95% pure.

Example 8

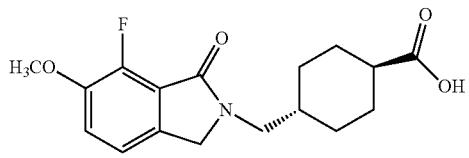 [SMILES: COc1ccc2c(c1F)C(=O)N(C[C@H]1CC[C@H](C(=O)O)CC1)C2]

Trans-4-((7-fluoro-6-methoxy-1-oxoisoindolin-2-yl)methyl)cyclohexanecarboxylic acid (1-10)

Compound 1-9 (5.3 g, 15.8 mmol) was dissolved in MeOH (45 mL) and then heated up to 65° C. before 1 N NaOH (40 mL) was added portion wise. After the mixture was stirred at 65° C. for 40 min, a clear solution was obtained. After another 15 min, the reaction mixture was concentrated under reduced pressure to remove MeOH and then acidified with 6 N HCl slowly to pH 1 with stirring. The resulting white precipitate was collected by vacuum filtration, washed with water (15 mL) and EtOAc (15 mL) to yield the first crop of 1-10. The filtrate was extracted with DCM (2×40 mL) and EtOAc (2×50 mL). The combined organic phases were dried over $Na_2SO_4$, filtered and concentrated to yield the second crop of 1-10. The two crops of product were combined to afford 1-10 as a white solid (5 g, 99% yield).

Example 9

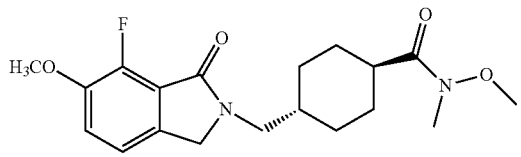 [SMILES: COc1ccc2c(c1F)C(=O)N(C[C@H]1CC[C@H](C(=O)N(C)OC)CC1)C2]

Trans-4-((7-fluoro-6-methoxy-1-oxoisoindolin-2-yl)
methyl)-N-methoxy-N-methylcyclohexanecarbox-
amide (1-11)

Compound 1-10 (2.5 g, 7.79 mmol) was dissolved in DCM (80 mL) and cooled in an ice/water bath under an argon atmosphere. To this were added N-methylpiperidine (4.26 mL, 3.46 g, 35 mmol) and then ethyl chloroformate (1.5 mL, 1.71 g, 15.4 mmol) dropwise. After the mixture was stirred for 15 min with cooling, N,O-dimethylhydroxylamine hydrochloride (1.68 g, 16.8 mmol) was added. The ice/water bath was removed and the reaction mixture was allowed to warm up to rt. After the mixture was stirred for 4 h, additional N-methylpiperidine (4.26 mL, 3.46 g, 35 mmol) and ethyl chloroformate (1.5 mL, 1.71 g, 15.4 mmol) were added dropwise followed by the addition of N,O-dimethylhydroxylamine hydrochloride (1.25 g, 12.5 mmol). After the reaction mixture was stirred overnight at rt, it was washed with 1 N HCl (3×80 mL), water (50 mL), and the combined aqueous phase was extracted with DCM (50 mL). The organic phases were combined, concentrated and purified by flash chromatography on silica gel (EtOAc/MeOH=5/1) to yield 1-11 as an off-yellow solid (2.3 g, 81% yield). HPLC >99% pure.

Example 10

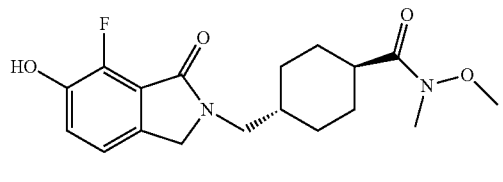 [SMILES: CON(C)C(=O)[C@H]1CC[C@H](CN2Cc3ccc(O)c(F)c3C2=O)CC1]

Trans-4-((7-fluoro-6-hydroxy-1-oxoisoindolin-2-yl)
methyl)-N-methoxy-N-methylcyclohexanecarbox-
amide (1-12)

Compound 1-11 (2.3 g, 6.3 mmol) was taken up in dry DCM (90 mL) under argon and to this was added BBr$_3$ (1M DCM solution, 24 mL, 24 mmol) dropwise at 0° C. The ice-bath was removed and the reaction mixture was allowed to warm up to rt. After the reaction mixture was stirred for 2 h, the reaction was quenched with water (50 mL) slowly and stirred for 10 min. The separated aqueous phase was extracted with EtOAc (3×30 mL) and the combined organic phases were dried over sodium sulfate, filtered, and concentrated to yield 1-12 (2.23 g, 91% yield). HPLC 90% pure.

Example 11

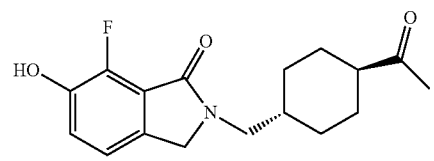 [SMILES: CC(=O)[C@H]1CC[C@H](CN2Cc3ccc(O)c(F)c3C2=O)CC1]

2-((Trans-4-acetylcyclohexyl)methyl)-7-fluoro-6-
hydroxyisoindolin-1-one (1-13)

Compound 1-12 (2 g, 5.71 mmol) was dissolved in dry THF (300 mL) in a flame-dried 500-mL flask with stirring at rt. The solution was cooled in an ice-bath under argon and to this was added dropwise via a syringe a 3 M solution of methylmagnesium bromide in diethyl ether (8.56 mL, 25.7 mmol). After 0.5 h, the ice-bath was removed and the reaction mixture allowed to warm up to rt. After the reaction mixture was stirred for 4 h, the reaction was quenched slowly with 1 N HCl (100 mL). The aqueous phase was separated and extracted with EtOAc (3×40 mL). The organic phases were combined, concentrated and purified by flash chromatography on silica gel (hexane/EtOAc/MeOH=10/20/3) to yield compound 1-13 (1.27 g, 73% yield). HPLC >99% pure; MS m/e 304 (M–H).

Example 12

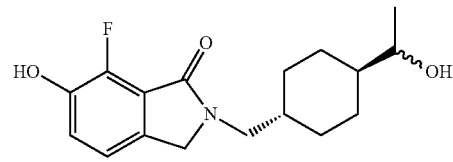 [SMILES: CC(O)[C@H]1CC[C@H](CN2Cc3ccc(O)c(F)c3C2=O)CC1]

7-Fluoro-6-hydroxy-2-((trans-4-(1-hydroxyethyl)
cyclohexyl)methyl)isoindolin-1-one (1-14)

Compound 1-13 (370 mg, 1.2 mmol) was dissolved in ethanol (50 mL) at rt and sodium borohydride (87 mg, 2.36 mmol) added. After the mixture was stirred for 40 min, the reaction was quenched slowly with 1 N HCl (50 mL) and the ethanol evaporated under reduced pressure. The resultant aqueous phase was extracted with EtOAc (3×20 mL) and the combined organic phase was dried over sodium sulfate, filtered, concentrated and purified by flash chromatography on silica gel (hexane/EtOAc/MeOH=10/20/3) to yield compound 1-14 as a white solid (370 mg, 100% yield). HPLC >99% pure; MS m/e 306 (M–H).

REACTION SCHEME 2

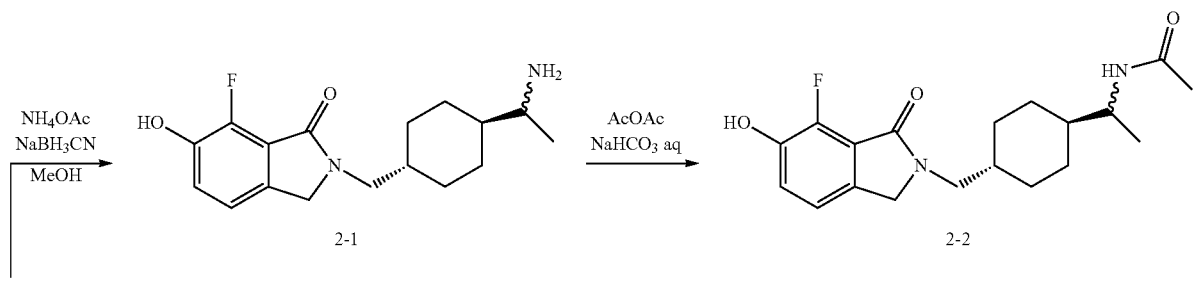

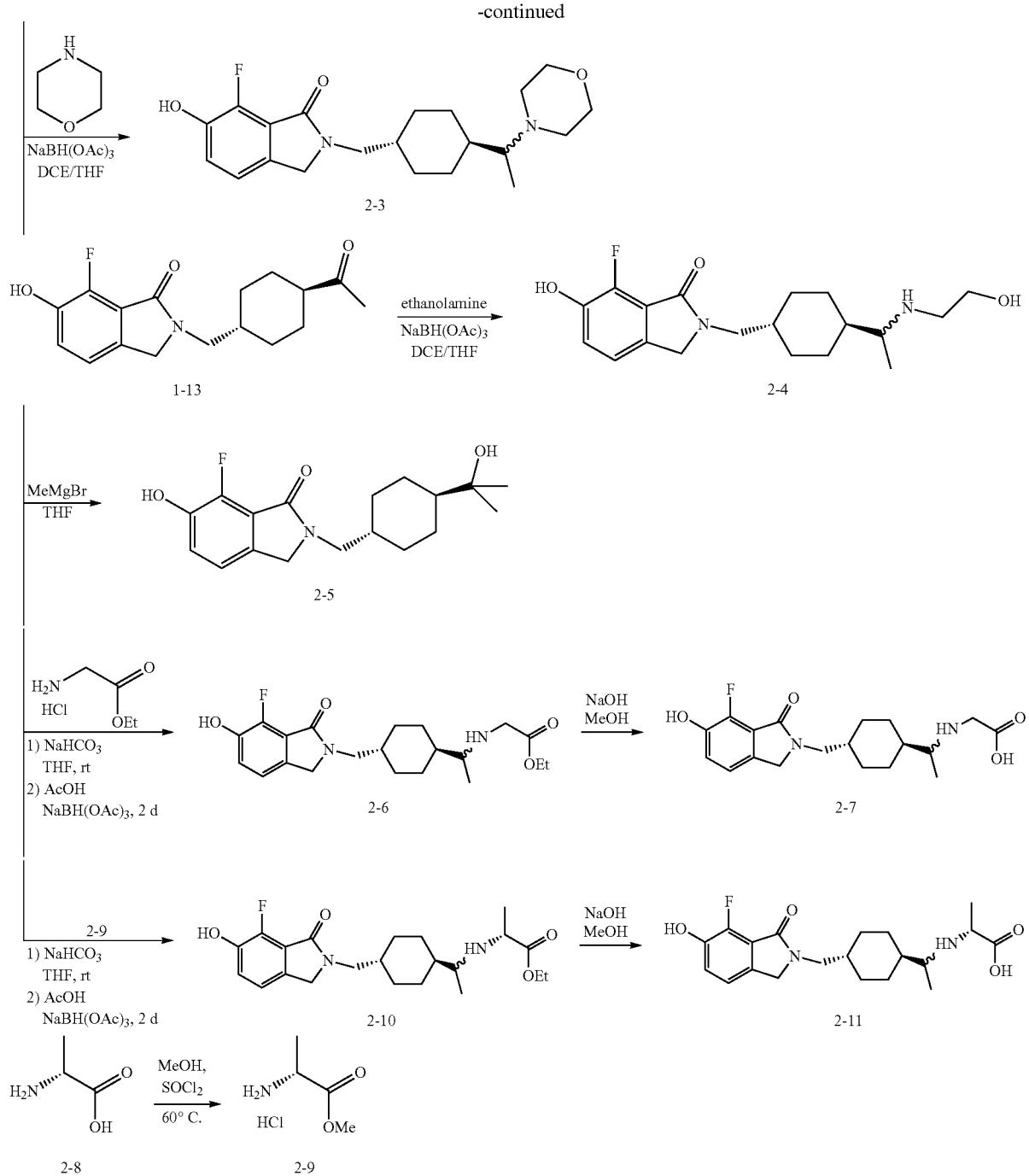

Example 13

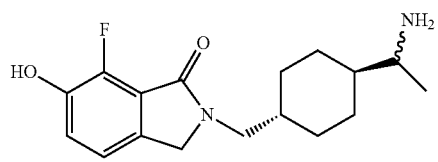 [SMILES: CC(N)[C@H]1CC[C@H](CN2Cc3ccc(O)c(F)c3C2=O)CC1]

2-((Trans-4-(1-aminoethyl)cyclohexyl)methyl)-7-fluoro-6-hydroxyisoindolin-1-one (2-1)

1-13 (15 mg, 0.049 mmol) was dissolved in a solution of ammonia acetate (70 mg, 0.91 mmol) in anhydrous MeOH (0.88 mL). To the resulting solution was added NaBH$_3$CN (22 mg, 0.35 mmol) and the mixture stirred at rt for 4 h. The MeOH was evaporated and the residue taken up in 0.5 N HCl (3 mL) and washed with DCM (2×2 mL). The acidic aqueous phase was separated, basified to pH 9 and washed with DCM (3 mL). The aqueous solution (pH 9) was then concentrated under reduced pressure at 60-80° C. and the resulting residue was taken up in 2-propanol (3×1 mL). The combined 2-propanol phases were concentrated to yield 2-1 (12 mg, 80% yield). HPLC 97% pure.

Example 14

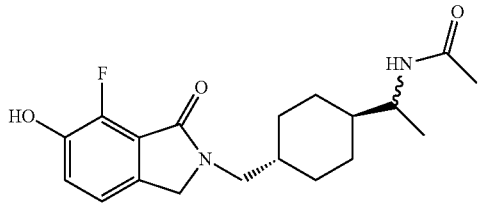 [SMILES: CC(=O)NC(C)[C@H]1CC[C@H](CN2Cc3ccc(O)c(F)c3C2=O)CC1]

N-(1-(Trans-4-((7-fluoro-6-hydroxy-1-oxoisoindolin-2-yl)methyl)cyclohexyl)ethyl)acetamide (2-2)

2-1 (2 mg, 0.0065 mmol) was added to a stirred solution of saturated NaHCO₃ (0.2 mL) followed by addition of acetic anhydride (3.8 µL, 0.04 mmol). After 20 min, the reaction mixture was acidified with 4 drops of 6 N HCl and the resulting acidic solution was subjected to reverse phase C-18 silica gel chromatography using a gradient of 0-100% MeCN in 0.07% aqueous TFA as eluent. Evaporation of the eluent from the collected fractions containing 2-2 afforded pure 2-2 (~1 mg). HPLC >99% pure; MS m/e 347 (M–H).

Example 15

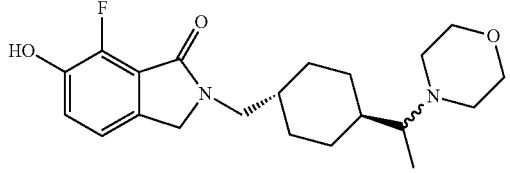 [SMILES: CC([C@H]1CC[C@H](CN2Cc3ccc(O)c(F)c3C2=O)CC1)N1CCOCC1]

7-Fluoro-6-hydroxy-2-((trans-4-(1-morpholinoethyl)cyclohexyl)methyl)isoindolin-1-one (2-3)

To a solution of 1-13 (20 mg, 0.066 mmol) in DCE/THF (0.65 mL/0.05 mL) were added morpholine (11.4 µL, 0.131 mmol) and acetic acid (5.7 µL, 0.1 mmol). After the mixture was stirred for several minutes, NaBH(OAc)₃ (97%) (30 mg, 0.131 mmol) was added. The mixture was stirred at rt for 6 days and the reaction mixture extracted with 0.5 N HCl (3×1.5 mL). The combined aqueous extracts were washed with DCM (2 mL) and the pH of the aqueous solution was adjusted to 7.5-8.0. The resulting aqueous phase was extracted with EtOAc (5×3 mL) and the combined EtOAc extracts were dried over sodium sulfate, filtered, and concentrated. The residue was dried azeotropically on the rotovapor with toluene (3×1 mL) to remove trace of morpholine to yield 2-3 as an oil (12.2 mg, 49% yield). HPLC 96% pure; MS m/e 375 (M–H).

Example 16

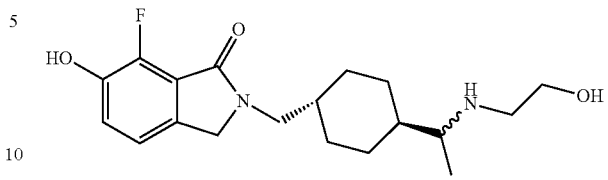

2-((Trans-4-(1-(2-hydroxyethylamino)ethyl)cyclohexyl)methyl)-7-fluoro-6-hydroxyisoindolin-1-one (2-4)

Compound 2-4 was prepared from 1-13 by a procedure analogous to that used to prepare 2-3 except that ethanolamine was used in place of morpholine. HPLC 95% pure; MS m/e 349 (M–H).

Example 17

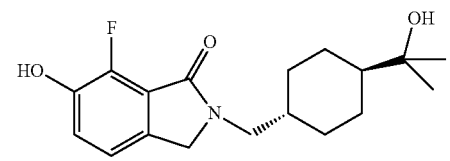

7-Fluoro-6-hydroxy-2-((trans-4-(2-hydroxypropan-2-yl)cyclohexyl)methyl)isoindolin-1-one (2-5)

To a solution of 1-13 (8 mg, 0.026 mmol) in dry THF (10 mL) was added a 3 M solution of methylmagnesium bromide in diethyl ether (100 µL, 0.3 mmol) dropwise under argon with stirring at rt. After the mixture was stirred for 1.5 h, the reaction was quenched with 1 N HCl (15 mL) and the separated aqueous phase extracted with EtOAc (3×10 mL). The organic phases were combined, concentrated and purified by flash chromatography on silica gel (hexane/EtOAc/MeOH=10/20/3) to yield 2-5 (6 mg, 72% yield). HPLC >99% pure; MS m/e 320 (M–H).

Example 18

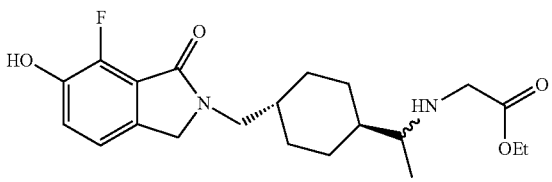 [SMILES: CCOC(=O)CNC(C)[C@H]1CC[C@H](CN2Cc3ccc(O)c(F)c3C2=O)CC1]

Ethyl 2-(1-(trans-4-((7-fluoro-6-hydroxy-1-oxoisoindolin-2-yl)methyl)cyclohexyl)ethylamino)acetate (2-6)

Glycine ethyl ester hydrochloride salt (16.4 mg, 0.118 mmol) and sodium bicarbonate (9.9 mg, 0.118 mmol) were stirred in anhydrous THF (0.6 mL) under an atmosphere of argon for 70 min before 1-13 (12 mg, 0.039 mmol) in DCE (0.14 mL), and acetic acid (5.7 μL, 0.1 mmol) were added. After several minutes, sodium triacetoxyborohydride (25 mg, 0.118 mmol) was added. The reaction mixture was stirred for 51 h under an atmosphere of argon and then diluted with DCM (1 mL) and washed with saturated sodium bicarbonate (3×2 mL). The organic phase was concentrated and purified by flash chromatography on silica gel (EtOAc/MeOH=10/1) to yield 2-6 (13.1 mg, 28% yield). HPLC 95% pure.

Example 19

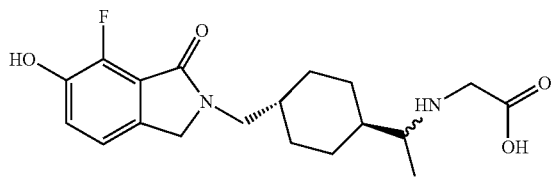 [SMILES: CC(NCC(=O)O)[C@H]1CC[C@H](CN2Cc3ccc(O)c(F)c3C2=O)CC1]

2-(1-(Trans-4-((7-fluoro-6-hydroxy-1-oxoisoindolin-2-yl)methyl)cyclohexyl)ethylamino)acetic acid (2-7)

2-6 (5 mg, 0.013 mmol) in MeOH (229 μL) was mixed with 0.1 N NaOH (390 μL, 0.039 mmol) and the mixture was stirred at 60° C. for 1 h. The MeOH was evaporated and the aqueous solution was acidified to pH 1-2. The aqueous solution was then evaporated to dryness and taken up in absolute EtOH (1.5 mL) to yield a 2-7/EtOH solution (4.1 mg/1.5 mL, 87% yield). HPLC >99% pure; MS m/e 363 (M–H).

Example 20

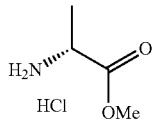

D-alanine methyl ester hydrochloride (2-9)

2-9 was prepared from D-alanine (2-8) by a procedure analogous to that used to prepare 1-8.

Example 21

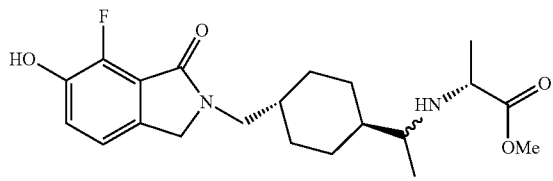 [SMILES: COC(=O)[C@@H](C)NC(C)[C@H]1CC[C@H](CN2Cc3ccc(O)c(F)c3C2=O)CC1]

(R)-Methyl 2-(1-(trans-4-((7-fluoro-6-hydroxy-1-oxoisoindolin-2-yl)methyl)cyclohexyl)ethylamino)propanoate (2-10)

2-10 was prepared from 1-13 and 2-9 by a procedure analogous to that used in the synthesis of 2-6. HPLC >99% pure (two peaks with diastereomeric ratio (dr) of 74/26); MS m/e 391 (M–H). The diastereoisomeric mixture of 2-10 was separated with flash chromatography on silica gel (hexane/EtOAc/MeOH=10/20/3) to yield two fractions of product (dr=100/0 and 10/90 respectively).

Example 22

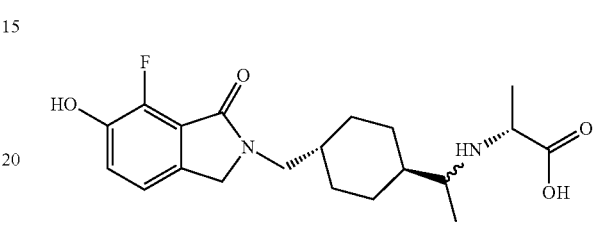

(R)-2-(1-(Trans-4-((7-fluoro-6-hydroxy-1-oxoisoindolin-2-yl)methyl)cyclohexyl)ethylamino)propanoic acid (2-11)

2-11 was prepared from 2-10 (the two isomers with dr=100/0 and 10/90 respectively) by a procedure analogous to that used in the synthesis of 2-7. HPLC >99% pure; MS m/e 377 (M–H).

REACTION SCHEME 3

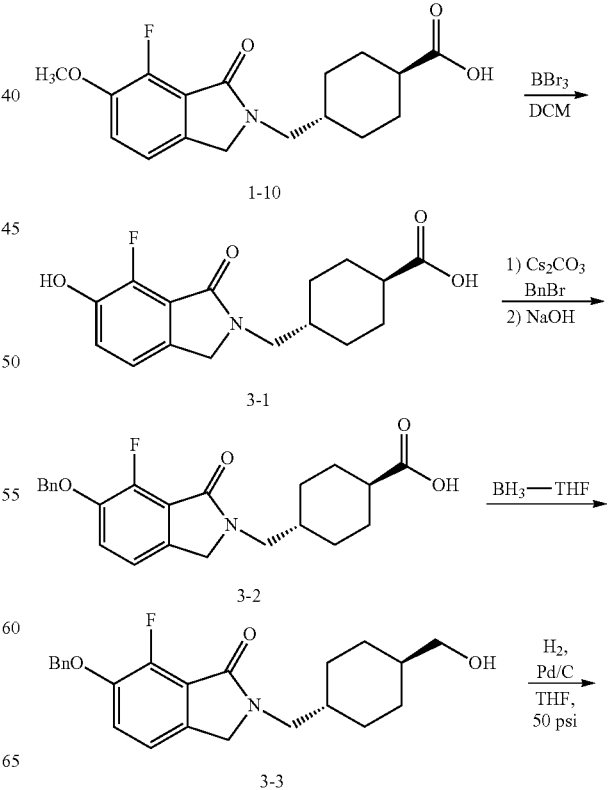

mL, 17.28 mmol) in DMF (20 mL) and MeCN (40 mL) was stirred vigorously under an argon atmosphere at rt overnight. The solids were filtered off through a short pad of Celite and the filtrate concentrated to remove MeCN. The resulting residue was taken up in diethyl ether (60 mL) and washed with water (40 mL). The separated aqueous layer was extracted with ether (3×30 mL) and all the organic phases were combined, concentrated to yield crude benzyl ester product as an oily residue. The residue was stirred in EtOH (80 mL) and 1 N NaOH (40 mL) at 60° C. for 70 min. The reaction mixture was concentrated to remove EtOH, washed with ether (20 mL), acidified to pH 1, and extracted with DCM (3×25 mL). All the DCM extracts were combined, dried over sodium sulfate, concentrated to yield 3-2 as an off-white solid (1 g, 47% yield). HPLC 92% pure.

Example 25

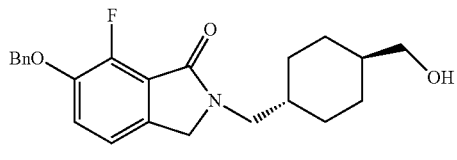

6-(Benzyloxy)-7-fluoro-2-((trans-4-(hydroxymethyl)cyclohexyl)methyl)isoindolin-1-one (3-3)

3-2 (1 g, 2.52 mmol) was dissolved in dry THF (30 mL) and to this solution was added borane-THF complex solution (1 M in THF, 5 mL, 5 mmol, 2 eq) dropwise under argon with stirring. After the mixture was stirred for 1.5 h at rt, additional borane-THF (1 M in THF, 2.5 mL, 2.5 mmol) was added dropwise. After one more hour of stirring, water (40 mL) was added slowly to the reaction mixture followed by addition of 2 N HCl (5 mL). The aqueous phase was separated and extracted with DCM (3×20 mL). The organic phases were combined, dried over sodium sulfate, concentrated to yield 3-3 (0.92 g, 95% yield). HPLC >98% pure.

Example 26

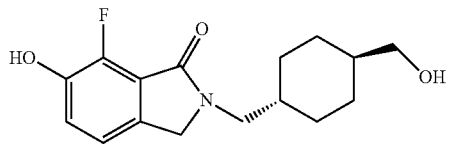

7-Fluoro-6-hydroxy-2-((trans-4-(hydroxymethyl)cyclohexyl)methyl)isoindolin-1-one (3-4)

3-3 (20 mg, 0.052 mmol), 10% Pd/C (30 mg), and THF (30 mL) in a 500 mL-Parr bottle was shaken under 50 psi of hydrogen overnight. The mixture was filtered and concentrated. The residue was purified by flash chromatography on silica gel (hexane/EtOAc/MeOH=10/20/3) to yield 3-4 (15 mg, 98% yield). HPLC 97% pure; MS m/e 292 (M–H).

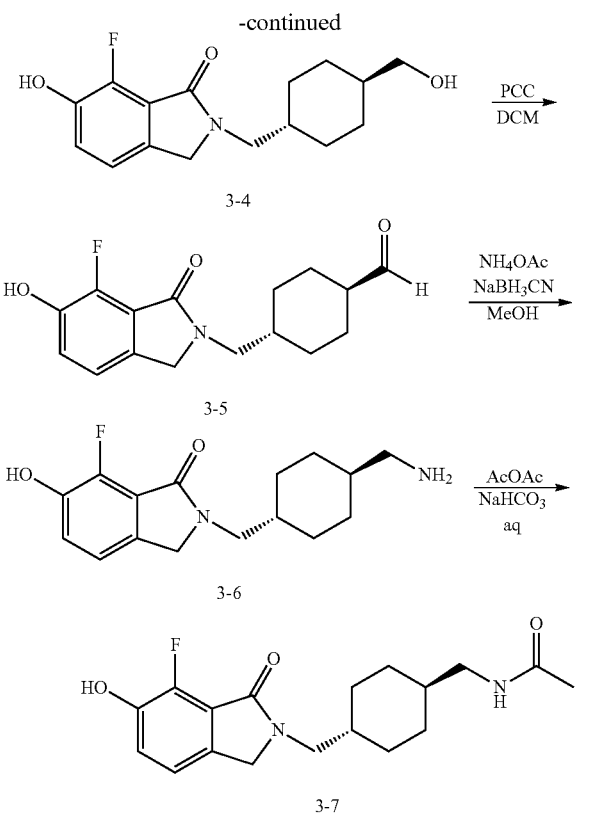

Example 23

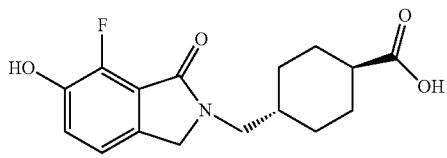 [SMILES: O=C1c2c(ccc(O)c2F)CN1C[C@H]1CC[C@H](C(=O)O)CC1]

Trans-4-((7-fluoro-6-hydroxy-1-oxoisoindolin-2-yl)methyl)cyclohexanecarboxylic acid (3-1)

3-1 was prepared from 1-10 by a procedure analogous to that used in the synthesis of 1-12.

Example 24

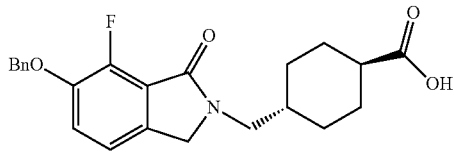 [SMILES: O=C1c2c(ccc(OCc3ccccc3)c2F)CN1C[C@H]1CC[C@H](C(=O)O)CC1]

Trans-4-((6-(benzyloxy)-7-fluoro-1-oxoisoindolin-2-yl)methyl)cyclohexanecarboxylic acid (3-2)

A mixture of 3-1 (1.65 g, 5.4 mmol), anhydrous cesium carbonate (12.6 g, 37.8 mmol) and benzyl bromide (2.04

Example 27

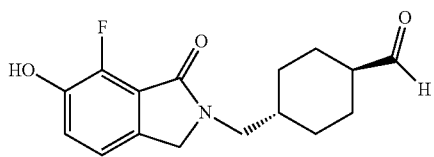 [SMILES: O=C[C@H]1CC[C@H](CN2Cc3ccc(O)c(F)c3C2=O)CC1]

Trans-4-((7-fluoro-6-hydroxy-1-oxoisoindolin-2-yl)methyl)cyclohexanecarbaldehyde (3-5)

To a stirred mixture of pyridinium chlorochromate (21 mg, 0.1 mmol) and silica gel (21 mg) in DCM/THF (1 mL/1 mL) was added dropwise a solution of 3-4 (10 mg, 0.034 mmol) in DCM/THF (0.5 mL/0.5 mL) at rt. After the mixture was stirred for 40 min, additional pyridinium chlorochromate (14 mg, 0.066 mmol) was added. The reaction mixture was stirred for one more hour and ether (4 mL) added. The mixture was filtered through a short pad of Celite and the Celite washed with EtOAc (5×2 mL). The filtrate and the washings were combined, filtered through a column of silica gel and the column washed with EtOAc thoroughly. The filtrate was evaporated under reduced pressure to yield 3-5 as an off-yellow residue (5 mg, 50% yield). HPLC 90% pure.

Example 28

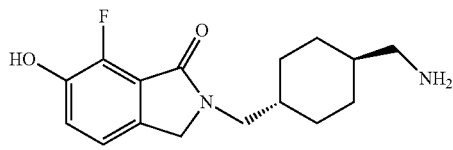 [SMILES: NC[C@H]1CC[C@H](CN2Cc3ccc(O)c(F)c3C2=O)CC1]

2-((Trans-4-(aminomethyl)cyclohexyl)methyl)-7-fluoro-6-hydroxyisoindolin-1-one (3-6)

3-6 was prepared from 3-5 by a procedure analogous to that used in the synthesis of 2-1. HPLC 97% pure.

Example 29

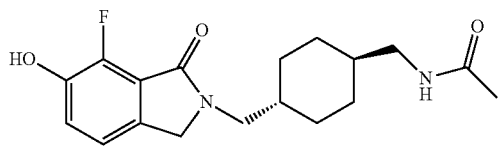 [SMILES: CC(=O)NC[C@H]1CC[C@H](CN2Cc3ccc(O)c(F)c3C2=O)CC1]

N-((Trans-4-((7-fluoro-6-hydroxy-1-oxoisoindolin-2-yl)methyl)cyclohexyl)methyl)acetamide (3-7)

3-7 was prepared from 3-6 by a procedure analogous to that used in the synthesis of 2-2. HPLC >99% pure; MS m/e 333 (M−H).

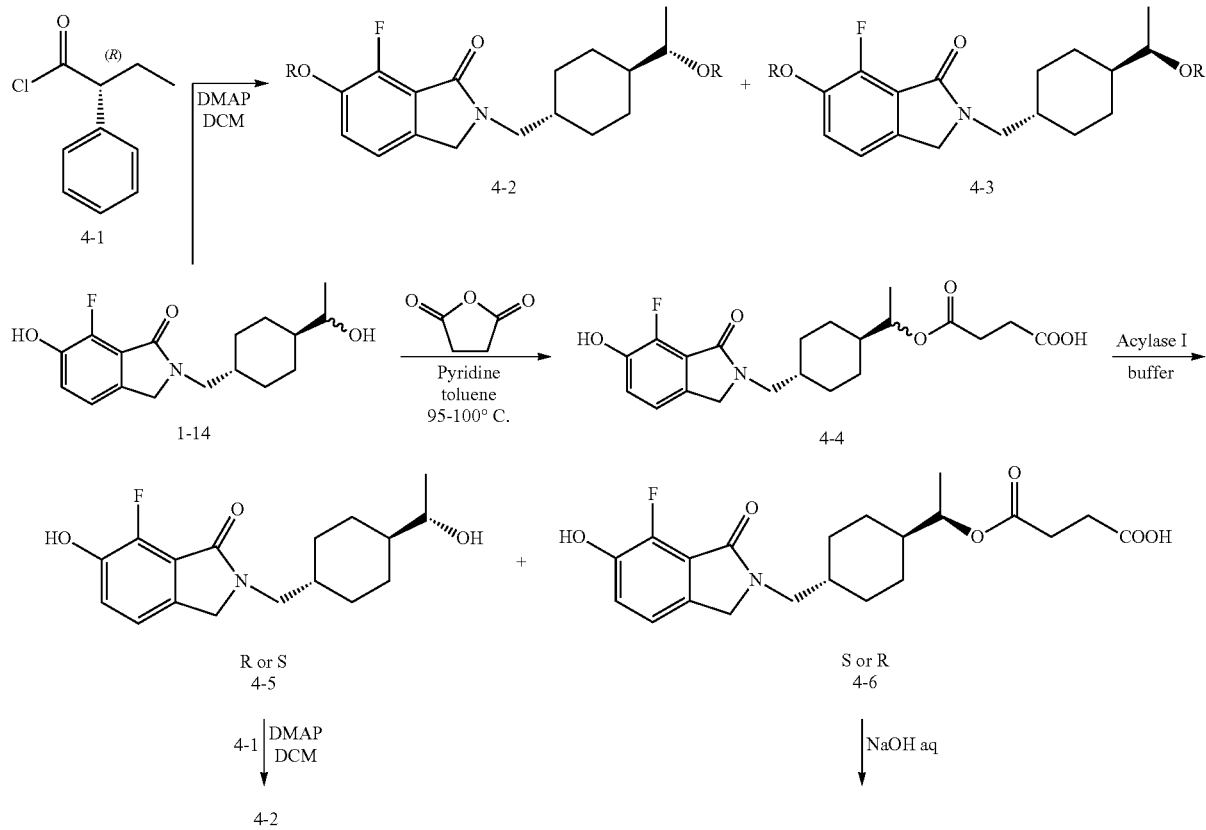

REACTION SCHEME 4

-continued

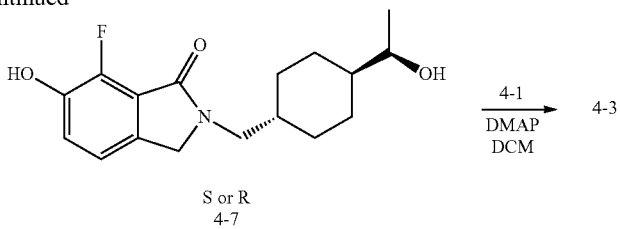

S or R
4-7

Example 30

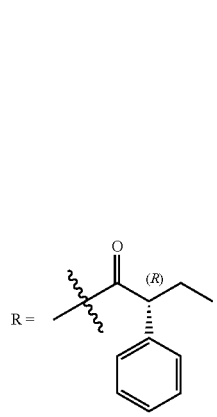

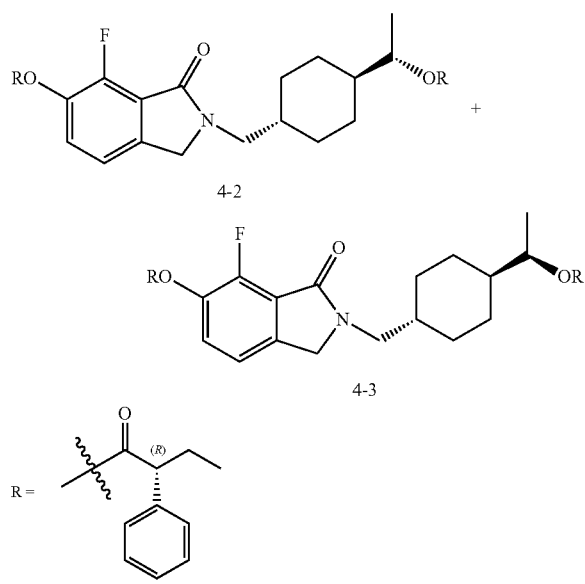

A Diastereoisomeric Mixture (4-2 & 4-3)

To a stirred mixture of (R)-(−)-2-phenylbutyric acid (0.14 mL, 0.15 g, 0.92 mmol) in 5 mL of DCM and 2.5 mL of toluene was added oxalyl chloride (0.14 mL, 2.1 mmol) and a drop of DMF. The mixture was stirred at rt for 2.5 h and then concentrated, taken up in DCM (3 mL) and the solvent evaporated to yield (R)-(−)-2-phenylbutyric acid chloride (4-1) as a yellow oil (170 mg, 0.92 mmol).

To a solution of 1-14 (<1 mg, <3.3 μmol) in DCM (0.2 mL) were added DMAP (2 mg, 16 μmol) and 4-1 (6 μL, ~33 μmol). After the mixture was stirred for 4 h at rt, HPLC analysis (Column: Phenomenex C18, 100×4.60 mm; Gradient: A/B (20%/80%) maintained for 6 min and then changed to A/B (0%/100%) over 5 minutes, A=0.07% TFA-H$_2$O, B=0.07% TFA-MeCN) showed 1-14 was consumed completely to yield two new peaks at 6.292 min and 6.411 min with a 59/41 ratio when integrated at 230 nm, which indicated a diastereoisomeric mixture of 4-2 & 4-3.

Example 31

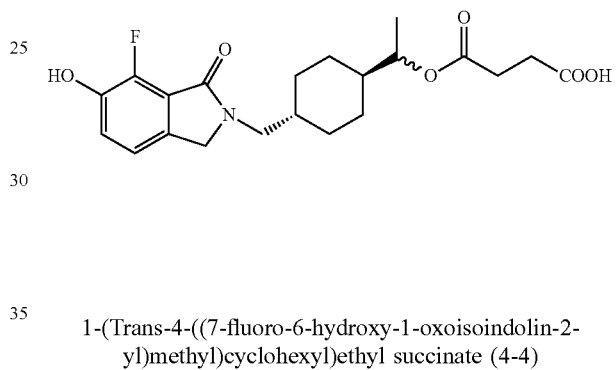

1-(Trans-4-((7-fluoro-6-hydroxy-1-oxoisoindolin-2-yl)methyl)cyclohexyl)ethyl succinate (4-4)

To a stirred mixture of 1-14 (370 mg, 1.21 mmol) in 3 mL of toluene were added pyridine (35 mL, 47.2 mmol) and succinic anhydride (2.4 g, 24 mmol) under argon. The mixture was stirred at 100-110° C. for 44 h and the reaction mixture cooled to rt. 3 N HCl (13 mL, 39 mmol) was added and the mixture stirred for 10 min before more 3 N HCl was added to adjust the pH to 1-2. The solution was extracted with EtOAc (5×30 mL) and the combined organic phases were washed with 1 N HCl (2×30 mL), dried over sodium sulfate, filtered, concentrated, and purified by flash chromatography on silica gel (EtOAc/MeOH=10/1) to yield 4-4 as a slightly yellow solid (450 mg, 91% yield). HPLC >99% pure; MS m/e 406 (M−H).

Example 32

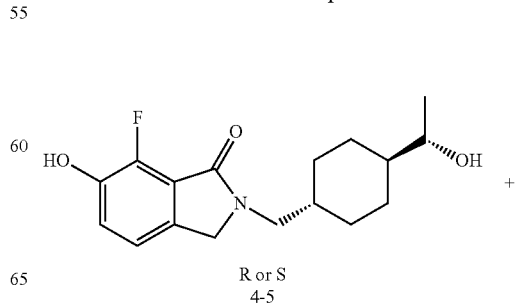

R or S
4-5

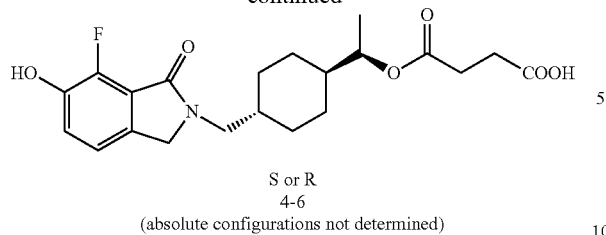

S or R
4-6
(absolute configurations not determined)

4-4 (4.8 mg) was dissolved in 3.6 mL of Tris/HCl buffer (70 mM, pH-8.48) in an 8-mL glass vial. 4-4 (4.8 mg) was dissolved in 3.6 mL of phosphate buffer (50 mM, pH-8.48) in another 8-mL glass vial. The resulting two solutions were purged with argon and Acylase I (Sigma, from Porcine Kidney, 3,050 units/mg solid) (8.5 mg) was added to each solution. The resultant two mixtures were stirred at 40° C. and monitored by HPLC. After 60 h, HPLC analysis indicated 48-50% of 4-4 in each mixture was converted to a new peak. The two mixtures were cooled to rt, combined, and extracted with EtOAc (2×6 mL). The EtOAc extracts were combined, concentrated and purified by flash chromatography on silica gel (EtOAc/MeOH=10/1, then EtOAc/MeOH/AcOH=100/10/1) to yield 4-5 (R or S, 2.35 mg, >99% pure on HPLC) and 4-6 (S or R, 1.1 mg, >99% pure on HPLC) along with a mixture of 4-5/4-6 (16/84). When 4-5 (<1 mg) was treated with a procedure analogous to that used in the synthesis of 4-2 & 4-3 mixture, HPLC analysis (Column: Phenomenex C18, 100×4.60 mm; Gradient: A/B (20%/80%) maintained for 6 min and then changed to A/B (0%/100%) over 5 minutes, A=0.07% TFA-H$_2$O, B=0.07% TFA-MeCN) of the quenched reaction mixture showed 4-5 was consumed completely to yield only one peak at 6.298 min (corresponded to the first peak of the 4-2 & 4-3 mixture under the same HPLC conditions), which indicated 4-5 as an optically pure enantiomer although the absolute configuration was not determined.

Example 33

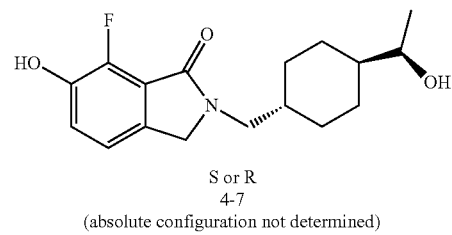 [SMILES: C[C@@H](O)[C@H]1CC[C@H](CN2Cc3ccc(O)c(F)c3C2=O)CC1]

S or R
4-7
(absolute configuration not determined)

4-6 (~1 mg) was stirred in 0.1 N NaOH (0.5 mL) for 40 min at rt and 2 h in a hot water bath (30-40° C.). The reaction mixture was acidified to pH 2, extracted with EtOAc (3×2 mL), and the combined EtOAc extracts were dried over sodium sulfate, filtered, and concentrated to yield 4-7 (0.73 mg, >99% pure on HPLC).

When 4-7 (<1 mg) was treated with a procedure analogous to that used in the synthesis of 4-2 & 4-3 mixture, HPLC analysis (Column: Phenomenex C18, 100×4.60 mm; Gradient: A/B (20%/80%) maintained for 6 min and then changed to A/B (0%/100%) over 5 minutes, A=0.07% TFA-H$_2$O, B=0.07% TFA-MeCN) of the quenched reaction mixture showed 4-7 was consumed completely to yield only one peak at 6.472 min (corresponded to the second peak of the 4-2 & 4-3 mixture under the same HPLC conditions), which indicated 4-7 as an optically pure enantiomer although the absolute configuration was not determined.

REACTION SCHEME 5

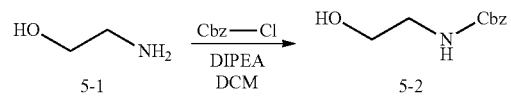

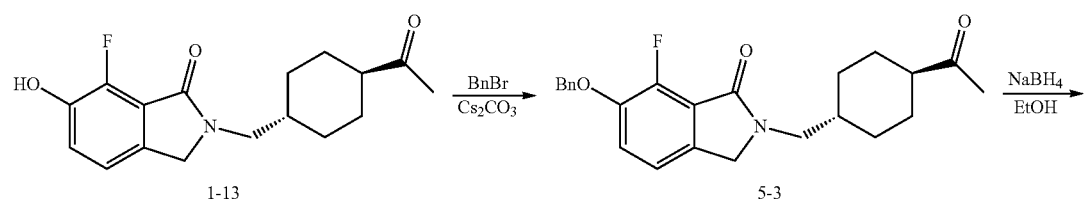

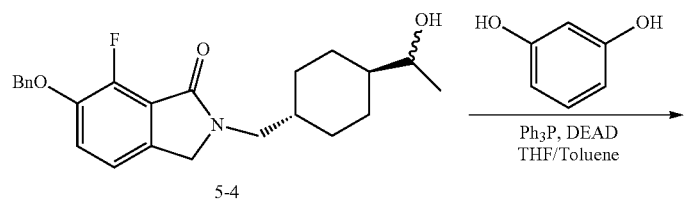

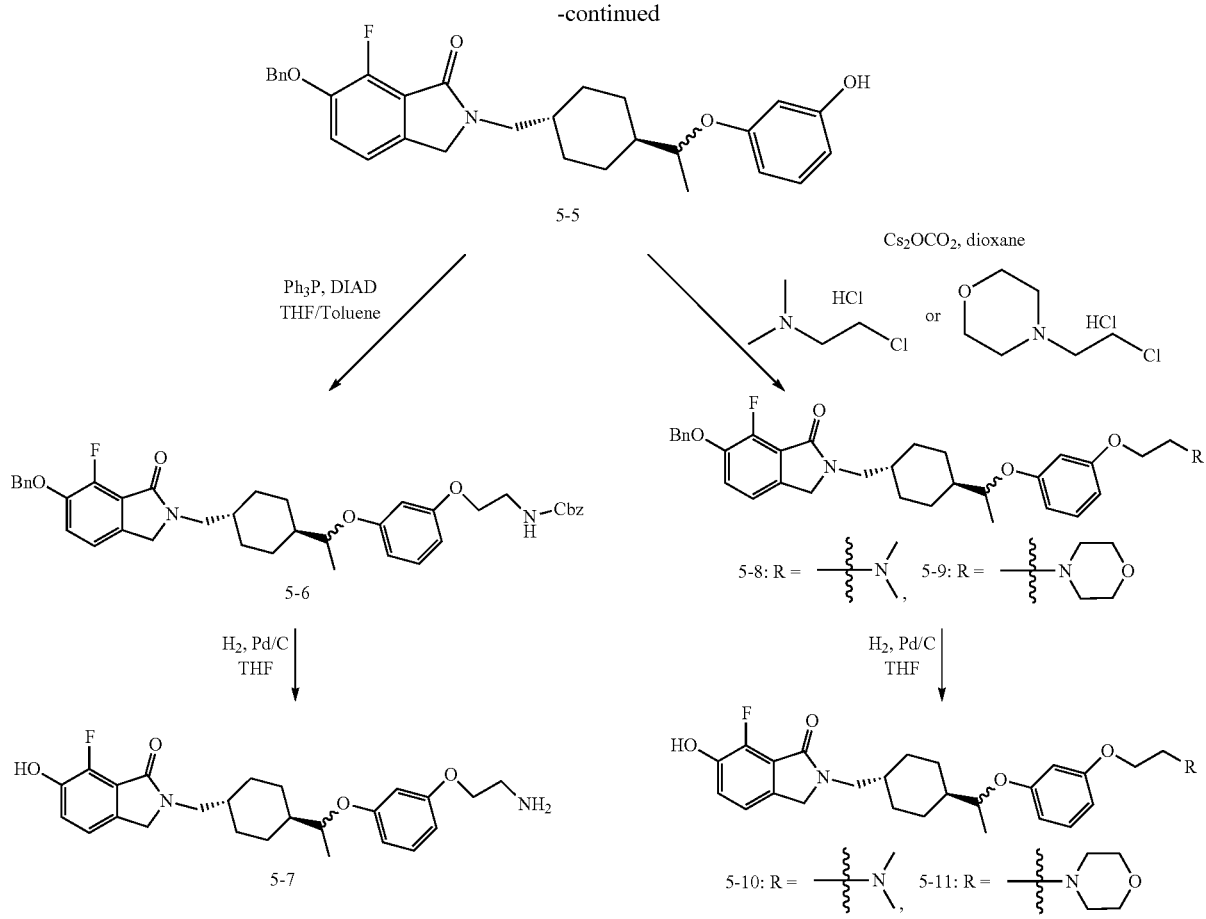

Example 34

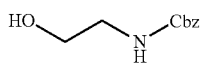

Benzyl 2-hydroxyethylcarbamate (5-2)

To a cooled solution (0° C.) of ethanolamine (5-1) (0.6 mL, 10 mmol, 1.0 eq) in DCM (15 mL) were slowly added Cbz-Cl (1.35 mL, 12 mmol, 1.2 eq) and DIPEA (1.09 mL, 12 mmol, 1.2 eq). The mixture was allowed to warm to rt over 3 h and kept at rt for 1 h before quenching with 1 N HCl (20 mL). The separated DCM layer was washed with 1 N HCl (15 mL) and the combined aqueous phases were extracted with DCM (15 mL). The organic phases were combined, dried over sodium sulfate and concentrated. The residue (~2 g) was taken up in EtOAc (~3 mL) and mixed with hexane (~15 mL) to precipitate out a solid, which was collected via vacuum filtration and washed with hexane to yield 5-2 as a white solid (1.48 g, 76% yield). HPLC >99% pure.

Example 35

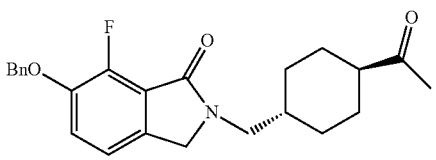 [SMILES: CC(=O)[C@H]1CC[C@H](CN2Cc3ccc(OCc4ccccc4)c(F)c3C2=O)CC1]

2-((Trans-4-acetylcyclohexyl)methyl)-6-(benzyloxy)-7-fluoroisoindolin-1-one (5-3)

5-3 was prepared from 1-13 and benzyl bromide by a procedure analogous to the first step used in the synthesis of 3-2.

Example 36

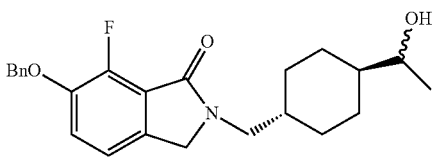 [SMILES: CC(O)[C@H]1CC[C@H](CN2Cc3ccc(OCc4ccccc4)c(F)c3C2=O)CC1]

6-(Benzyloxy)-7-fluoro-2-((trans-4-(1-hydroxyethyl) cyclohexyl)methyl)isoindolin-1-one (5-4)

5-4 was prepared from 5-3 by a procedure analogous to that used in the synthesis of 1-14. HPLC >99% pure.

Example 37

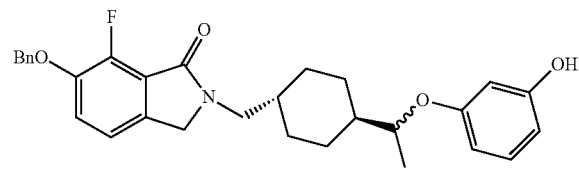 [SMILES: CC(Oc1cccc(O)c1)[C@H]1CC[C@H](CN2Cc3ccc(OCc4ccccc4)c(F)c3C2=O)CC1]

2-((Trans-4-(1-(3-hydroxyphenoxyl)ethyl)cyclohexyl)methyl)-6-(benzyloxy)-7-fluoroisoindolin-1-one (5-5)

To a solution of 5-4 (80 mg, 0.2 mmol) in 4 mL of dry THF under argon at rt were added resorcinol (110 mg, 1 mmol), Ph$_3$P (157 mg, 0.6 mmol) followed by a 40% wt solution of DEAD in toluene (285 µL, 0.6 mmol) dropwise. After the reaction was stirred overnight, the mixture was concentrated and purified by flash chromatography on silica gel (hexane/EtOAc=2/1, 3/2 then 1/1) to yield 5-5 (48 mg, 49% yield). HPLC 95% pure.

Example 38

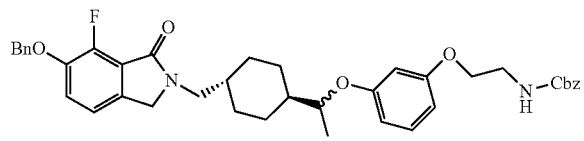 [SMILES: CC(Oc1cccc(OCCNC(=O)OCc2ccccc2)c1)[C@H]1CC[C@H](CN2Cc3ccc(OCc4ccccc4)c(F)c3C2=O)CC1]

2-((Trans-4-(1-(3-(2-N-Cbz-aminoethoxy)phenoxy) ethyl)cyclohexyl)methyl)-6-(benzyloxy)-7-fluoroisoindolin-1-one (5-6)

5-5 (20 mg, 0.041 mmol) was taken up in anhydrous THF (1 mL) and to this were added under argon at rt 5-2 (96 mg, 0.49 mmol), Ph$_3$P (106 mg, 0.392 mmol) followed by diisopropyl azodicarboxylate (41 µL, 0.196 mmol) dropwise. After 0.5 h, additional diisopropyl azodicarboxylate (41 µL, 0.196 mmol) was added dropwise. The reaction was stirred for 64 h and then concentrated. The residue was purified by flash chromatography on silica gel (hexane/EtOAc=2/1 to 1/1) to yield 5-6 (15 mg, 55% yield). HPLC 93% pure.

Example 39

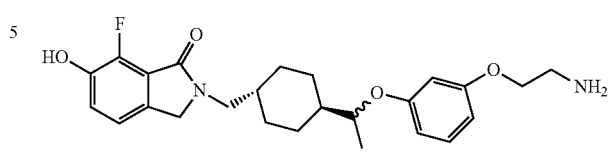

2-((Trans-4-(1-(3-(2-aminoethoxyl)phenoxy)ethyl) cyclohexyl)methyl)-7-fluoro-6-hydroxyisoindolin-1-one (5-7)

5-7 was prepared from 5-6 by a procedure analogous to that used in the synthesis of 3-4. HPLC 96% pure; MS m/e 465 (M+Na).

Example 40

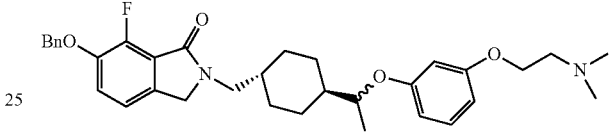

2-((Trans-4-(1-(3-(2-(dimethylamino)ethoxy)phenoxy)ethyl)cyclohexyl)methyl)-6-(benzyloxy)-7-fluoroisoindolin-1-one (5-8)

To a solution of 5-5 (3-4 mg, <0.008 mmol) in 1,4-dioxane (4 mL) were added under argon at rt anhydrous cesium carbonate (80 mg, 0.24 mmol) and dimethylaminoethylchloride hydrochloride (34 mg, 0.24 mmol). After the mixture was stirred at 100° C. for 1.5 h, it was cooled to rt, filtered, and the solids in the filter washed with DCM (2×10 mL). The filtrate and the washings were combined, concentrated, taken up in ether (4 mL), and extracted with 0.5 N HCl (3×2 mL). The combined aqueous phases were basified to pH 12 and extracted with DCM (3×3 mL). The combined DCM extracts were dried over sodium sulfate, filtered and concentrated to yield 5-8 (2 mg).

Example 41

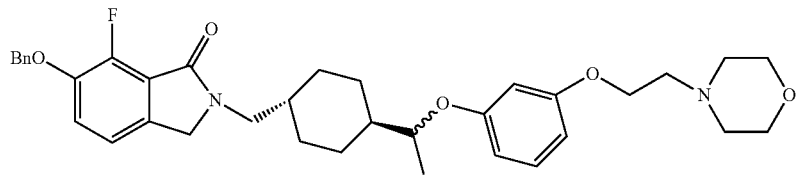 [SMILES: CC(Oc1cccc(OCCN2CCOCC2)c1)[C@H]1CC[C@H](CN2Cc3ccc(OCc4ccccc4)c(F)c3C2=O)CC1]

2-((Trans-4-(1-(3-(2-morpholinoethoxyl)phenoxy) ethyl)cyclohexyl)methyl)-6-(benzyloxy)-7-fluoroisoindolin-1-one (5-9)

5-9 was prepared from 5-5 by a procedure analogous to that used in the synthesis of 5-8 except that N-(2-chloroethyl) morpholine hydrochloride was used in place of dimethylaminoethylchloride hydrochloride.

Example 42

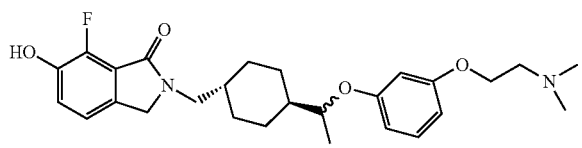 [SMILES: CC(Oc1cccc(OCCN(C)C)c1)[C@H]1CC[C@H](CN2Cc3ccc(O)c(F)c3C2=O)CC1]

2-((Trans-4-(1-(3-(2-(dimethylamino)ethoxy)phenoxy)ethyl)cyclohexyl)methyl)-7-fluoro-6-hydroxy-isoindolin-1-one (5-10)

5-10 was prepared from 5-8 by a procedure analogous to that used in the synthesis of 3-4. HPLC >99% pure; MS m/e 471 (M+H).

Example 43

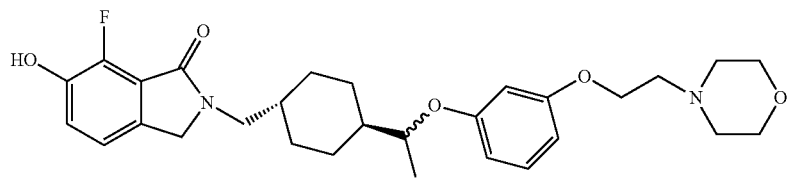 [SMILES: CC(Oc1cccc(OCCN2CCOCC2)c1)[C@H]1CC[C@H](CN2Cc3ccc(O)c(F)c3C2=O)CC1]

2-((Trans-4-(1-(3-(2-morpholinoethoxyl)phenoxy)ethyl)cyclohexyl)methyl)-7-fluoro-6-hydroxyisoindolin-1-one (5-11)

5-11 was prepared from 5-9 by a procedure analogous to that used in the synthesis of 3-4. HPLC >99% pure; MS m/e 511 (M−H).

REACTION SCHEME 6

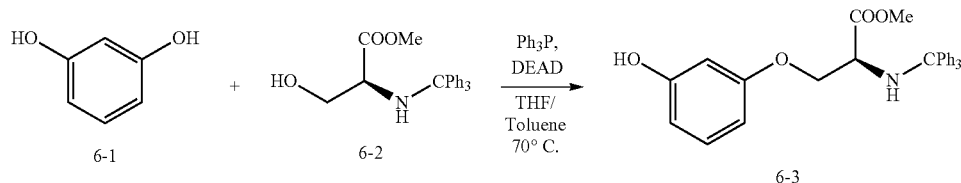

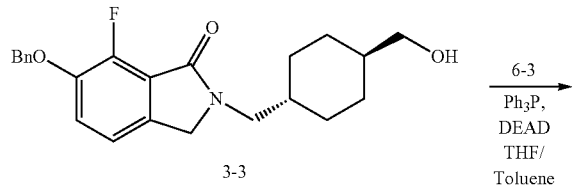

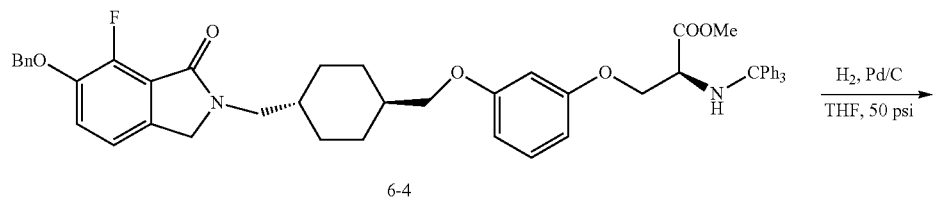

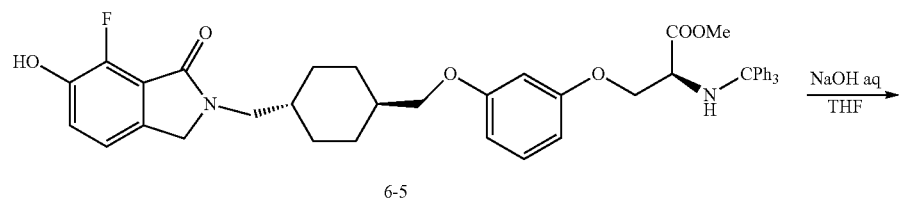

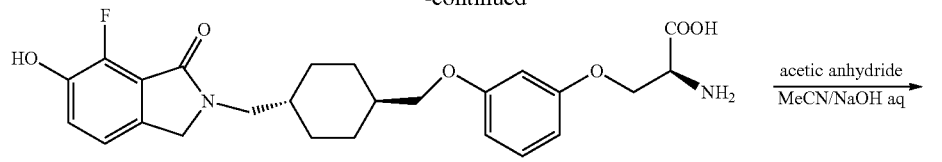

6-6

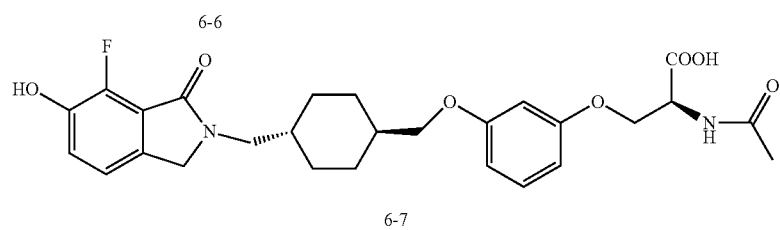

6-7

Example 44

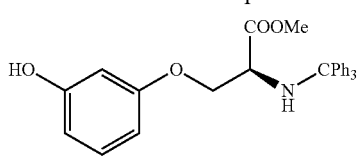

(S)-methyl 3-(3-hydroxyphenoxy)-2-(tritylamino) propanoate (6-3)

To a solution of resorcinol (6-1) (550 mg, 5 mmol), N-trityl-L-serine methyl ester (6-2) (2.7 g, 7.5 mmol), and triphenylphosphine (1.97 g, 7.5 mmol) in toluene (15 mL) under an argon atmosphere was slowly added a solution of DEAD in toluene (40%, 519 μL, 1.1 mmol) at 70° C. The mixture was stirred at 70° C. for 4.5 h and at rt overnight. The reaction mixture was concentrated and purified by flash chromatography on silica gel (hexane/EtOAc=5/1, 2/1, then 1/1) to yield 6-3 (1 g, 44% yield). HPLC 90% pure.

Example 45

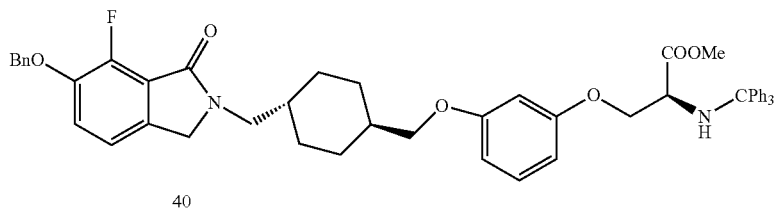

O-(3-(1-(Trans-4-((7-fluoro-6-benzyloxy-1-oxoisoindolin-2-yl)methyl)cyclohexyl)methoxy)phenyl)-N-trityl-L-serine methyl ester (6-4)

To a solution of 3-3 (20 mg, 0.052 mmol) in 0.5 mL of anhydrous THF under argon at rt were added 6-3 (226 mg, 0.5 mmol), Ph₃P (68 mg, 0.26 mmol) followed by a 40 wt % solution of DEAD in toluene (124 μL, 0.26 mmol) dropwise. After the mixture was stirred for 17 h, the mixture was concentrated and purified by flash chromatography on silica gel (hexane/EtOAc=2/1 to 1/1) to yield 6-4 (27 mg, 63% yield). HPLC 95% pure.

Example 46

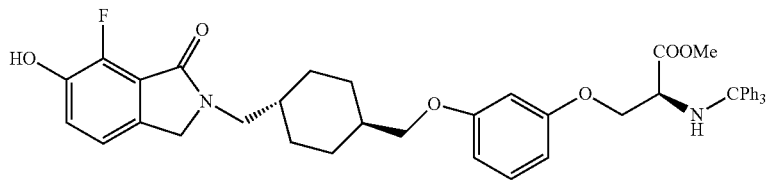

O-(3-(1-(Trans-4-((7-fluoro-6-hydroxy-1-oxoisoindolin-2-yl)methyl)cyclohexyl)methoxy)phenyl)-N-trityl-L-serine methyl ester (6-5)

6-5 was prepared from 6-4 by a procedure analogous to that used in the synthesis of 3-4. HPLC 95% pure.

Example 47

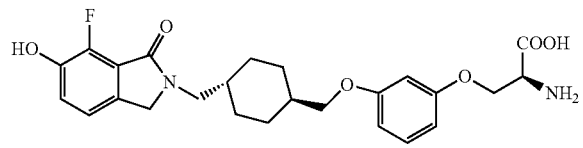 [SMILES: N[C@@H](COc1cccc(OC[C@H]2CC[C@H](CN3Cc4ccc(O)c(F)c4C3=O)CC2)c1)C(=O)O]

O-(3-(1-(Trans-4-((7-fluoro-6-hydroxy-1-oxoisoindolin-2-yl)methyl)cyclohexyl)methoxy)phenyl)-L-serine (6-6)

6-5 (20 mg, 0.027 mmol) was stirred in THF (1 mL) and 0.1 N NaOH (4 mL) at rt for 2 h and the reaction mixture washed with ether (2×2 mL). The separated aqueous phase was acidified to pH 3-4 with minimum amount of 2 N HCl and extracted with ether (3×3 mL). The ether extracts were combined, dried over $Na_2SO_4$, filtered, and concentrated to yield crude 6-6 (12 mg, 94% yield). The crude 6-6 (1-2 mg) was subjected to reverse phase C-18 silica gel chromatography using a gradient of 0-100% MeCN in 0.07% aqueous TFA as eluent. Evaporation of the eluent from the collected fractions containing 6-6 afforded pure 6-6 (1-2 mg). HPLC >99% pure; MS m/e 471 (M−H).

Example 48

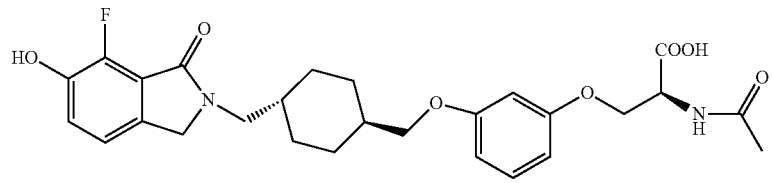 [SMILES: CC(=O)N[C@@H](COc1cccc(OC[C@H]2CC[C@H](CN3Cc4ccc(O)c(F)c4C3=O)CC2)c1)C(=O)O]

O-(3-(1-(Trans-4-((7-fluoro-6-hydroxy-1-oxoisoindolin-2-yl)methyl)cyclohexyl)methoxy)phenyl)-N-acetyl-L-serine (6-7)

To a solution of 6-6 (1-2 mg) in MeCN (1 mL) were added 0.2 N NaOH (1 mL) and acetic anhydride (6 µL). After the mixture was stirred for 50 min, the reaction mixture was acidified to pH 1 and extracted with DCM (3×2 mL). The combined DCM phases were dried over sodium sulfate, filtered and concentrated to yield 6-7 (~1 mg). HPLC 97% pure; MS m/e 513 (M−H).

REACTION SCHEME 7

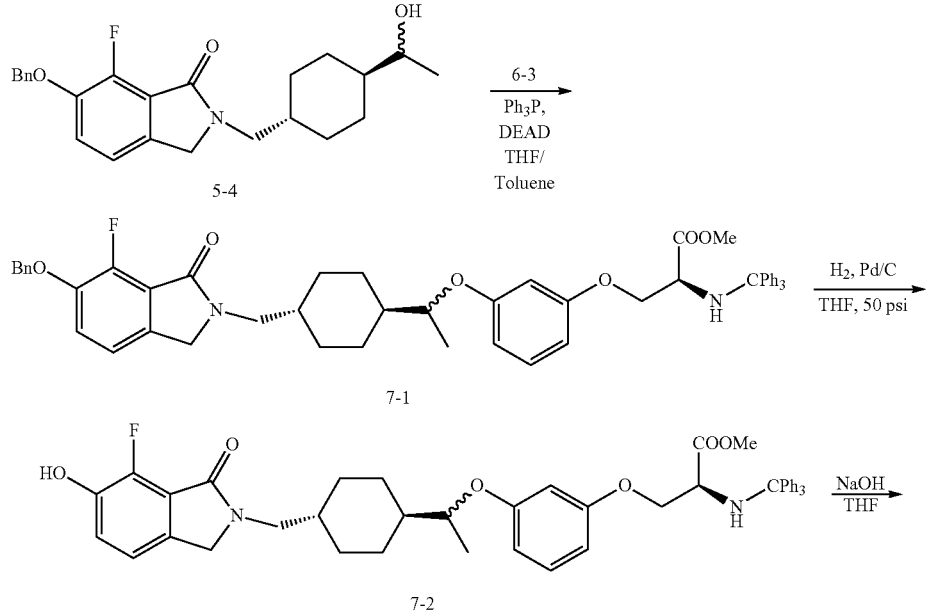

-continued

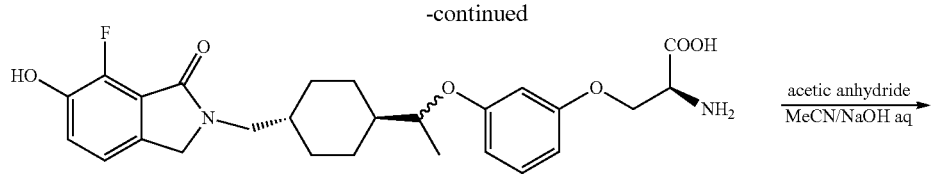

7-3

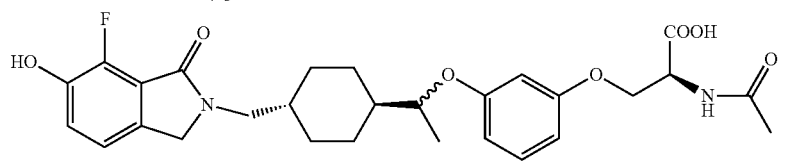

7-4

Example 49

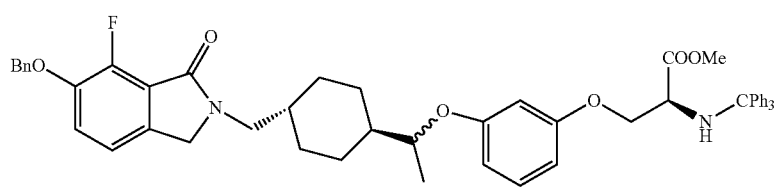

O-(3-(1-(Trans-4-((7-fluoro-6-benzyloxy-1-ox-oisoindolin-2-yl)methyl)cyclohexyl)ethoxy)phenyl)-N-trityl-L-serine methyl ester (7-1)

7-1 was prepared from 5-4 and 6-3 by a procedure analogous to that used in the synthesis of 6-4. HPLC 90% pure.

Example 50

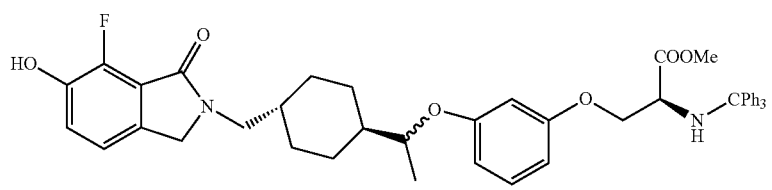

O-(3-(1-(Trans-4-((7-fluoro-6-hydroxy-1-oxoisoindolin-2-yl)methyl)cyclohexyl)ethoxy)phenyl)-N-trityl-L-serine methyl ester (7-2)

7-2 was prepared from 7-1 by a procedure analogous to that used in the synthesis of 3-4.

Example 51

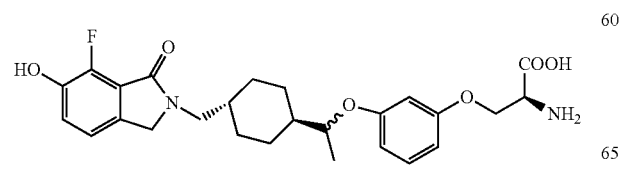

O-(3-(1-(Trans-4-((7-fluoro-6-hydroxy-1-oxoisoin-dolin-2-yl)methyl)cyclohexyl)ethoxy)phenyl)-L-serine (7-3)

7-3 was prepared from 7-2 by a procedure analogous to that used in the synthesis of 6-6. HPLC >99% pure; MS m/e 485 (M−H).

Example 52

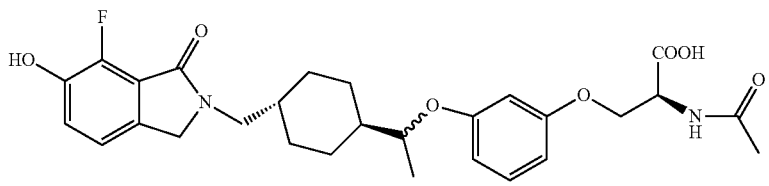 [SMILES: CC(=O)N[C@@H](COc1cccc(OC(C)[C@H]2CC[C@H](CN3Cc4ccc(O)c(F)c4C3=O)CC2)c1)C(=O)O]

O-(3-(1-(Trans-4-((7-fluoro-6-hydroxy-1-oxoisoin-dolin-2-yl)methyl)cyclohexyl)ethoxy)phenyl)-N-acetyl-L-serine (7-4)

7-4 was prepared from 7-3 by a procedure analogous to that used in the synthesis of 6-7. HPLC 96% pure; MS m/e 527 (M−H).

REACTION SCHEME 8

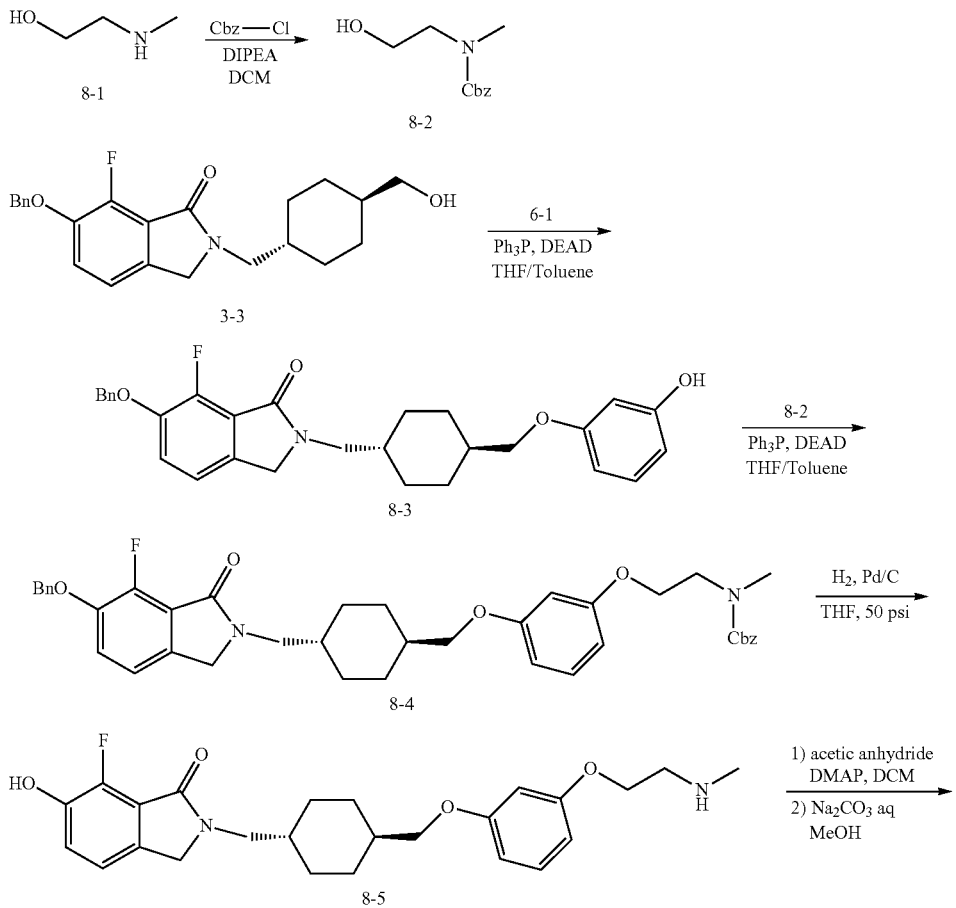

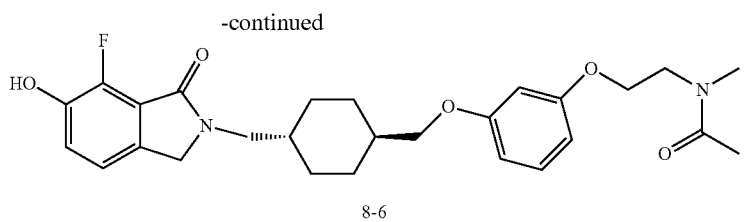

8-6

Example 53

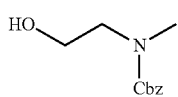

Benzyl 2-hydroxyethylmethylcarbamate (8-2)

8-2 was prepared from 8-1 by a procedure analogous to that used in the synthesis of 5-2.

Example 54

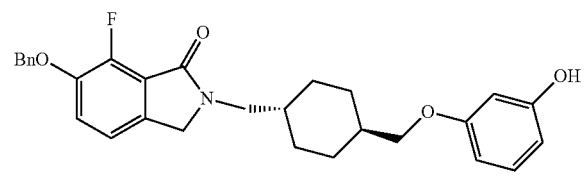 [SMILES: O=C1c2c(ccc(OCc3ccccc3)c2F)CN1C[C@H]1CC[C@H](COc2cccc(O)c2)CC1]

2-((Trans-4-((3-hydroxyphenoxy)methyl)cyclohexyl)methyl)-6-(benzyloxy)-7-fluoroisoindolin-1-one (8-3)

8-3 was prepared from 3-3 and 6-1 (resorcinol) by a procedure analogous to that used in the synthesis of 5-5.

Example 55

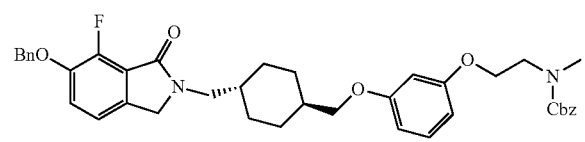 [SMILES: CN(CCOc1cccc(OC[C@H]2CC[C@H](CN3Cc4ccc(OCc5ccccc5)c(F)c4C3=O)CC2)c1)C(=O)OCc1ccccc1]

2-((Trans-4-(1-(3-(2-N-Cbz-N-methyl-aminoethoxy)phenoxy)methyl)cyclohexyl)methyl)-6-(benzyloxy)-7-fluoroisoindolin-1-one (8-4)

8-4 was prepared from 8-3 and 8-2 by a procedure analogous to that used in the synthesis of 5-6.

Example 56

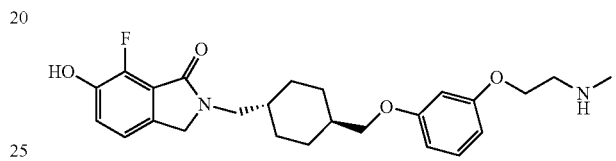

2-((Trans-4-(1-(3-(2-N-methyl-aminoethoxy)phenoxy)methyl)cyclohexyl)methyl)-6-(hydroxy)-7-fluoroisoindolin-1-one (8-5)

8-5 was prepared from 8-4 by a procedure analogous to that used in the synthesis of 3-4. HPLC 98% pure.

Example 57

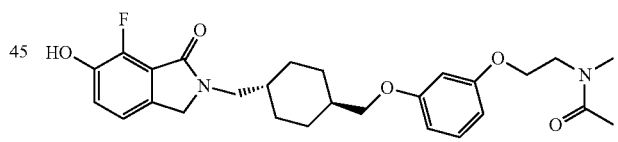

2-((Trans-4-(1-(3-(2-N-acetyl-N-methyl-aminoethoxy)phenoxy)methyl)cyclohexyl)methyl)-6-(hydroxy)-7-fluoroisoindolin-1-one (8-6)

To a solution of 8-5 (<1 mg) in DCM (0.3 mL) were added Et$_3$N (10 μL), acetic anhydride (5 μL), and DMAP (2 mg). The reaction mixture was stirred for 1 h at rt, washed with 1 N HCl (1.5 mL) and then concentrated. The residue was stirred in saturated Na$_2$CO$_3$ (200 μL) and MeOH (100 μL) for 3 h and then acidified to pH 1. The acidic solution was subjected to reverse phase C-18 silica gel chromatography using a gradient of 0-100% MeCN in 0.07% aqueous TFA as eluent. Evaporation of the eluent from the collected fractions containing 8-6 afforded pure 8-6 (<1 mg). HPLC >99% pure; MS m/e 485 (M+H).

REACTION SCHEME 9
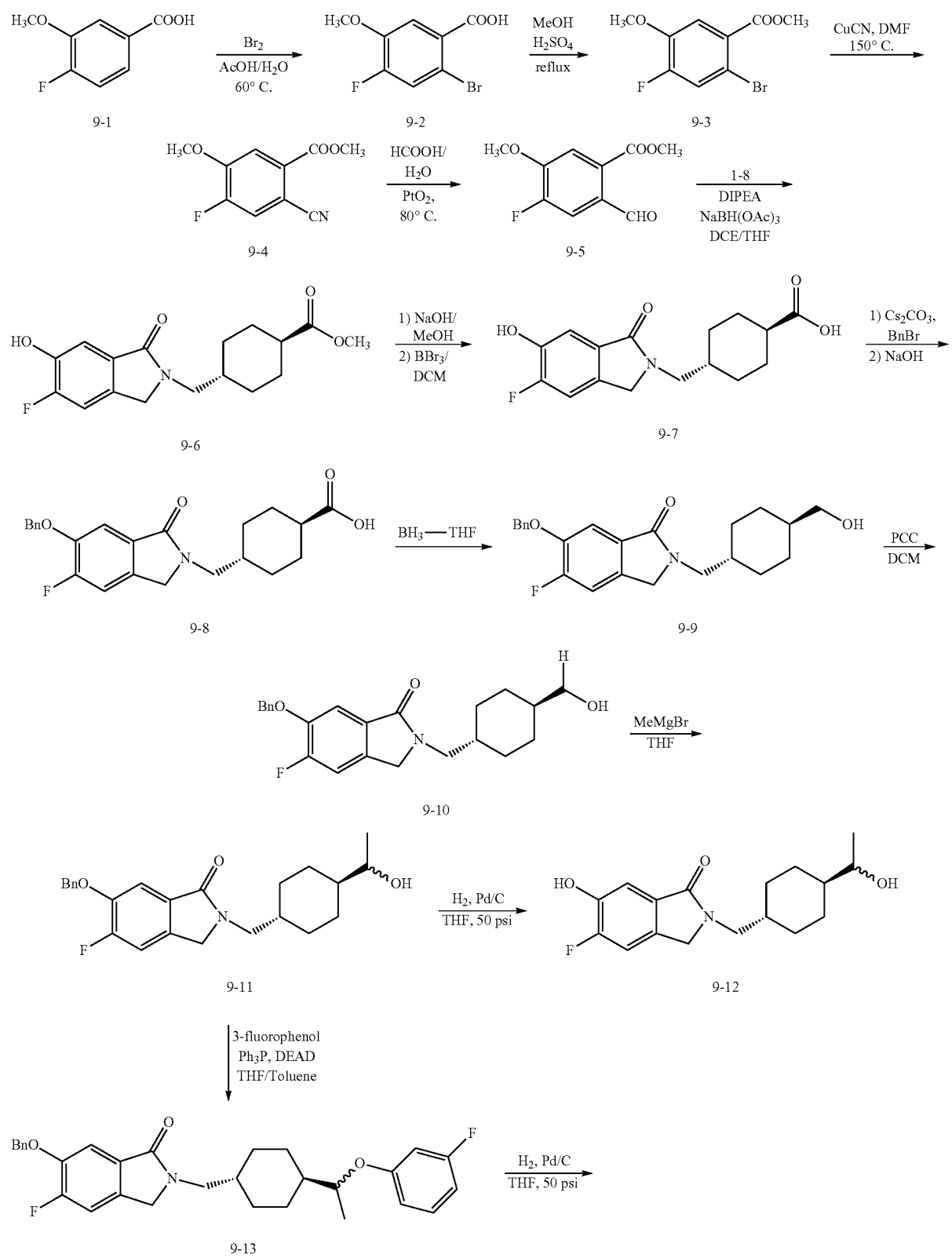

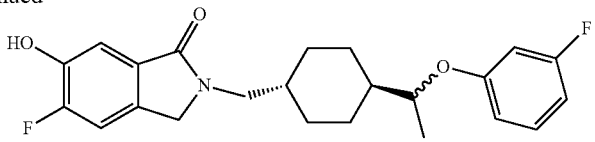

9-14

Example 58

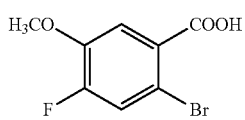

2-Bromo-4-fluoro-5-methoxybenzoic acid (9-2)

Compound 9-2 was prepared from 9-1 (Sigma) by a procedure similar to that described in PCT Int. Appl. 2008020306.

Example 59

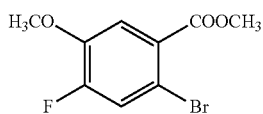

Methyl 2-bromo-4-fluoro-5-methoxybenzoate (9-3)

A solution of 9-2 (1 g, 4.03 mmol) and 96% $H_2SO_4$ (0.65 mL, 13 mmol) in dry MeOH (15 mL) was refluxed for 7.5 h and cooled to rt. MeOH was evaporated and the residue taken up in DCM (15 mL), washed with saturated sodium bicarbonate (15 mL). The separated aqueous phase (final pH 7.5-8) was extracted with DCM (2×10 mL) and the organic phases were combined and washed with water (15 mL). The resulting organic phase was dried over sodium sulfate, concentrated to yield 9-3 as a solid (1.06 g, 100% yield). HPLC 98% pure.

Example 60

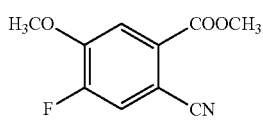

Methyl 2-cyano-4-fluoro-5-methoxybenzoate (9-4)

Compound 9-4 was prepared from 9-3 by a procedure similar to that described in PCT Int. Appl. 2008020306.

Example 61

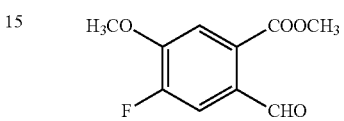

Methyl 4-fluoro-2-formyl-5-methoxybenzoate (9-5)

Compound 9-5 was prepared from 9-4 by a procedure similar to that used in the synthesis of 1-6.

Example 62

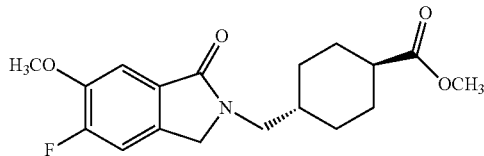 [SMILES: COc1cc2c(cc1F)CN(C[C@H]1CC[C@H](C(=O)OC)CC1)C2=O]

Trans-methyl 4-((5-fluoro-6-methoxy-1-oxoisoindolin-2-yl)methyl)cyclohexanecarboxylate (9-6)

Compound 9-6 was prepared from 9-5 and 1-8 by a procedure similar to that used in the synthesis of 1-9.

Example 63

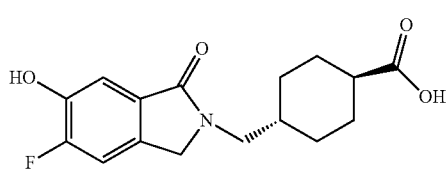 [SMILES: O=C1c2cc(O)c(F)cc2CN1C[C@H]1CC[C@H](C(=O)O)CC1]

Trans-4-((5-fluoro-6-hydroxy-1-oxoisoindolin-2-yl)methyl)cyclohexanecarboxylic acid (9-7)

Compound 9-7 was prepared from 9-6 by a hydrolysis step (a procedure similar to that used in the synthesis of 1-10) followed by a demethylation step (a procedure similar to that used in the synthesis of 1-12).

Example 64

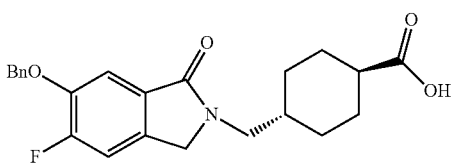 [SMILES: O=C1c2cc(OCc3ccccc3)c(F)cc2CN1C[C@H]1CC[C@H](C(=O)O)CC1]

Trans-4-((6-(benzyloxy)-5-fluoro-1-oxoisoindolin-2-yl)methyl)cyclohexanecarboxylic acid (9-8)

Compound 9-8 was prepared from 9-7 by a procedure similar to that used in the synthesis of 3-2.

Example 65

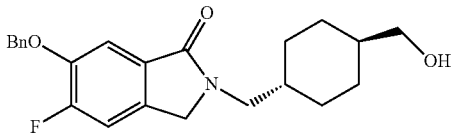 [SMILES: O=C1c2cc(OCc3ccccc3)c(F)cc2CN1C[C@H]1CC[C@H](CO)CC1]

6-(Benzyloxy)-5-fluoro-2-((trans-4-(hydroxymethyl)cyclohexyl)methyl)isoindolin-1-one (9-9)

Compound 9-9 was prepared from 9-8 by a procedure similar to that used in the synthesis of 3-3.

Example 66

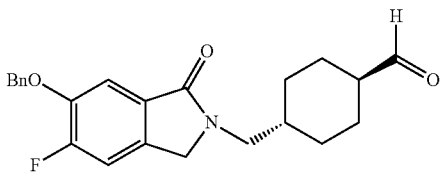 [SMILES: O=C[C@H]1CC[C@H](CN2Cc3cc(F)c(OCc4ccccc4)cc3C2=O)CC1]

Trans-4-((6-(benzyloxy)-5-fluoro-1-oxoisoindolin-2-yl)methyl)cyclohexanecarbaldehyde (9-10)

Compound 9-10 was prepared from 9-9 by a procedure similar to that used in the synthesis of 3-5.

Example 67

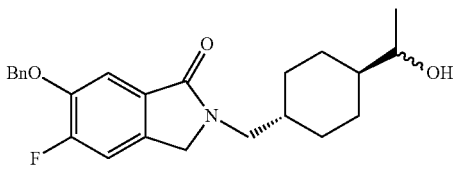 [SMILES: CC(O)[C@H]1CC[C@H](CN2Cc3cc(F)c(OCc4ccccc4)cc3C2=O)CC1]

6-(Benzyloxy)-5-fluoro-2-((trans-4-(1-hydroxyethyl)cyclohexyl)methyl)isoindolin-1-one (9-11)

A solution of 9-10 (80 mg, 0.21 mmol) in anhydrous THF (2 mL) was added dropwise to a stirred solution of methylmagnesium bromide (3 M, 0.21 mL, 0.63 mmol) in dry THF (3 mL) under argon. After the mixture was stirred for 40 min at rt, the reaction mixture was quenched with 1 N HCl (10 mL) and extracted with EtOAc (4×15 mL). The organic phases were combined, dried over sodium sulfate, filtered, concentrated and purified by flash chromatography on silica gel (hexane/EtOAc=1/2) to yield 9-11 (70 mg, 84% yield). HPLC >99% pure.

Example 68

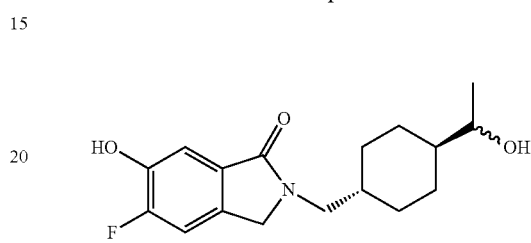

5-Fluoro-6-hydroxy-2-((trans-4-(1-hydroxyethyl)cyclohexyl)methyl)isoindolin-1-one (9-12)

Compound 9-12 was prepared from 9-11 by a procedure similar to that used in the synthesis of 3-4. HPLC >99% pure; MS m/e 306 (M–H).

Example 69

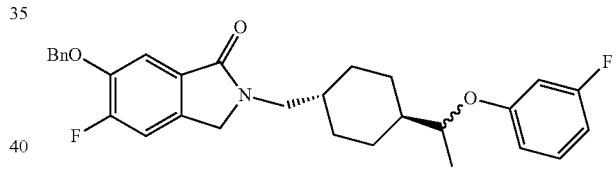

2-((Trans-4-(1-(3-fluorophenoxy)ethyl)cyclohexyl)methyl)-6-(benzyloxy)-5-fluoroisoindolin-1-one (9-13)

9-13 was prepared from 9-11 by a procedure analogous to that used in the synthesis of 5-5 except that 3-fluorophenol was used in place of resorcinol.

Example 70

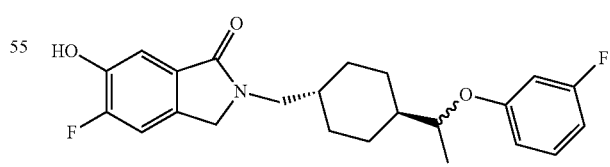

2-((Trans-4-(1-(3-fluorophenoxy)ethyl)cyclohexyl)methyl)-5-fluoro-6-hydroxyisoindolin-1-one (9-14)

9-14 was prepared from 9-13 by a procedure analogous to that used in the synthesis of 3-4. HPLC 95% pure; MS m/e 400 (M–H).

REACTION SCHEME 10
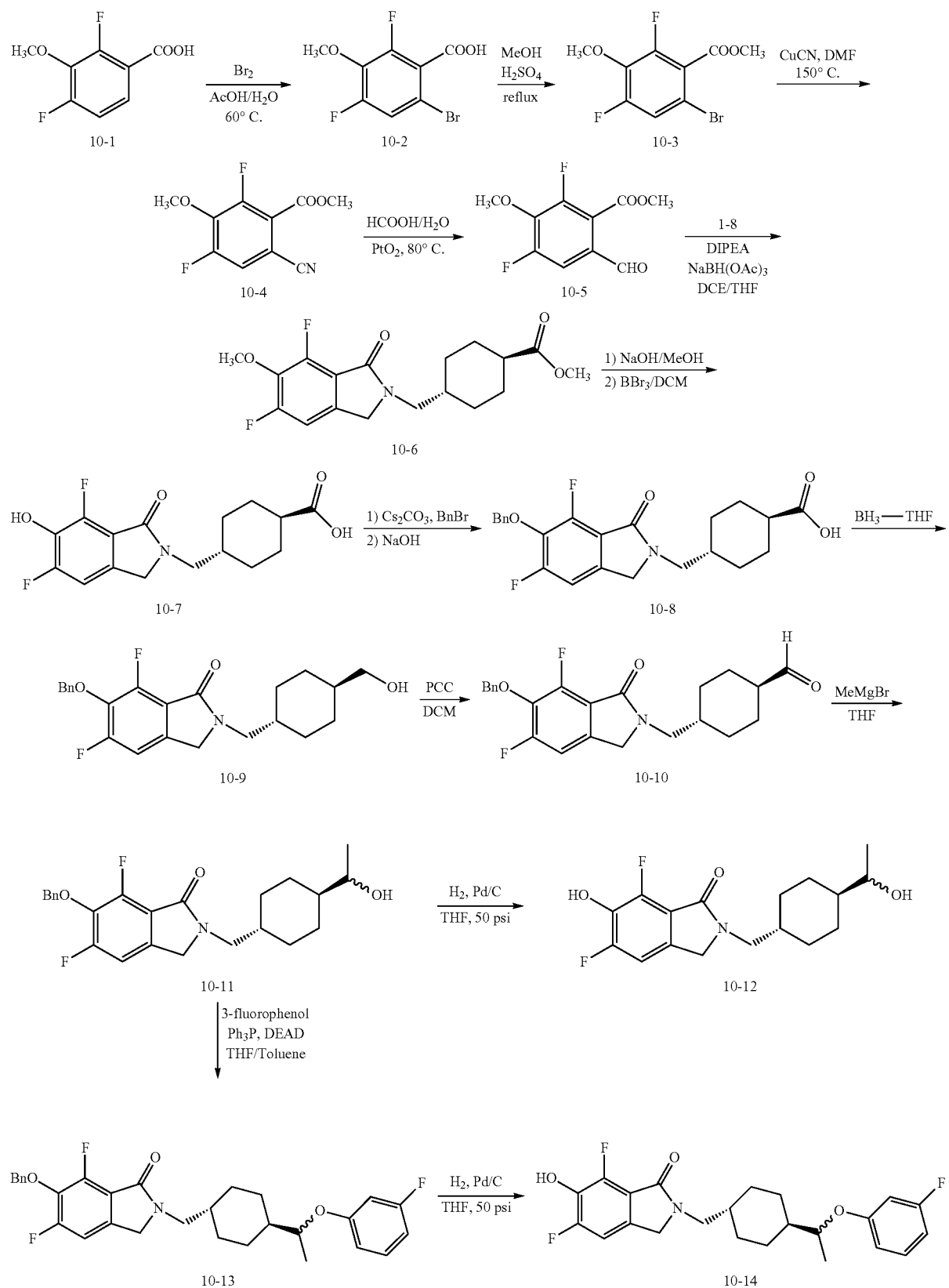

The reactions depicted in Scheme 10 (with 10-1 as starting material) were carried out using essentially the same procedures used to carry out the analogous reactions depicted in Scheme 9 (with 9-1 as starting material). 10-12 was obtained as HPLC >99% pure; MS m/e 324 (M−H). 10-14 was obtained as HPLC >99% pure; MS m/e 418 (M−H).

REACTION SCHEME 11

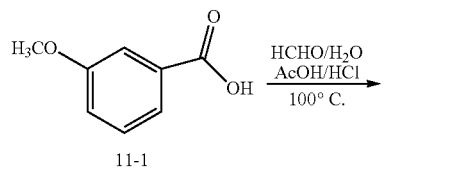

11-1

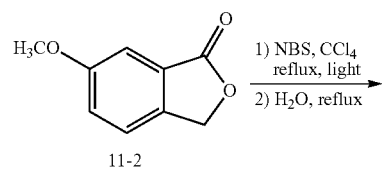

11-2

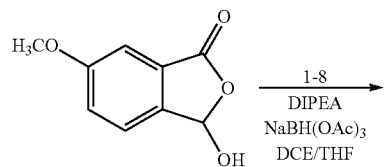

11-3

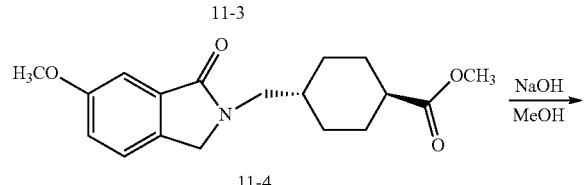

11-4

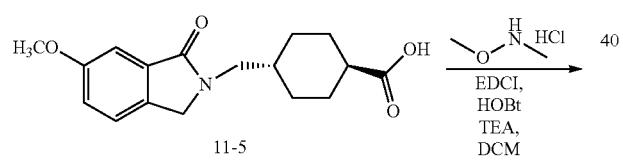

11-5

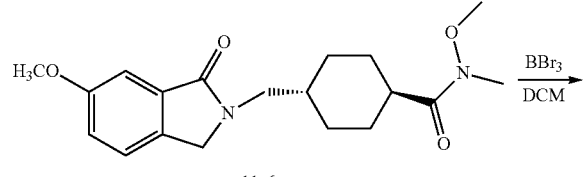

11-6

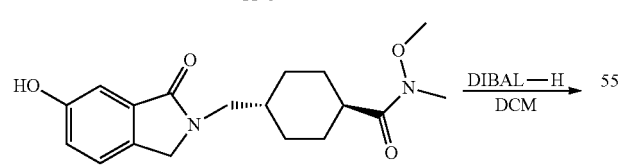

11-7

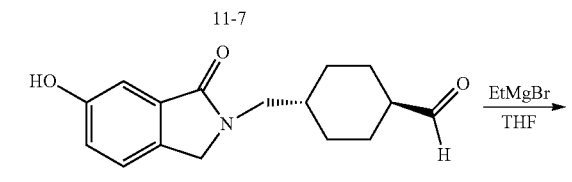

11-8

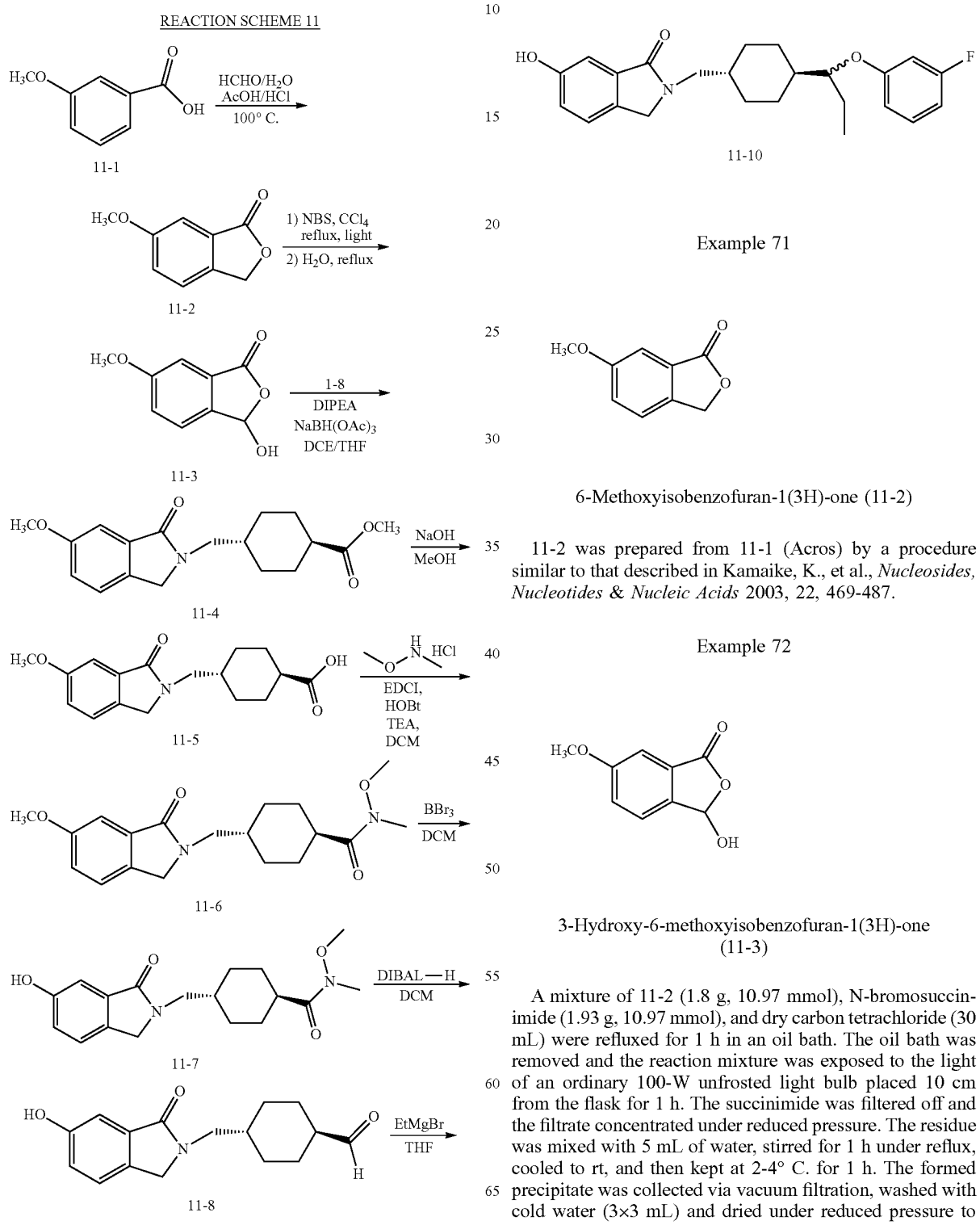

11-9

11-10

Example 71

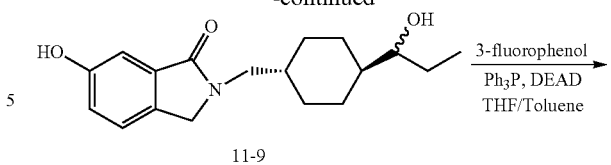

6-Methoxyisobenzofuran-1(3H)-one (11-2)

11-2 was prepared from 11-1 (Acros) by a procedure similar to that described in Kamaike, K., et al., *Nucleosides, Nucleotides & Nucleic Acids* 2003, 22, 469-487.

Example 72

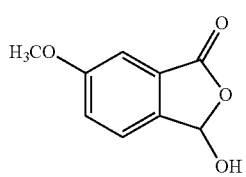 [SMILES: COc1ccc2c(c1)C(=O)OC2O]

3-Hydroxy-6-methoxyisobenzofuran-1(3H)-one (11-3)

A mixture of 11-2 (1.8 g, 10.97 mmol), N-bromosuccinimide (1.93 g, 10.97 mmol), and dry carbon tetrachloride (30 mL) were refluxed for 1 h in an oil bath. The oil bath was removed and the reaction mixture was exposed to the light of an ordinary 100-W unfrosted light bulb placed 10 cm from the flask for 1 h. The succinimide was filtered off and the filtrate concentrated under reduced pressure. The residue was mixed with 5 mL of water, stirred for 1 h under reflux, cooled to rt, and then kept at 2-4° C. for 1 h. The formed precipitate was collected via vacuum filtration, washed with cold water (3×3 mL) and dried under reduced pressure to yield 11-3 (1.99 g, 100% yield). HPLC 95% pure.

Example 73

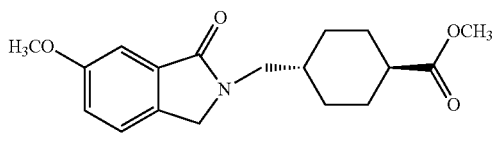 [SMILES: COc1ccc2c(c1)C(=O)N(C[C@H]1CC[C@H](C(=O)OC)CC1)C2]

Trans-methyl 4-((6-methoxy-1-oxoisoindolin-2-yl)methyl)cyclohexanecarboxylate (11-4)

To a solution of 11-3 (0.88 g, 4.9 mmol) in DCE/THF (40 mL/6 mL) were added 1-8 (1 g, 4.83 mmol) and DIPEA (415 µL, 2.4 mmol). The mixture stirred for 10 min before NaBH(OAc)$_3$ (97%) (2 g, 8.8 mmol) was added. The mixture was stirred at rt for five days and washed with 1 N HCl (2×15 mL). The organic phase was concentrated and purified by flash chromatography on silica gel (hexane/EtOAc=1/1 to 1/2) to yield 11-4 (1.4 g, 90% yield).

Example 74

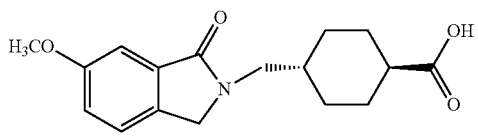 [SMILES: COc1ccc2c(c1)C(=O)N(C[C@H]1CC[C@H](C(=O)O)CC1)C2]

Trans-4-((6-methoxy-1-oxoisoindolin-2-yl)methyl)cyclohexanecarboxylic acid (11-5)

11-5 was prepared from 11-4 by a procedure analogous to that used in the synthesis of 1-10.

Example 75

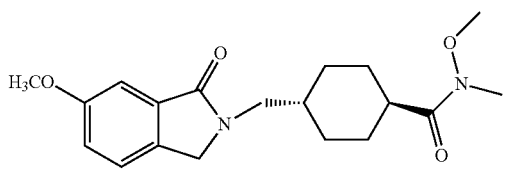

Trans-N-methoxy-4-((6-methoxy-1-oxoisoindolin-2-yl)methyl)-N-methylcyclohexanecarboxamide (11-6)

11-5 (230 mg, 0.76 mmol), N,O-dimethylhydroxylamine hydrochloride (221 mg, 2.21 mmol), and HOBt (57 mg, 0.42 mmol) were mixed in dry DCM (25 mL). EDCI (255 mg, 1.33 mmol) and TEA (0.37 mL, 2.58 mmol) were added portion wise and the resulting reaction mixture was stirred at rt for 6.5 h. The mixture was washed with 1 N HCl (3×15 mL), 1 N NaOH (15 mL), water (20 mL), dried over sodium sulfate, filtered, concentrated to yield crude 11-6 as an solid (250 mg, 95% yield), which was used in the next step without further purification.

Example 76

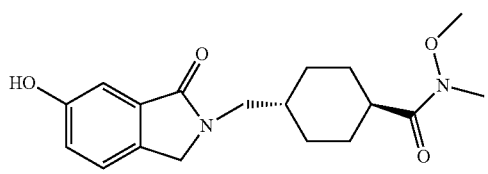 [SMILES: CON(C)C(=O)[C@H]1CC[C@H](CN2Cc3ccc(O)cc3C2=O)CC1]

Trans-4-((6-hydroxy-1-oxoisoindolin-2-yl)methyl)-N-methoxy-N-methylcyclohexanecarboxamide (11-7)

11-7 was prepared from 11-6 by a procedure analogous to that used in the synthesis of 1-12.

Example 77

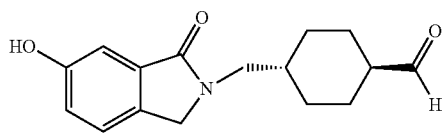 [SMILES: O=C[C@H]1CC[C@H](CN2Cc3ccc(O)cc3C2=O)CC1]

Trans-4-((6-hydroxy-1-oxoisoindolin-2-yl)methyl)cyclohexanecarbaldehyde (11-8)

To a solution of 11-7 (80 mg, 0.24 mmol) in DCM (12 mL) cooled in a dry ice-acetone bath was added DIBAL-H (1.1 M solution, 0.28 mL, 0.31 mmol) dropwise under an argon atmosphere. After the mixture was stirred for 50 min at the same temperature (−78° C.), additional DIBAL-H (1.1 M, 0.28 mL, 0.31 mmol) was added. After 5 h, the dry ice bath was removed and 1 N HCl (15 mL) was added to the reaction mixture. The quenched reaction mixture was stirred for 15 min at rt and the aqueous phase was separated, extracted with EtOAc (3×10 mL). The organic phases were combined, dried over Na$_2$SO$_4$, filtered and concentrated to yield crude 11-8 (50 mg, 76% yield), which was used in the next step without further purification.

Example 78

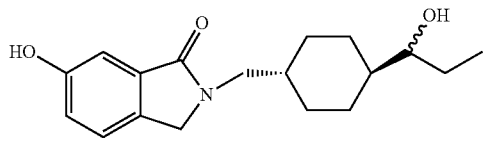 [SMILES: CCC(O)[C@H]1CC[C@H](CN2Cc3ccc(O)cc3C2=O)CC1]

6-Hydroxy-2-((trans-4-(1-hydroxypropyl)cyclohexyl)methyl)isoindolin-1-one (11-9)

11-9 was prepared from 11-8 by a procedure analogous to that used in the synthesis of 9-11 except that ethylmagnesium bromide was used in place of methylmagnesium bromide.

Example 79

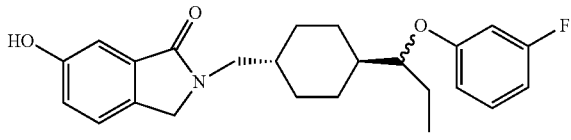 [SMILES: CCC(Oc1cccc(F)c1)[C@H]1CC[C@H](CN2Cc3ccc(O)cc3C2=O)CC1]

2-((Trans-4-(1-(3-fluorophenoxy)propyl)cyclohexyl)methyl)-6-hydroxyisoindolin-1-one (11-10)

11-10 was prepared from 11-9 by a procedure analogous to that used in the synthesis of 5-5 except that 3-fluorophenol was used in place of resorcinol. HPLC 92% pure; MS m/e 396 (M–H).

REACTION SCHEME 12

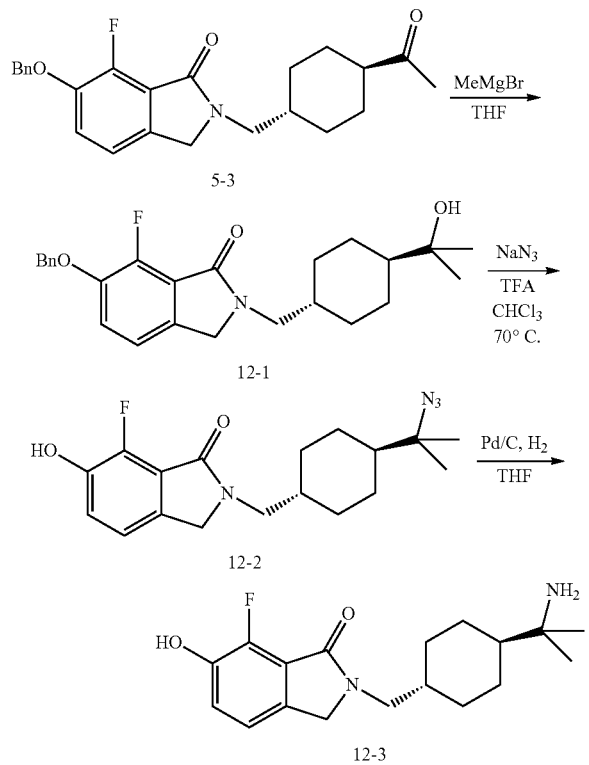

Example 80

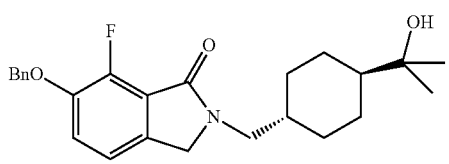 [SMILES: CC(C)(O)[C@H]1CC[C@H](CN2Cc3ccc(OCc4ccccc4)c(F)c3C2=O)CC1]

6-(Benzyloxy)-7-fluoro-2-(((1r,4r)-4-(2-hydroxypropan-2-yl)cyclohexyl)methyl)isoindolin-1-one (12-1)

12-1 was prepared from 5-3 by a procedure analogous to that used in the synthesis of 2-5 from 1-13.

Example 81

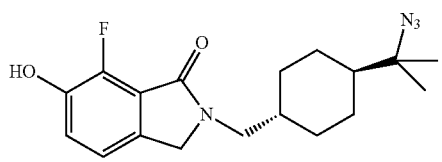 [SMILES: CC(C)(N=[N+]=[N-])[C@H]1CC[C@H](CN2Cc3ccc(O)c(F)c3C2=O)CC1]

2-(((1r,4r)-4-(2-Azidopropan-2-yl)cyclohexyl)methyl)-7-fluoro-6-hydroxyisoindolin-1-one (12-2)

To a solution of 12-1 (10 mg, 0.024 mmol) in chloroform (0.2 mL) were added sodium azide (65 mg, 1 mmol) and TFA (110 uL, 1.43 mmol) under an argon atmosphere. The mixture was stirred at 70° C. for 2 h and cooled down to rt. The cooled mixture was diluted with water (3 mL) and extracted with ethyl acetate (3×3 mL). The combined extracts were dried over sodium sulfate, filtered and concentrated to yield 12-2, which was used in the next step without further purification.

Example 82

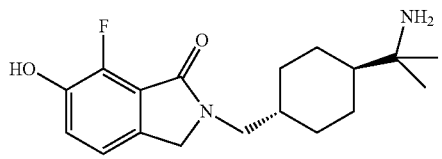 [SMILES: CC(C)(N)[C@H]1CC[C@H](CN2Cc3ccc(O)c(F)c3C2=O)CC1]

2-(((1r,4r)-4-(2-Aminopropan-2-yl)cyclohexyl)methyl)-7-fluoro-6-hydroxyisoindolin-1-one (12-3)

12-2 (<10 mg, <0.024 mmol), 10% Pd/C (20 mg), and THF (25 mL) in a 500 mL-Parr bottle was shaken under 50 psi of hydrogen overnight. After the reaction mixture was filtered and concentrated, a fraction of the resultant crude 12-3 was subjected to reverse phase C-18 silica gel chromatography using a gradient of 0-100% MeCN in 0.07% aqueous TFA as eluent. Evaporation of the eluent from the collected fractions containing 12-3 afforded pure 12-3 (1-2 mg). HPLC >95% pure; MS m/e 319.18 (M–H).

REACTION SCHEME 13

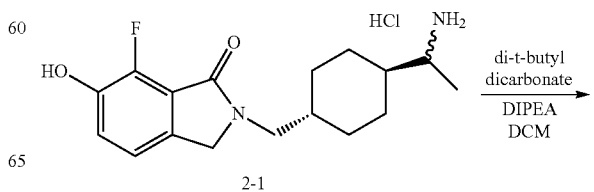

-continued

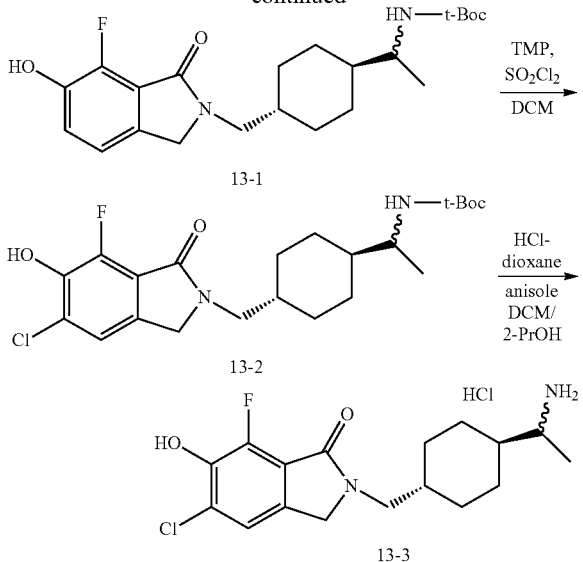

13-1

13-2

13-3

Example 83

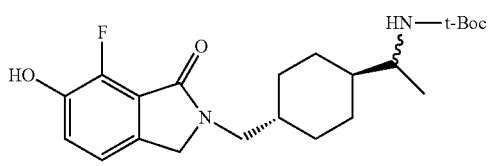

tert-Butyl 1-((1r,4r)-4-((7-fluoro-6-hydroxy-1-oxoisoindolin-2-yl)methyl)cyclohexyl)ethylcarbamate (13-1)

2-1 HCl salt (130 mg, 0.38 mmol) and DIPEA (368 uL, 2.12 mmol) were stirred in DCM (12 mL) for 15 min to dissolve the solids. Di-tert-butyl dicarbonate (243 mg, 1.11 mmol) was added and the mixture stirred at rt for 1.5 h. The mixture was washed with 0.01 N HCl (20 mL) and the separated aqueous phase was extracted with DCM (2×10 mL). The organic phases were combined, dried ($Na_2SO_4$), filtered, and concentrated to yield 13-1 (150 mg, 97% pure on HPLC).

Example 84

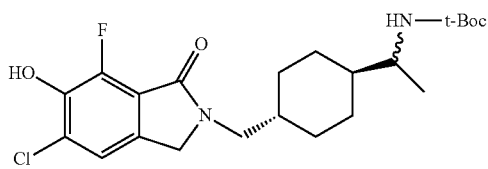

tert-Butyl 1-((1r,4r)-4-((5-chloro-7-fluoro-6-hydroxy-1-oxoisoindolin-2-yl)methyl)cyclohexyl)ethylcarbamate (13-2)

To a stirred solution of 13-1 (150 mg, 0.37 mmol) in DCM (30 mL) were added 2,2,6,6-tetramethylpiperidine (TMP, 61.6 uL, 0.37 mmol) and sulfuryl chloride (300 uL, 3.7 mmol) dropwise at rt under argon. After the reaction mixture was stirred at rt for 1 h, the mixture was concentrated and the residue subjected to flash chromatography on silica gel (hexane/EtOAc 1/1 with 0-10% of MeOH) to yield 13-2 (80 mg, 97% pure on HPLC).

Example 85

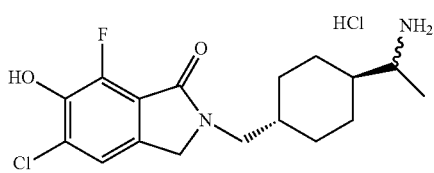 [SMILES: Cl ; CC(N)[C@H]1CC[C@H](CN2Cc3cc(Cl)c(O)c(F)c3C2=O)CC1]

2-(((1r,4r)-4-(1-Aminoethyl)cyclohexyl)methyl)-5-chloro-7-fluoro-6-hydroxyisoindolin-1-one hydrochloride (13-3)

To a stirred solution of 13-2 (80 mg, 0.18 mmol) and anisole (19 uL, 0.18 mmol) in DCM/2-PrOH (9 mL/3 mL) was added HCl in 1,4-dioxane (4 M, 9.1 mL, 36.4 mmol). After 1 h, the reaction mixture was concentrated on rotary evaporator. The resulting residue was mixed with ether (10 mL) and concentrated again. The resultant solid residue was triturated in ether (10 mL), collected via vacuum filtration, and washed with ether (3×5 mL) to yield 13-3 as an off-white solid (50 mg). HPLC >96% pure; MS m/e 341.1 (M+H of 13-3 free base).

Biochemical Assay

MIF Tautomerase Inhibitory Assay with L-Dopachrome Methyl Ester

Assay Method (pH 7.34, 0.017-0.033% DMSO, 0.034% EtOH): A fresh stock solution of L-dopachrome methyl ester in MeOH was prepared at 55-65 mM through oxidation of L-3,4-dihydroxyphenylalanine methyl ester hydrochloride with sodium periodate according to the procedure described in WO9729635A1. MeOH was removed from 0.5 mL of the L-dopachrome methyl ester/MeOH solution (55-65 mM) under a stream of argon and the residue taken up in appropriate amount of water to prepare a substrate solution (7-10 mM). Active Human MIF (from ProSpec) (10 fig) was dissolved in 675 μL 0.1% bovine serum albumin (BSA) in water, and the resultant MIF solution (1 volume) mixed with 55 volumes of $Na_2HPO_4$ buffer (50 mM, pH 7.34) to form a 265 ng/mL MIF working solution. MIF working solution (280 μL) or a no-MIF working solution (prepared by mixing 0.1% BSA (1 volume) with the aforementioned $Na_2HPO_4$ buffer (55 volumes)) was transferred to wells in a column of 8 wells on a 96-well plate in a Plate Reader (SPECTRAmax Plus 384, Molecular Devices), and 5 μL of $H_2O$/DMSO (99/1) containing no inhibitor or an inhibitor (whose concentration was verified by HPLC). Without pre-mixing or pre-incubation, 10 μL freshly prepared L-dopachrome methyl ester/$H_2O$ solution (7-10 mM) was added to each well with a multi-pipet. The assay samples were mixed immediately by sucking up and expelling the contents of the wells three times with a multi-pipet. The absorbance ($A_1$) at 475 nm was then recorded for each sample every 2 s for 3 min. After 5-6 min, the samples were monitored again for 3 min with a reading every two seconds at 475 nm ($A_2$). It can be shown that when [substrate]<<$K_m$, plots of $Ln(A_1-A_2)$ versus time are linear with slopes m (Eq 1). IC$_{50}$ values were estimated from Eq 2-5, the inhibitor concentration [I] in the assay mixture and values of m in the presence (m$_i$), absence (m$_o$) of the inhibitor, the value of m observed for the non-MIF blank (m$_n$), the MIF concentration (e), and the specificity constant for the MIF catalyzed reaction (k$_{cat}$/K$_m$).

$$Ln(A_1-A_2)=-mt \quad (Eq\ 1)$$

$$F=(m_i-m_n)/(m_o-m_n) \quad (Eq\ 2)$$

$$\text{Wherein } m_o-m_n=ek_{cat}/K_m \quad (Eq\ 3)$$

$$\text{and } m_i-m_n=(ek_{cat}/K_m)[I]/([I]+IC_{50}) \quad (Eq\ 4)$$

$$IC_{50}=[I]F/(1-F) \quad (Eq\ 5)$$

The compounds listed in Table 1, provided herein, were prepared via procedures identical or similar to those described in the Examples 1-85. The listed compounds were >95% pure by HPLC. Each listed compound yielded a mass spectrum consistent with its structure. Concentrations of MIF tautomerase inhibitors used in the assay were verified by HPLC and the extinction coefficients of the inhibitors. The designated relative potency of MIF tautomerase inhibitors is based on the IC$_{50}$ as determined by the method described in Biochemical Assay as follows: A, IC$_{50}$<1 µM; B, 1 µM≤IC$_{50}$<5 µM; C, 5 µM≤IC$_{50}$<10 µM; D, 10 µM≤IC$_{50}$<50 µM; E, 50 µM≤IC$_{50}$<200 µM.

OTHER EMBODIMENTS

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of Formula (I):

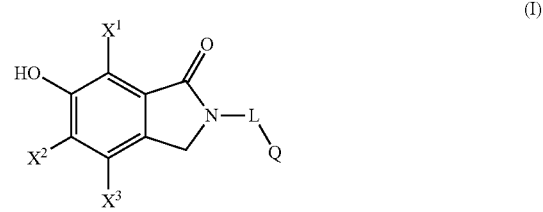

or a pharmaceutically acceptable salt or stereoisomer thereof, wherein:

X$^1$ is hydrogen, halogen, optionally substituted C$_{1-6}$ alkyl, —CO$_2$H, —CO$_2$R$^{X1}$, or —C(=O)NHR$^{X1}$, wherein R$^{X1}$ is optionally substituted C$_{1-6}$ alkyl, optionally substituted C$_{3-6}$ carbocyclyl, an oxygen protecting group when attached to oxygen, or a nitrogen protecting group when attached to nitrogen;

X$^2$ is hydrogen, halogen, optionally substituted C$_{1-6}$ alkyl, —CO$_2$H, —CO$_2$R$^{X2}$, or —C(=O)NHR$^{X2}$, wherein R$^{X2}$ is optionally substituted C$_{1-6}$ alkyl, optionally substituted C$_{3-6}$ carbocyclyl, an oxygen protecting group when attached to oxygen, or a nitrogen protecting group when attached to nitrogen;

X$^3$ is hydrogen, halogen, optionally substituted C$_{1-6}$ alkyl, —OH, —OR$^{X3}$, —CO$_2$H, —CO$_2$R$^{X3}$, or —C(=O)NHR$^{X3}$, wherein R$^{X3}$ is optionally substituted C$_{1-6}$ alkyl, optionally substituted C$_{3-6}$ carbocyclyl, an oxygen protecting group when attached to oxygen, or a nitrogen protecting group when attached to nitrogen;

L is a linking group selected from the group consisting of:
optionally substituted $C_{3-14}$ carbocyclylene,
-$L^1$-$L^2$-, wherein $L^1$ is optionally substituted $C_{1-6}$ alkylene and attached to the N atom, and $L^2$ is optionally substituted $C_{3-14}$ carbocyclylene and attached to Q, and
-$L^3$-$L^4$-, wherein $L^3$ is attached to the N atom and is methylene (—$CH_2$—), ethylene (—$CH_2CH_2$—), or optionally substituted $C_{3-6}$ alkylene, and $L^4$ is optionally substituted $C_{6-14}$ arylene and attached to Q;

Q is:
hydrogen,
—OH,
$C_{3-12}$ cycloalkyl optionally substituted with substituted or unsubstituted $C_{1-6}$ alkyl,
$C_{1-6}$ alkyl optionally substituted with substituted or unsubstituted $C_{3-12}$ cycloalkyl,
aryl optionally substituted with one to three groups independently selected from the group consisting of halogen, carboxyl, hydroxyl, —$OR^Q$, —$CO_2R^Q$, and —C(=O)$NHR^Q$, wherein $R^Q$ is optionally substituted $C_{1-6}$ alkyl, optionally substituted $C_{2-6}$ alkenyl, optionally substituted $C_{2-6}$ alkynyl, optionally substituted $C_{3-6}$ carbocyclyl, an oxygen protecting group when attached to oxygen, or a nitrogen protecting group when attached to nitrogen,
or Q is selected from the group consisting of:

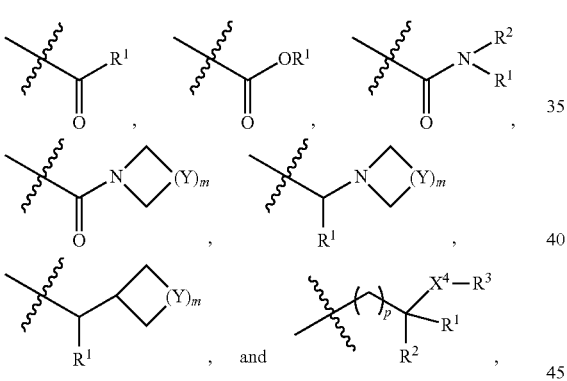

wherein $R^1$ and $R^2$ are each independently hydrogen, $C_{3-12}$ cycloalkyl optionally substituted with substituted or unsubstituted $C_{1-6}$ alkyl, or $C_{1-6}$ alkyl optionally substituted with substituted or unsubstituted $C_{3-12}$ cycloalkyl;
each instance of Y is independently, as valency and stability permits, —O—, —S—, —N($R^Y$)—, or —C($R^Y$)$_2$—, wherein m is 2, 3, or 4, and $R^Y$ is hydrogen or $C_{1-6}$ alkyl;
p is 0, 1, 2, 3, or 4;
$X^4$ is —O— or —($R^X$)N—,
wherein $R^X$ is selected from the group consisting of:
hydrogen,
$C_{3-12}$ cycloalkyl optionally substituted with substituted or unsubstituted $C_{1-6}$ alkyl,
$C_{1-6}$ alkyl optionally substituted with substituted or unsubstituted $C_{3-12}$ cycloalkyl,
—C(=O)$R^{X5}$, wherein $R^{X5}$ is optionally substituted $C_{1-6}$ alkyl,
-$L^{X1}$—$CO_2R^{X6}$, wherein $L^{X1}$ is $C_{1-9}$ alkylene optionally substituted with substituted or unsubstituted alkyl or substituted or unsubstituted aryl, and $R^{X6}$ is hydrogen or optionally substituted $C_{1-6}$ alkyl, and
-$L^{X2}$-O—$R^{X7}$, wherein $L^{X2}$ is optionally substituted $C_{1-6}$ alkylene, and $R^{X7}$ is optionally substituted $C_{1-6}$ alkyl;

$R^3$ is:
hydrogen,
$C_{3-12}$ cycloalkyl optionally substituted with substituted or unsubstituted $C_{1-6}$ alkyl,
$C_{1-6}$ alkyl optionally substituted with substituted or unsubstituted $C_{3-12}$ cycloalkyl,
—C(=O)$R^{3A}$ wherein $R^{3A}$ is optionally substituted $C_{1-6}$ alkyl or optionally substituted aryl,
$C_{1-6}$ alkyl optionally substituted with a substituted or unsubstituted 5- or 6-membered heterocycle wherein the heterocyclic ring contains from one to four hetero atoms selected from the group consisting of N, S or O,
$C_{1-6}$ alkyl optionally substituted with a substituted or unsubstituted heteroaryl,
aryl optionally substituted with one to three groups selected from the group consisting of halogen, —$CO_2H$, —OH, —$OR^{3B}$, —C(=O)$OR^{3B}$, and —C(=O)$NHR^{3B}$, wherein $R^{3B}$ is optionally substituted $C_{1-6}$ alkyl,
or $R^3$ and $R^X$ are joined to form an optionally substituted 5-membered heteroaryl ring,
or $R^3$ is a group of formula:

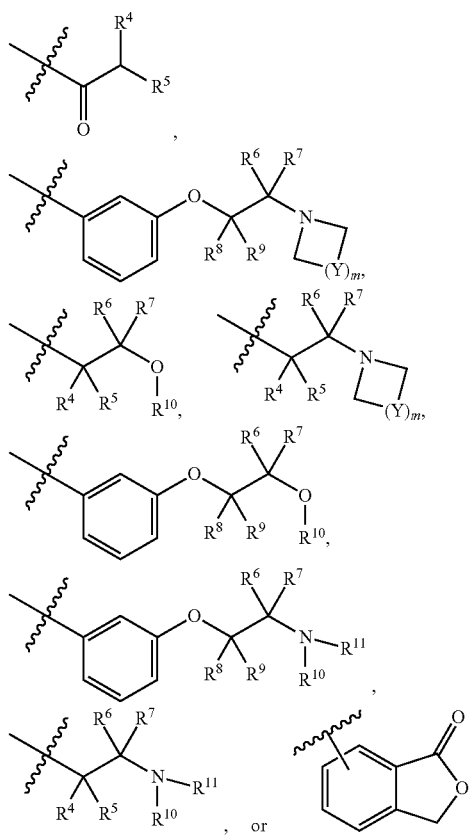

wherein each instance of Y is independently, as valency and stability permits, —O—, —S—, —N($R^Y$)—, or —C($R^Y$)$_2$—, wherein m is 2, 3, or 4, and $R^Y$ is hydrogen or $C_{1-6}$ alkyl;

R⁴ and R⁵ are each independently selected from the group consisting of:
hydrogen,
—CO₂H,
—C(=O)NHR⁴ᴬ, wherein R⁴ᴬ is optionally substituted $C_{1-6}$ alkyl,
—OH,
—OR⁴ᴬ, wherein R⁴ᴬ is optionally substituted $C_{1-6}$ alkyl,
-L⁴-CO₂R⁴ᴬ, wherein L⁴ is $C_{1-9}$ alkylene optionally substituted with substituted or unsubstituted alkyl or substituted or unsubstituted aryl, and R⁴ᴬ is hydrogen or optionally substituted $C_{1-6}$ alkyl,
$C_{3-12}$ cycloalkyl optionally substituted with substituted or unsubstituted $C_{1-6}$ alkyl,
$C_{1-6}$ alkyl optionally substituted with substituted or unsubstituted $C_{3-12}$ cycloalkyl,
5- or 6-membered optionally substituted heterocyclic ring containing one to four atoms of N, S or O, and
aryl unsubstituted or substituted with 1, 2, or 3 groups selected from the group consisting of halogen, —CO₂H, —OH, —OR⁴ᴬ, —C(=O)OR⁴ᴬ, and —C(=O)NHR⁴ᴬ, wherein R⁴ᴬ is optionally substituted $C_{1-6}$ alkyl;
R⁶, R⁷, R⁸, and R⁹ are each independently selected from the group consisting of:
hydrogen,
$C_{3-12}$ cycloalkyl optionally substituted with substituted or unsubstituted $C_{1-6}$ alkyl,
$C_{1-6}$ alkyl optionally substituted with substituted or unsubstituted $C_{3-12}$ cycloalkyl,
-L⁶-CO₂R⁶ᴬ, wherein L⁶ is absent or $C_{1-9}$ alkylene optionally substituted with substituted or unsubstituted alkyl or substituted or unsubstituted aryl, and R⁶ᴬ is hydrogen or optionally substituted $C_{1-6}$ alkyl,
-L⁶-C(=O)NHR⁶ᴬ, wherein L⁶ is absent or $C_{1-9}$ alkylene optionally substituted with substituted or unsubstituted alkyl or substituted or unsubstituted aryl, and R⁶ᴬ is hydrogen or optionally substituted $C_{1-6}$ alkyl,
5- or 6-membered optionally substituted heterocyclic ring containing one to four atoms of N, S or O, and
aryl unsubstituted or substituted with 1, 2, or 3 groups selected from the group consisting of halogen, —CO₂H, —OH, —OR⁶ᴬ, —C(=O)OR⁶ᴬ, and —C(=O)NHR⁶ᴬ, wherein R⁶ᴬ is optionally substituted $C_{1-6}$ alkyl;
and
R¹⁰ and R¹¹ are each independently selected from the group consisting of:
hydrogen,
$C_{3-12}$ cycloalkyl optionally substituted with substituted or unsubstituted $C_{1-6}$ alkyl,
$C_{1-6}$ alkyl optionally substituted with substituted or unsubstituted $C_{3-12}$ cycloalkyl,
—C(=O)R¹⁰ᴬ, wherein R¹⁰ᴬ is optionally substituted $C_{1-6}$ alkyl,
-L¹⁰-CO₂R¹⁰ᴮ, wherein L¹⁰ is $C_{1-9}$ alkylene optionally substituted with substituted or unsubstituted alkyl or substituted or unsubstituted aryl, and R¹⁰ᴮ is hydrogen or optionally substituted $C_{1-6}$ alkyl, and
-L¹¹-O—R¹⁰ᴬ, wherein L¹¹ is optionally substituted $C_{1-6}$ alkylene, and R¹⁰ᴬ is optionally substituted $C_{1-6}$ alkyl.

2. The compound of claim 1, or a pharmaceutically acceptable salt or stereoisomer thereof, wherein L is:

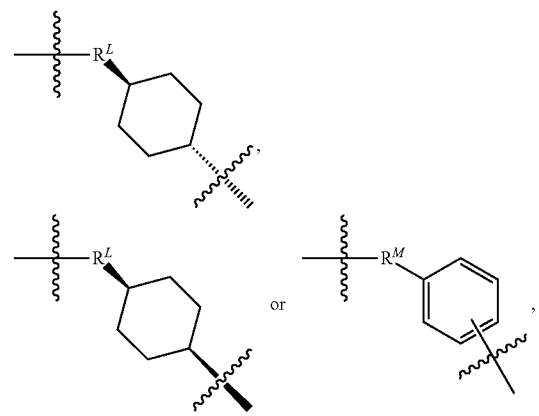

wherein $R^L$ is absent or optionally substituted $C_{1-4}$ alkylene; $R^M$ is methylene (—CH₂—), ethylene (—CH₂CH₂—), or optionally substituted $C_{3-4}$ alkylene; the left sides of the L groups are attached to isoindolin-1-one unit, and the right sides of the L groups are attached to Q.

3. The compound of claim 1, or a pharmaceutically acceptable salt or stereoisomer thereof,
wherein:
X¹ and X² are each independently hydrogen, fluoro or chloro;
X³ is hydrogen;
L is

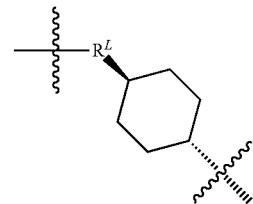

wherein $R^L$ is methylene; the left side of L is attached to isoindolin-1-one unit, and the right side of L is attached to Q;
Q is

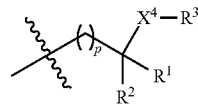

wherein p is 0;
X⁴ is —O—;
R¹ and R² are each independently hydrogen or $C_{1-6}$ alkyl optionally substituted with substituted or unsubstituted $C_{3-12}$ cycloalkyl;
R³ is

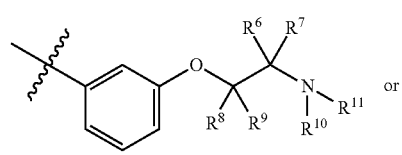

-continued

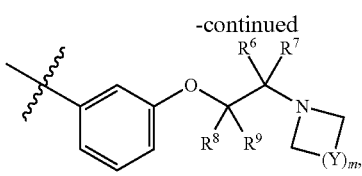

wherein
- $R^6$ is hydrogen, $-L^6-CO_2R^{6A}$, or $-L^6-C(=O)NHR^{6A}$, wherein $L^6$ is absent or $C_{1-9}$ alkylene optionally substituted with substituted or unsubstituted alkyl, or substituted or unsubstituted aryl, and $R^{6A}$ is hydrogen or optionally substituted $C_{1-6}$ alkyl;
- $R^7$, $R^8$ and $R^9$ are each independently hydrogen or $C_{1-6}$ alkyl optionally substituted with substituted or unsubstituted $C_{3-12}$ cycloalkyl;
- $R^{10}$ and $R^{11}$ are each independently hydrogen, $C_{1-6}$ alkyl, or $-C(=O)R^{10A}$, wherein $R^{10A}$ is optionally substituted $C_{1-6}$ alkyl; and
- Y is independently, as valency and stability permits, $-O-$, $-S-$, $-N(R^Y)-$, or $-C(R^Y)_2-$, wherein m is 2, 3, or 4, and R is hydrogen or $C_{1-6}$ alkyl.

4. The compound of claim 1, or a pharmaceutically acceptable salt or stereoisomer thereof,
wherein:
- $X^1$ and $X^2$ are each independently hydrogen, fluoro or chloro;
- $X^3$ is hydrogen;
- L is

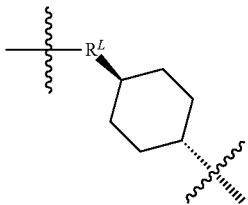

wherein $R^L$ is methylene; the left side of L is attached to isoindolin-1-one unit, and the right side of L is attached to Q;
Q is

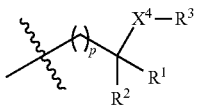

wherein p is 0;
$X^4$ is $-O-$;
$R^1$ and $R^2$ are each independently hydrogen or $C_{1-6}$ alkyl optionally substituted with substituted or unsubstituted $C_{3-12}$ cycloalkyl;
$R^3$ is
- hydrogen,
- $C_{3-12}$ cycloalkyl optionally substituted with substituted or unsubstituted $C_{1-6}$ alkyl,
- $C_{1-6}$ alkyl optionally substituted with substituted or unsubstituted $C_{3-12}$ cycloalkyl, $-C(=O)R^{3A}$ wherein $R^{3A}$ is optionally substituted $C_{1-6}$ alkyl or optionally substituted aryl, or

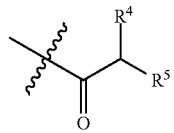

wherein $R^4$ and $R^5$ are each independently:
- hydrogen,
- $-OH$,
- $-OR^{4A}$ wherein $R^{4A}$ is optionally substituted $C_{1-6}$ alkyl,
- $C_{1-6}$ alkyl optionally substituted with substituted or unsubstituted $C_{3-12}$ cycloalkyl,
- $C_{3-12}$ cycloalkyl optionally substituted with substituted or unsubstituted $C_{1-6}$ alkyl, or
- $-L^4-CO_2R^{4A}$, wherein $L^4$ is $C_{1-6}$ alkylene optionally substituted with substituted or unsubstituted alkyl or substituted or unsubstituted aryl and $R^{4A}$ is hydrogen or optionally substituted $C_{1-6}$ alkyl.

5. The compound of claim 1, or a pharmaceutically acceptable salt or stereoisomer thereof,
wherein:
- $X^1$ and $X^2$ are each independently hydrogen, fluoro or chloro;
- $X^3$ is hydrogen;
- L is

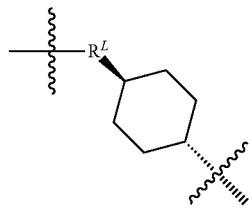

wherein $R^L$ is methylene; the left side of L is attached to isoindolin-1-one unit and the right side of L is attached to Q;
Q is

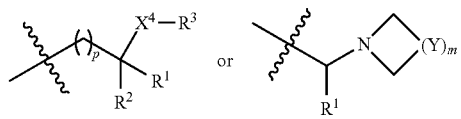

wherein p is 0;
$X^4$ is $-(R^X)N-$ wherein $R^X$ is:
- hydrogen,
- $C_{3-12}$ cycloalkyl optionally substituted with substituted or unsubstituted $C_{1-6}$ alkyl,
- $C_{1-6}$ alkyl optionally substituted with substituted or unsubstituted $C_{3-12}$ cycloalkyl, $-C(=O)R^{X5}$, wherein $R^{X5}$ is optionally substituted $C_{1-6}$ alkyl,
- $-L^{X1}-CO_2R^{X6}$, wherein $L^{X1}$ is $C_{1-9}$ alkylene optionally substituted with substituted or unsubstituted alkyl or substituted or unsubstituted aryl, and $R^{X6}$ is hydrogen or optionally substituted $C_{1-6}$ alkyl, and -L$^{X2}$-O—R$^{X7}$, wherein L$^{X2}$ is optionally substituted C$_{1-6}$ alkylene, and R$^{X7}$ is optionally substituted C$_{1-6}$ alkyl;
R$^1$ and R$^2$ are each independently hydrogen or C$_{1-6}$ alkyl optionally substituted with substituted or unsubstituted C$_{3-12}$ cycloalkyl;
Y is independently, as valency and stability permits, —O—, —S—, —N(R$^Y$)—, or —C(R$^Y$)$_2$—, wherein m is 2, 3, or 4, and R$^Y$ is hydrogen or C$_{1-6}$ alkyl; and
R$^3$ is:
hydrogen,
optionally substituted C$_{1-6}$ alkyl, or

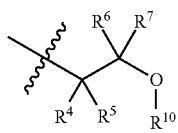

wherein R$^4$, R$^5$, R$^6$, R$^7$ and R$^{10}$ are each independently hydrogen or C$_{1-6}$ alkyl optionally substituted with substituted or unsubstituted cycloalkyl.

6. The compound of claim 1, or a pharmaceutically acceptable salt or stereoisomer thereof,
wherein:
X$^1$ and X$^2$ are each independently hydrogen, fluoro or chloro;
X$^3$ is hydrogen;
L is

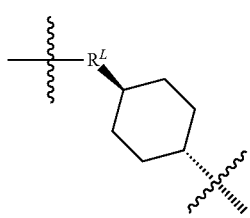

wherein R$^L$ is methylene; the left side of L is attached to isoindolin-1-one unit, and the right side of L is attached to Q;
Q is

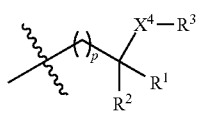

wherein p is 0;
X$^4$ is —O—;
R$^1$ and R$^2$ are each independently hydrogen or C$_{1-6}$ alkyl optionally substituted with substituted or unsubstituted C$_{3-12}$ cycloalkyl;
R$^3$ is

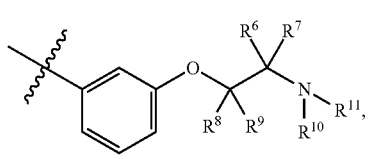

wherein R$^6$ is hydrogen or -L$^6$-CO$_2$R$^{6A}$, wherein L$^6$ is absent or C$_{1-9}$ alkylene optionally substituted with substituted or unsubstituted alkyl or substituted or unsubstituted aryl, and R$^{6A}$ is hydrogen;
R$^7$, R$^8$, and R$^9$ are each independently hydrogen or C$_{1-6}$ alkyl optionally substituted with substituted or unsubstituted C$_{3-12}$ cycloalkyl; and
R$^{10}$ and R$^{11}$ are each independently hydrogen, —C(=O)R$^{10A}$, wherein R$^{10A}$ is optionally substituted C$_{1-6}$ alkyl, or C$_{1-6}$ alkyl optionally substituted with substituted or unsubstituted C$_{3-12}$ cycloalkyl.

7. The compound of claim 1, or a pharmaceutically acceptable salt or stereoisomer thereof,
wherein:
X$^1$ and X$^2$ are each independently hydrogen, fluoro or chloro;
X$^3$ is hydrogen;
L is

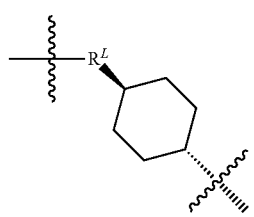

wherein R$^L$ is methylene; the left side of L is attached to isoindolin-1-one unit, and the right side of L is attached to Q;
Q is

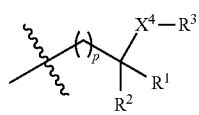

wherein p is 0;
X$^4$ is —O—;
R$^1$, R$^2$ and R$^3$ are each independently hydrogen or C$_{1-6}$ alkyl optionally substituted with substituted or unsubstituted C$_{3-12}$ cycloalkyl.

8. The compound of claim 1, or a pharmaceutically acceptable salt or stereoisomer thereof,
wherein:
X$^1$ and X$^2$ are each independently hydrogen, fluoro or chloro;
X$^3$ is hydrogen;
L is

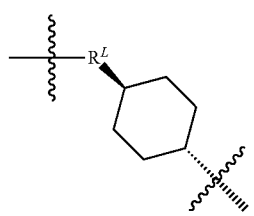

wherein R$^L$ is methylene; the left side of L is attached to isoindolin-1-one unit, and the right side of L is attached to Q;

Q is

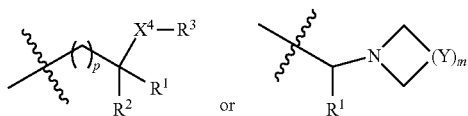

wherein p is 0;
X$^4$ is —(R$^X$)N— wherein R$^X$ is hydrogen or -L$^{X1}$-CO$_2$R$^{X6}$, wherein L$^{X1}$ is C$_{1-6}$ alkylene optionally substituted with substituted or unsubstituted alkyl or substituted or unsubstituted aryl, and R$^{X6}$ is hydrogen;
R$^1$ and R$^2$ are each independently hydrogen or C$_{1-6}$ alkyl optionally substituted with substituted or unsubstituted C$_{3-12}$ cycloalkyl;
Y is independently, as valency and stability permits, —O—, —S—, —N(R$^Y$)—, or —C(R$^Y$)$_2$—, wherein m is 2, 3, or 4, and R$^Y$ is hydrogen or C$_{1-6}$ alkyl; and
R$^3$ is hydrogen or C$_{1-6}$ alkyl optionally substituted with substituted or unsubstituted C$_{3-12}$ cycloalkyl.

9. The compound of claim 1, or a pharmaceutically acceptable salt or stereoisomer thereof, wherein:
X$^1$ and X$^2$ are each independently hydrogen, fluoro or chloro;
X$^3$ is hydrogen;
L is

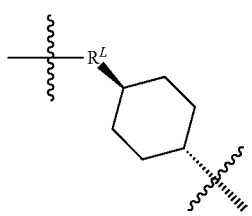

wherein R$^L$ is methylene; the left side of L is attached to isoindolin-1-one unit, and the right side of L is attached to Q;
Q is

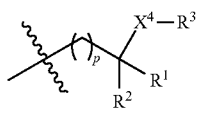

wherein p is 0;
X$^4$ is —(R$^X$)N— wherein R$^X$ is -L$^{X1}$-CO$_2$R$^{X6}$, wherein L$^{X1}$ is C$_{1-6}$ alkylene optionally substituted with substituted or unsubstituted alkyl or substituted or unsubstituted aryl, and R$^{X6}$ is hydrogen; and
R$^1$, R$^2$, and R$^3$ are each independently hydrogen or methyl.

10. The compound of claim 1, or a pharmaceutically acceptable salt or stereoisomer thereof, wherein:
X$^1$ and X$^2$ are each independently hydrogen or fluoro;
X$^3$ is hydrogen;

L is

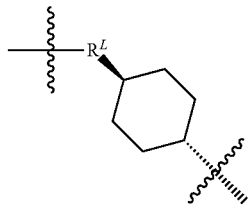

wherein R$^L$ is methylene; the left side of L is attached to isoindolin-1-one unit, and the right side of L is attached to Q;
Q is

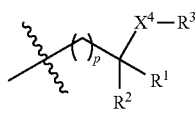

wherein p is 0;
X$^4$ is —(R$^X$)N— wherein R$^X$ is hydrogen or C$_{1-6}$ alkyl;
R$^3$ is hydrogen or C$_{1-6}$ alkyl; and
R$^1$ and R$^2$ are each independently hydrogen or methyl.

11. The compound of claim 1, or a pharmaceutically acceptable salt or stereoisomer thereof, wherein:
X$^1$ and X$^2$ are each independently hydrogen or chloro;
X$^3$ is hydrogen;
L is

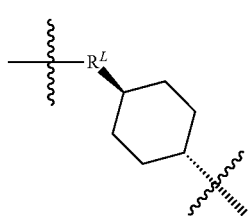

wherein R$^L$ is methylene; the left side of L is attached to isoindolin-1-one unit, and the right side of L is attached to Q;
Q is

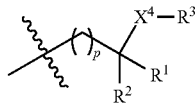

wherein p is 0;
X$^4$ is —(R$^X$)N— wherein R$^X$ is hydrogen or C$_1$ alkyl;
R$^3$ is hydrogen or C$_1$ alkyl; and
R$^1$ and R$^2$ are each independently hydrogen or methyl.

12. The compound of claim 1, or a pharmaceutically acceptable salt or stereoisomer thereof, wherein:
X$^1$ and X$^2$ are both hydrogen or fluoro;
X$^3$ is hydrogen;

L is

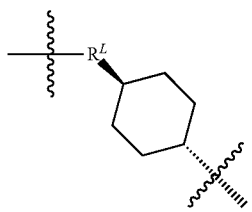

wherein $R^L$ is methylene; the left side of L is attached to isoindolin-1-one unit, and the right side of L is attached to Q:
Q is

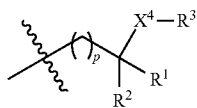

wherein p is 0;
$X^4$ is —$(R^X)$N— wherein $R^X$ is -$L^{X1}$-$CO_2R^{X6}$, wherein $L^{X1}$ is $C_{1-6}$ alkylene optionally substituted with substituted or unsubstituted alkyl or substituted or unsubstituted aryl, and $R^{X6}$ is hydrogen or optionally substituted $C_{1-6}$alkyl;
$R^3$ is hydrogen or $C_{1-6}$ alkyl; and
$R^1$ and $R^2$ are each independently hydrogen or methyl.

13. The compound of claim 1, or a pharmaceutically acceptable salt or stereoisomer thereof,
wherein:
$X^1$ and $X^2$ are both hydrogen or fluoro;
$X^3$ is hydrogen;
L is

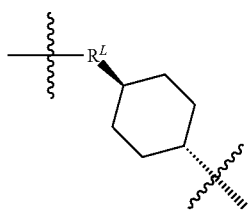

wherein $R^L$ is methylene; the left side of L is attached to isoindolin-1-one unit, and the right side of L is attached to Q;
Q is

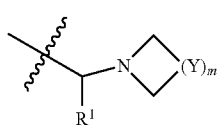

wherein p is 0;
$R^1$ is hydrogen or methyl; and
Y is independently, as valency and stability permits, —O—, —S—, —N($R^Y$)—, or —C($R^Y$)$_2$—, wherein m is 2, 3, or 4, and $R^Y$ is hydrogen or $C_{1-6}$ alkyl.

14. The compound of claim 1, or a pharmaceutically acceptable salt or stereoisomer thereof, wherein:
$X^1$ and $X^2$ are both hydrogen or fluoro;
$X^3$ is hydrogen;
L is

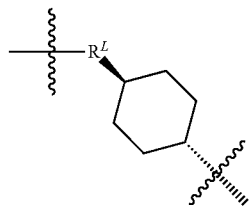

wherein $R^L$ is methylene; the left side of L is attached to isoindolin-1-one unit, and the right side of L is attached to Q;
Q is

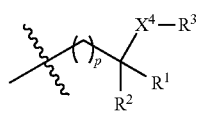

wherein p is 0;
$X^4$ is —$(R^X)$N— wherein $R^X$ is hydrogen or optionally substituted $C_{1-6}$ alkyl;
$R^3$ is hydrogen or optionally substituted $C_{1-6}$ alkyl; and
$R^1$ and $R^2$ are each independently hydrogen or methyl.

15. A compound selected from the group consisting of:

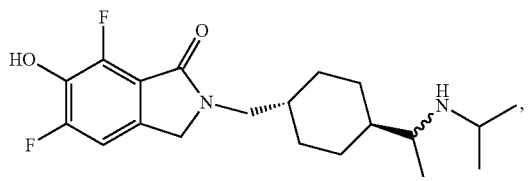

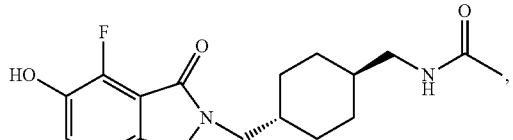

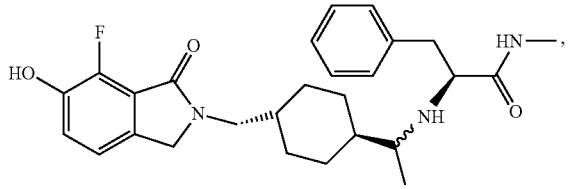

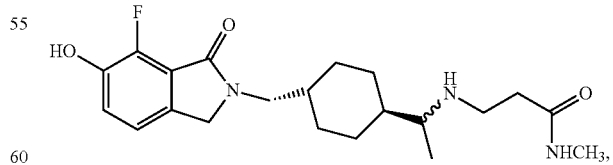

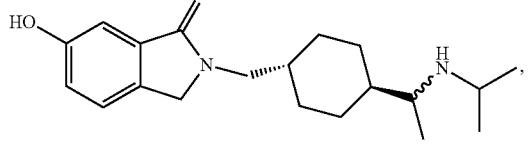

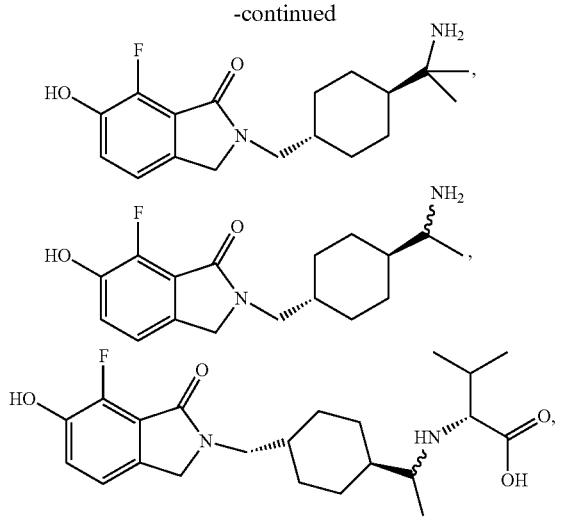
and pharmaceutically acceptable salts and stereoisomers thereof.
16. A pharmaceutical composition comprising a compound of claim 1, or a pharmaceutically acceptable salt or stereoisomer thereof, and a pharmaceutically acceptable excipient.
17. A compound selected from the group consisting of:
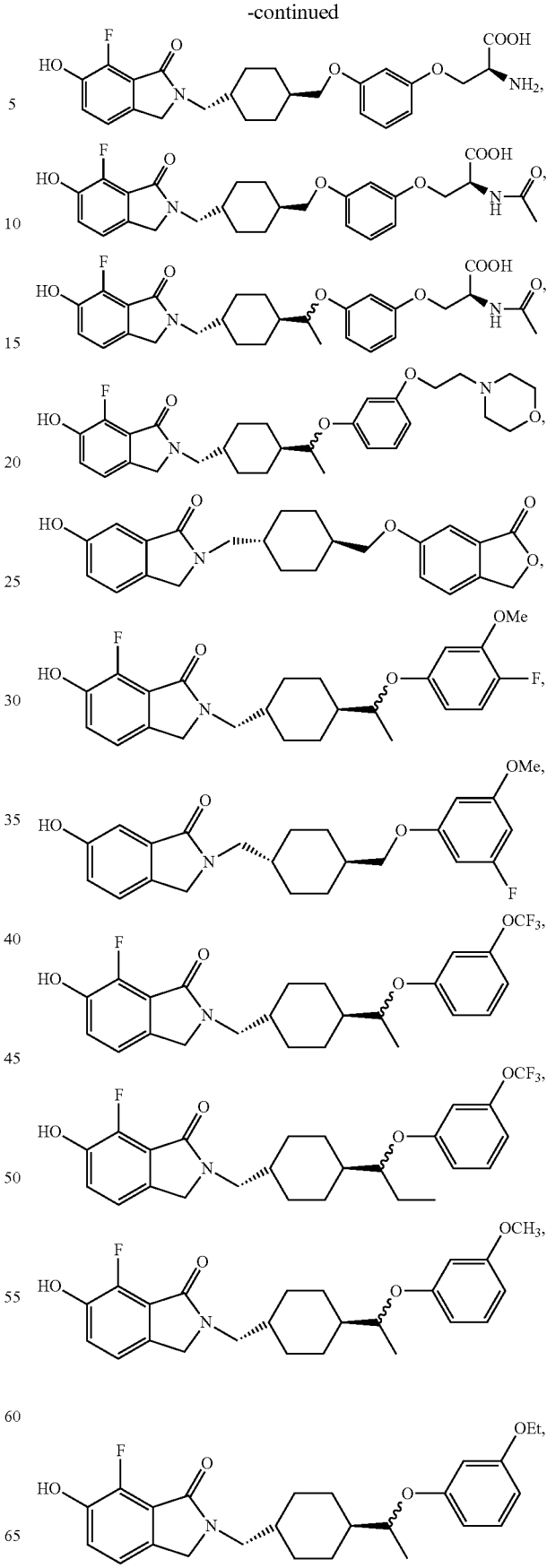

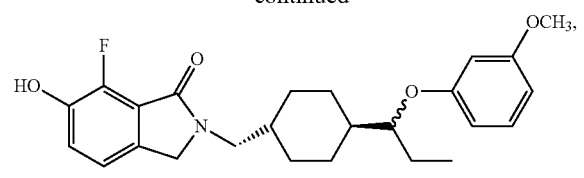
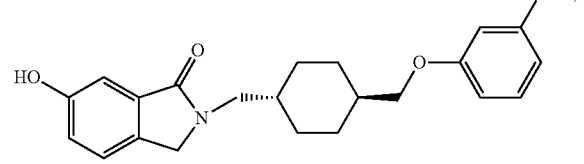
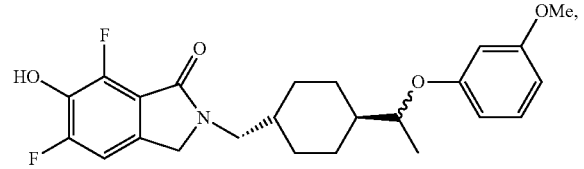
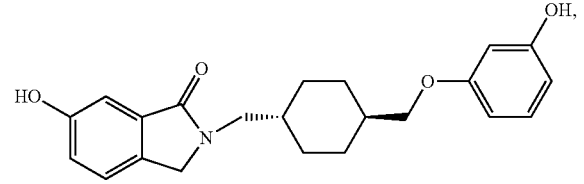
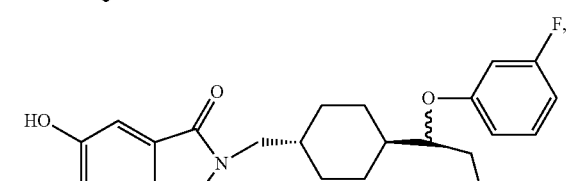
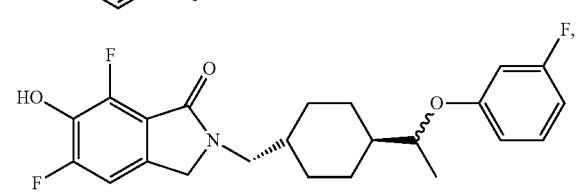
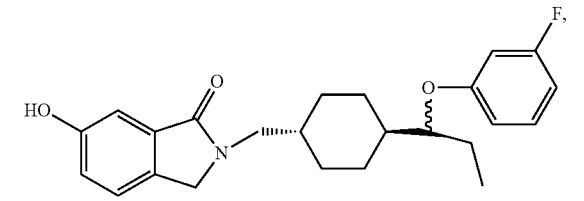
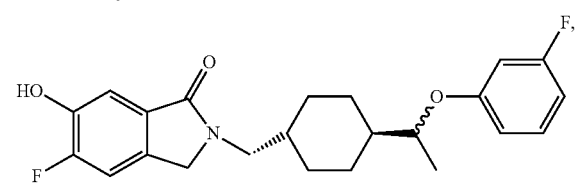
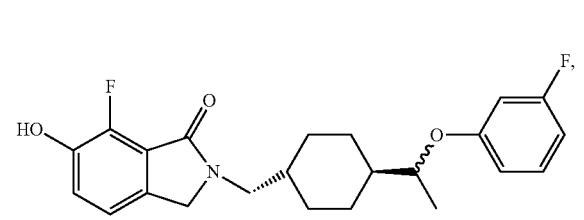
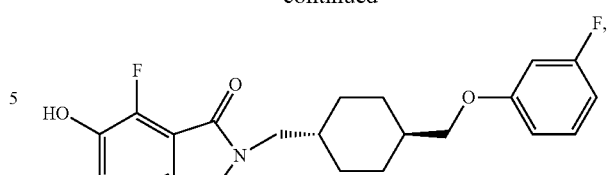
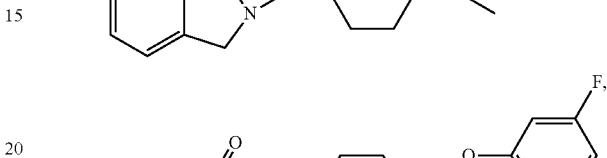
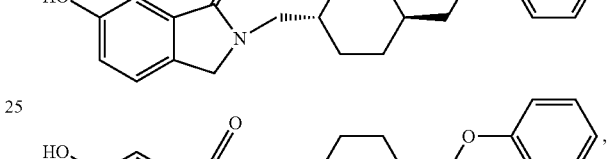
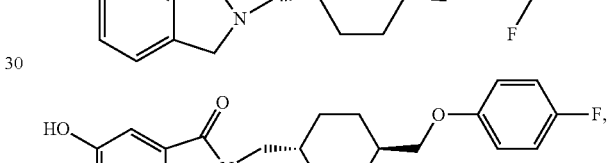
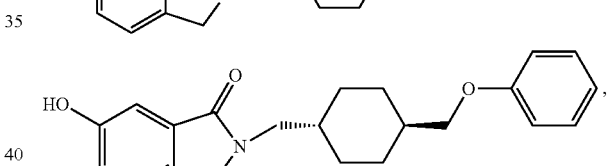
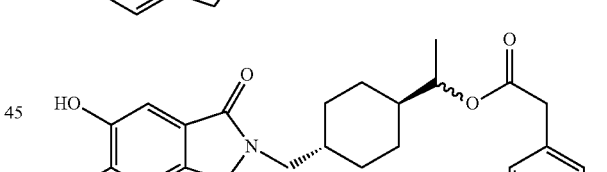
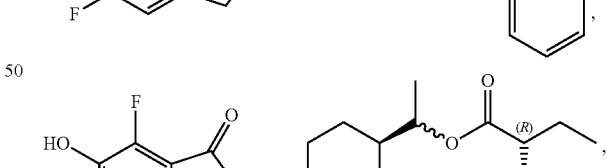
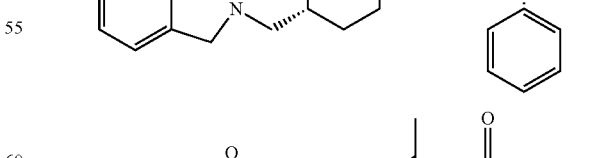
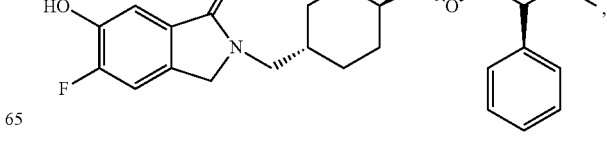

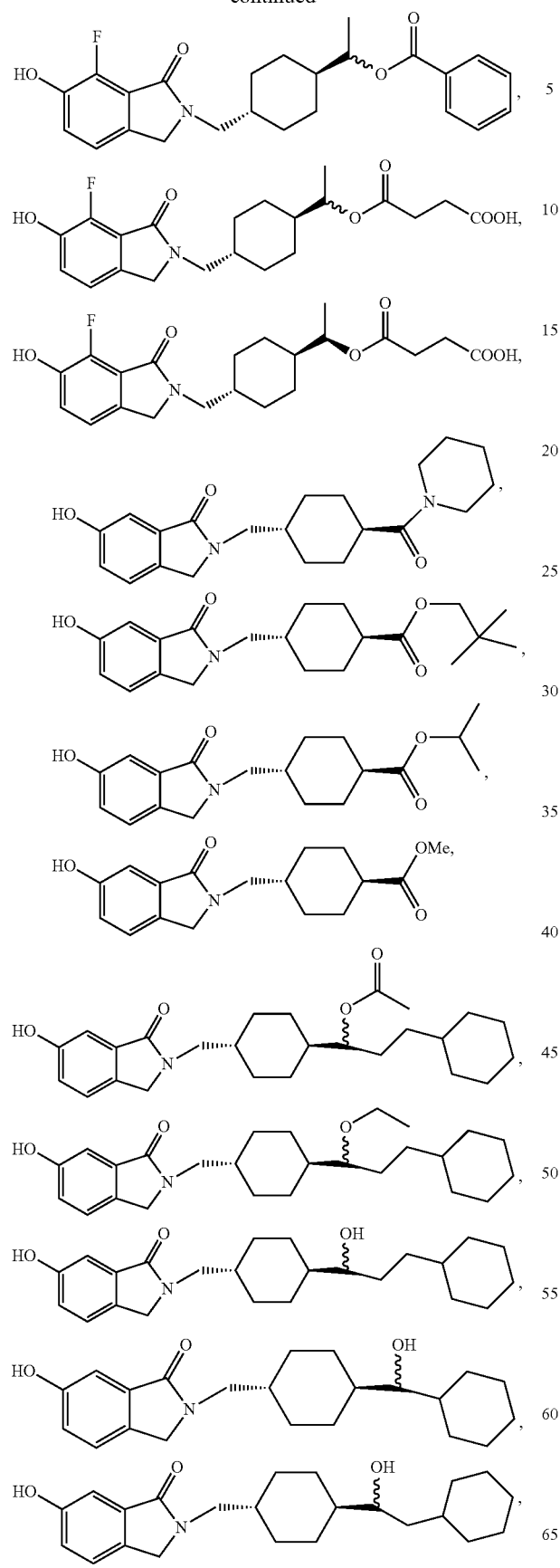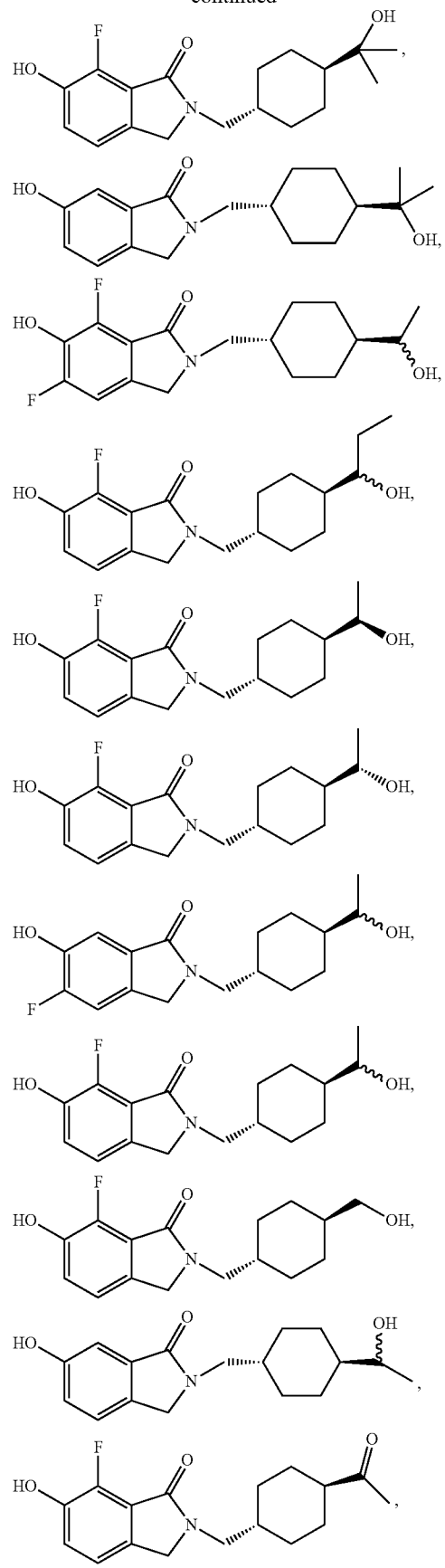

157
-continued
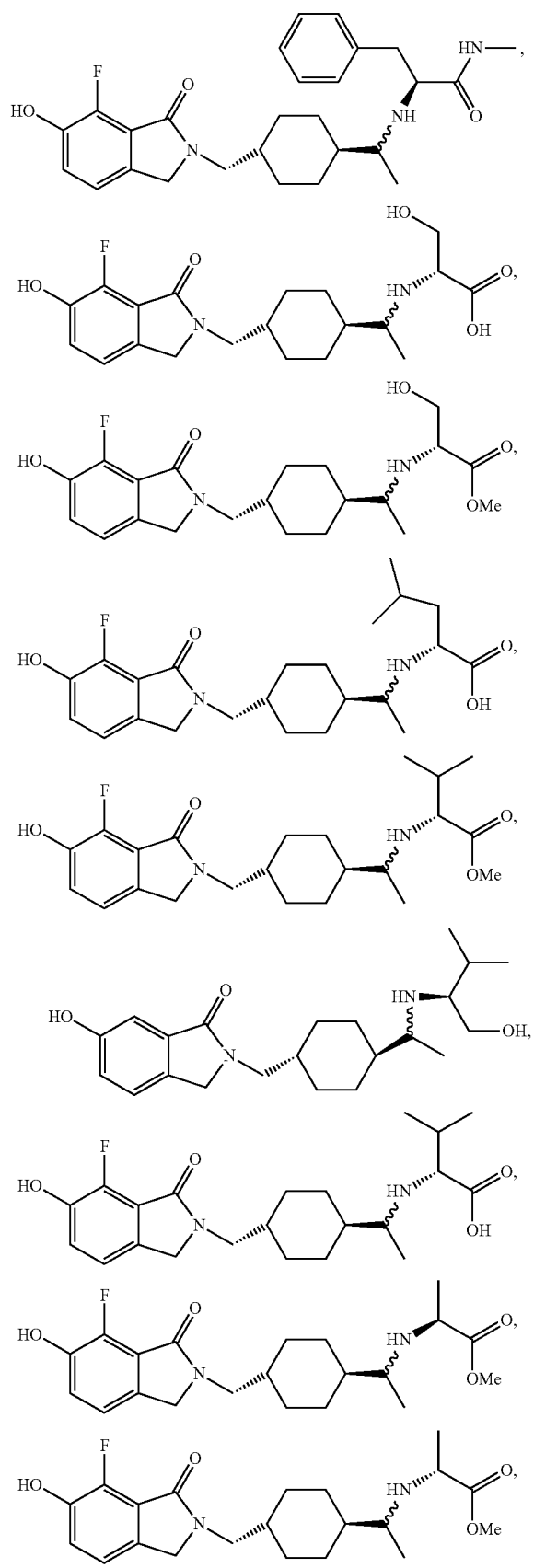
158
-continued
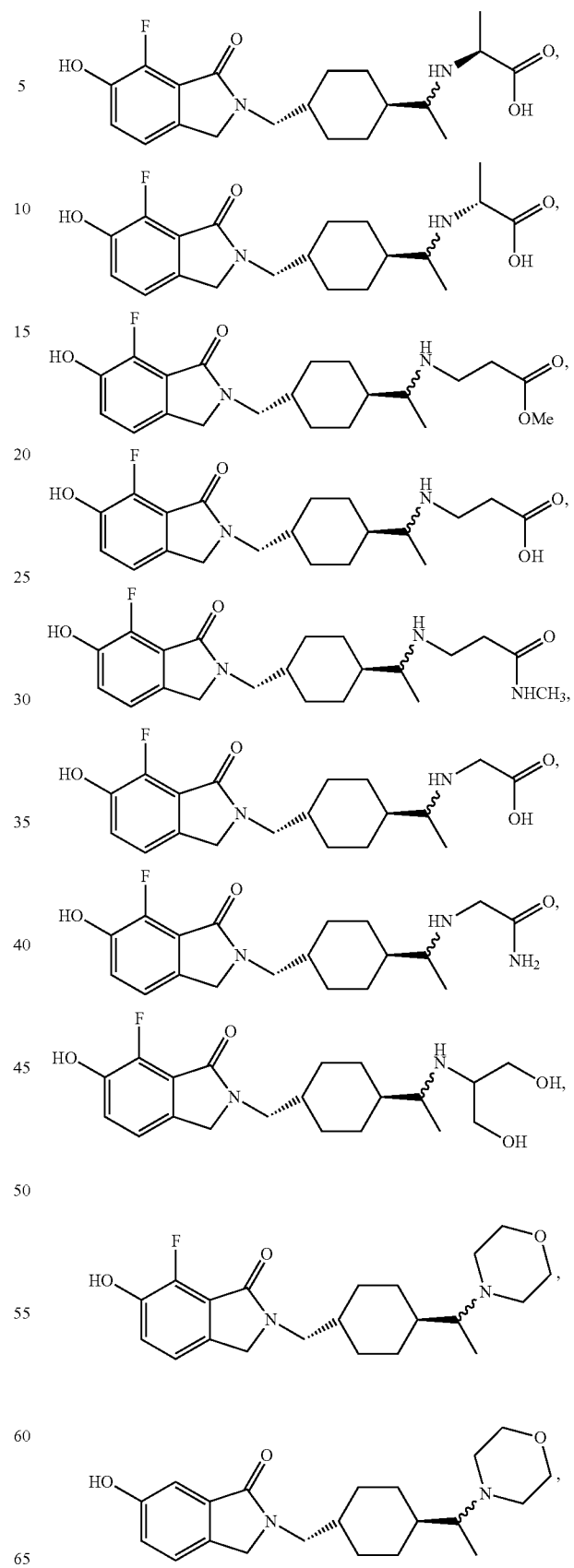

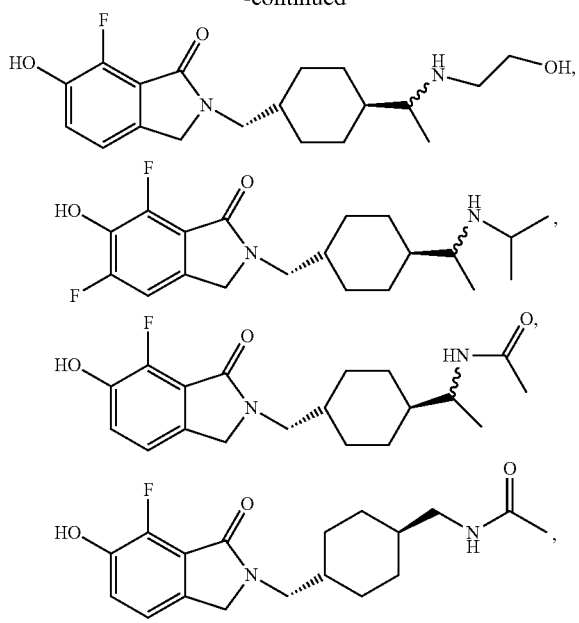

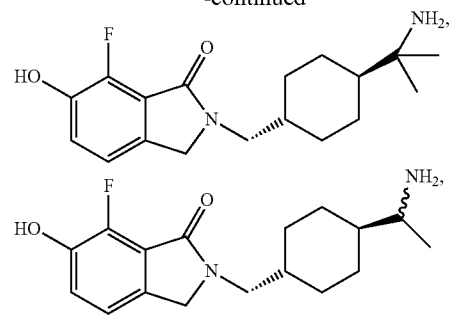

and pharmaceutically acceptable salts and stereoisomers thereof.

18. A pharmaceutical composition comprising a compound of claim 15, or a pharmaceutically acceptable salt or stereoisomer thereof, and a pharmaceutically acceptable excipient.

19. A pharmaceutical composition comprising a compound of claim 17, or a pharmaceutically acceptable salt or stereoisomer thereof, and a pharmaceutically acceptable excipient.

\* \* \* \* \*